US007771981B2

(12) United States Patent
DeAngelis

(10) Patent No.: US 7,771,981 B2
(45) Date of Patent: Aug. 10, 2010

(54) **HEPARIN/HEPAROSAN SYNTHASE FROM *P. MULTOCIDA* AND METHODS OF MAKING AND USING SAME**

(75) Inventor: Paul L. DeAngelis, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 236 days.

(21) Appl. No.: 11/975,811

(22) Filed: Oct. 22, 2007

(65) Prior Publication Data

US 2009/0023188 A1 Jan. 22, 2009

Related U.S. Application Data

(62) Division of application No. 10/142,143, filed on May 8, 2002, now Pat. No. 7,307,159.

(60) Provisional application No. 60/289,554, filed on May 8, 2001, provisional application No. 60/296,386, filed on Jun. 6, 2001, provisional application No. 60/303,691, filed on Jul. 6, 2001, provisional application No. 60/313,258, filed on Aug. 17, 2001.

(51) Int. Cl.
*C12N 1/20* (2006.01)
*C12N 9/10* (2006.01)
*C12N 15/00* (2006.01)
*C07H 21/04* (2006.01)

(52) U.S. Cl. .................. 435/252.3; 435/193; 435/320.1; 536/23.2

(58) Field of Classification Search ................. 536/23.2; 435/193, 252.3, 320.1
See application file for complete search history.

(56) References Cited

U.S. PATENT DOCUMENTS

| | | | |
|---|---|---|---|
| 5,314,876 A | 5/1994 | Lormeau et al. | |
| 5,384,398 A | 1/1995 | Lormeau et al. | |
| 5,876,433 A | 3/1999 | Lunn | |
| 5,958,899 A | 9/1999 | Zoppetti et al. | |
| 6,120,536 A | 9/2000 | Ding et al. | |
| 6,156,373 A | 12/2000 | Zhong et al. | |
| 6,162,797 A | 12/2000 | Zoppetti et al. | |
| 2006/0188966 A1* | 8/2006 | DeAngelis | 435/85 |

FOREIGN PATENT DOCUMENTS

WO    WO 03/029261 A2    10/2003

OTHER PUBLICATIONS

May, B.J. et al. Complete genomic sequence of *Pasteurella multocida*, Pm70. Proc. Natl. Acad. Sci. (USA) Mar. 2001, vol. 98. No. 6, pp. 3460-3465.
Townsend, K.M. et al. Genetic organization of *Pasteurella multocida* cap loci and development of a multiplex capsular typing system. J. Clin. Microbiol. Mar. 2001. vol. 39. No. 3, pp. 924-929.
Hill, A.L., et al.: Identification of the *Xenopus laevis* cDNA for EXT1: A Phylogenetic Perspective. DNA Sequence, 2002 vol. 13 (2), pp. 85-92; ISSN: 10472-5179; Taylor & Francis, Ltd. (USA).
Rimler, R.B.: Presumptive Identification of *Pasteurella multocida* serogroups A, D and F by capsule depolymerisation with mucopolysaccharidases. Veterinary Record (1994) 134, 191-192 (USA).
Poggi A., et al.: Inhibition of B16-BL6 melanoma lung colonies by semisynthetic sulfaminoheparosan sulfates from *E. Coli* K5 polysaccharide. Semin Thromb Hemost. Aug. 2002; 28(4): 383-92. vol. 28, No. 4.
Kim, B.T., et al.: Human tumor suppressor EXT gene family members EXTL1 and EXTL3 encode alpha 1,4-N-acetylglucosaminyltransferases that likely are involved in heparan sulfate/heparin biosynthesis. Proc. Natl. Acad. Sci. U.S.A. 2001 Jun. 19, 1998 (13):7176-81.
Vicenzi, E., et al.: Broad spectrum inhibition of HIV-1 infection by sulfated K5 *Escherichia coli* polysaccharide derivatives. AIDS. Jan. 24, 2003; 17 (2): 177-81; ISSN: 0269-9370 Lippincott Williams & Wilkins; Italy.
Lin, X, et al.: Expression and functional analysis of mouse EXT1, a homolog exostoses type 1 gene. Biochem Biophys Res Commun. Jul. 30, 1998; 248(3): 738-43; Academic Press.
Legeai-Mallet L., et al.: EXT 1 Gene Mutation Induces Chondrocyte Cytoskeletal Abnormalities and Defective Collagen Expression in the Exostoses. J Bone Miner Res. Aug. 2000; 15(8):1489-500.
McCormick, C., et al.: The putative tumor suppressor EXT1 alters the expression of cell-surface heparan sulfate. Nat. Genet. Jun. 1998; 19(2):158-61. (Canada).
Ahn, J., et al.: Cloning of the putative tumor suppressor gene for hereditary multiple exostoses (EXT1). Nat. Genet. Oct. 1995; 11(2):137-43.
Stickens, D., et al.: The EXT2 multiple exostoses gene defines a family of putative tumor suppressor genes. Nat. Genet. Sep. 1996; 14(1):25-32.
Simmons, A.D., et al.: A director interaction between EXT proteins and glycosyltransferases is defective in hereditary multple exostoses. Hum. Mol. Genet. Nov. 1999; 8(12):2155-64. (USA).
Hagner-McWhirter A., et al.: Biosynthesis of heparin/heparan sulfate: kinetic studies of the glucuronyl C5-epimerase with N-sulfated derivatives of the *Escherichia coli* K5 capsular polysaccharide as substrates. Glycobiology. Feb. 2000; 10(2):159-71. Oxford University Press. (USA).

(Continued)

*Primary Examiner*—Tekchand Saidha
(74) *Attorney, Agent, or Firm*—Dunlap Codding, P.C.

(57) ABSTRACT

The presently claimed and disclosed invention relates, in general, to dual action heparin synthases and, more particularly, to dual action heparin synthases obtained from *Pasteurella multocida*. The presently claimed and disclosed invention also relates to heparosan, heparin and heparin-like molecules provided by recombinant techniques and methods of using such molecules and also the identification or prediction of heparin synthases or component single action enzymes. The presently claimed and disclosed invention also relates to methods, and molecules produced according to such methods, for using the presently claimed and disclosed heparosan and/or heparin synthase for polymer grafting and the production of non-naturally occurring chimeric polymers incorporating stretches of one or more acidic GAG molecules, such as heparin, chondroitin, hyaluronan, and/or heparosan.

12 Claims, 11 Drawing Sheets

OTHER PUBLICATIONS

Lidholt, K., et al.: Biosynthesis of heparin. The D-glucuronosyl- and N-acetyl-D-glucosaminyltransferase reactions and their relation to polymer modification. Biochem J. Oct. 1, 1992;287 (pt 1):21-9 (Sweden).

Lin, X, et al.: Disruption of gastrulation and heparan sulfate biosynthesis in EXT1-Deficient Mice. Dev. Biol. Aug. 15, 2000; 224(2):299-311. Academic Press. (USA).

Van Hul, W., et al.: Identification of a Third EXT-like Gene (EXTL3) Belonging to the EXT Gene Family; Genomics. Jan. 15, 1998;47(2):230-7. Academic Press. (Belgium).

Nader, H.B., et al.: New insights on the specificity of heparin and haparan sulfate lyases from *Flavobacterium heparinum* revealed by the use of synthetic derivatives of K5 polysaccharide from *E. coli* and 2-O-desulfated heparin. Glycoconj J. Jun. 1999; 16(6):265-70. Kluwer Academic Publishers. Manufactured in the Netherlands. (Brazil).

DeAngelis, P.L., et al.: Identification and Molecular Cloning of a Heparosan Synthase from *Pasteurella multocida* Type D. The Journal of Biological Chemistry. vol. 277, No. 9, ISSN: Mar. 1, pp. 7209-7213, 2002. (USA).

Naggi, A., et al.: Toward a Biotechnological Heparin through Combined Chemical and Enzymatic Modification of the *Escherichia coli* K5 Polysaccharide. Seminars in Thrombosis and Hemostasis, vol. 27, No. 5, 2001; pp. 437-443. (Italy).

Leali, D., et al.: Fibroblast Growth Factor-2 Antagonist Activity and Angiostatic Capacity of Sulfated *Escherichia coli* K5 Polysaccharide Derivatives. The Journal of Biological Chemistry, vol. 276, No. 41. ISSN: Oct. 12, pp. 37900-37908, 2001. (Italy).

Duncan, G., et al.: The link between heparan sulfate and hereditary bone disease: finding a function for the EXT family of putative tumor suppressor proteins. The Journal of Clinical Investigation, Aug. 2001, vol. 108, No. 4, pp. 511-516. (USA).

Kim, B-T, et al.: Demonstration of a Novel Gene DEXT3 of *Drosophila melanogaster* as the Essential *N*-Acetylglucosamine Transferase in the Heparan Sulfate Biosynthesis. The Journal of Biological Chemistry, vol. 277, No. 16, ISSN: Apr. 19, pp. 13659-13665, 2002. (Sweden).

Sugahara, K., et al.: Heparin and Heparan Sulfate Biosynthesis. Life, 54:163-175, 2002. (Japan).

Lind, T., et al.: Biosynthesis of Heparin/Heparan Sulfate. The Journal of Biological Chemistry, vol. 268, No. 28, ISSN: Oct. 5, pp. 20705-20708, 1993. (Sweden).

Wei, G., et al.: Location of the Glucuronosyltransferase Domain in the Heparan Sulfate Copolymerase EXT1 by Analysis of Chinese Hamster Ovary Cell Mutants. The Journal of Biological Chemistry, vol. 275, No. 36, ISSN: Sep. 8, pp. 27733-27740, 2000. (USA).

Razi, N., et al.: Structural and functional properties of heparin analogues obtained by Chemical Sulphation of *Escherichia coli* K5 capsular polysaccharide. Biochem J. Jul. 15, 1995; 309 (pt2):465-72. (Sweden).

Kusche, M., et al.: Biosynthesis of heparin. Use of *Escherichia coli* K5 capsular polysaccharide as a model substrate in enzymic polymer-modification reactions. Biochem J. Apr. 1, 1991;275 (pt1):151-8. (Sweden).

Casu, B., et al.: Heparin-like compounds prepared by chemical modification of capsular polysaccharide from *E. coli*. Elsevier Science 1994; pp. 271-284. (Italy).

Vann, W.F., et al.: The Structure of the Capsular Polysaccharide (K5 Antigen) of Urinary-Tract-Infective *Escherichia coli* 010:K5:H4. Biochem J. 1981; 116; pp. 359-364. (Germany).

Toyoda, H., et al.: Structural Analysis of Glycosaminoglycans in *Drosophila* and *Caenorhabditis elegans* and Demonstrations That *tout-velu*, a *Drosophila* Gene Related to EXT Tumor Suppressors, Affects Heparan Sulfate in Vivo. The Journal of Biological Chemistry, vol. 275, No. 4; ISSN: Jan. 28, pp. 2269-2275, 2000. (Japan).

Zak, B.M., et al.: Hereditary multiple exostoses and heparan sulfate polymerization. Biochimica et Biophysica Acta 1573 (2002) 346-355. (USA).

Katada, T., et al.: cDNA cloning and distribution of XEXT1, the *Xenopus* homologue of EXT1. Dev Genese Evol. (2002) 212:248-250. (Japan).

Kitagawa, H., et al.: rib-2, a *Caenorhabditis elegans* Homolog of the Human Tumor Suppressor EXT Genes Encodes a Novel 1,4-N-Acetylglucosaminyltransferase Involved in the Biosynthetic Initiation and Elongation of Heparan Sulfate. The Journal of Biological Chemistry, vol. 276, No. 7; ISSN: Feb. 16, pp. 4834-4838, 2001. (Japan).

Song, G., et al.: Identification of mutations in the human EXT1 and EXT2 genes. Chin J. Med. Genet., Aug. 1999, vol. 16. No. 4, pp. 208-210. (China).

Clines, G.A., et al.: The Structure of the Human Multiple *Exostoses 2* Gene and Characterization of Homologs in Mouse and *Caenorhabditis elegans*. Cold Spring Harbor Laboratory Press 1997; ISSN: 1057-9803, pp. 359-367. (USA).

Wise, C.A., et al.: Identification and Localization of the Gene for EXTL, a Third Member of the Multiple Exostoses Gene Family. Cold Spring Harbor Laboratory Press 1997; ISSN: 1057-9803, pp. 10-16. (USA).

Linhardt, R.J., et al.: Production and Chemical Processing of Low Molecular Weight Heparins. Thieme Medical Publishers, Inc. 1999, vol. 25, Suppl. 3, pp. 5-16. (USA).

Fareed, J.: Heparin, Its Fractions, Fragments and Derivatives. Some Newer Perspectives. Seminars in Thrombosis and Hemostasis, vol. 11, No. 1, 1985, pp. 1-9.

Lind, T., et al.: The Putative Tumor Suppressors EXT1 and EXT2 Are Glycosyltransferases Required for the Biosynthesis of Heparan Sulfate. The Journal of Biological Chemistry, vol. 273, No. 41, ISSN: Oct. 9, pp. 26265-26268, 1998. (Sweden).

Senay, C., et al.: The EXT1/EXT2 tumor suppressors: catalytic activities and role in heparan sulfate biosynthesis. EMBO Reports vol. 1, No. 3, pp. 282-286, 2000. ((Sweden).

Bio Tie Therapies; BioHeparin—Prospectus; Jun. 2001. (Finland).

Sasisekharan, R., et al.: Heparin and heparan sulfate: biosynthesis, structure and function. Elsevier Science, Ltd. 2000; 1367-5931; pp. 626-631. (USA).

Pedersen, L.C., et al.: Heparan/Chondroitin Sulfate Biosynthesis. The Journal of Biological Chemistry, vol. 275, No. 44; ISSN: Nov. 3, pp. 34580-34585, 2000. (USA).

Finke, A., et al.: Biosynthesis of the *Escherichia coli* K5 Polysaccharide, a Representative of Group II Polysaccharides: Polymerization In Vitro and Characterization of the Product. Journal of Bacteriology, Jul. 1999, pp. 4088-4094. (Germany).

Griffiths, G., et al.: Characterization of the Glycosyltransferase Enzyme from the *Escherichia coli* K5 Capsule Gene Cluster and Identification and Charaterization of the Glucuronyl Active Site. The Journal of Biological Chemistry, vol. 273, No. 19, ISSN: May 8, pp. 11752-11757, 1998. (United Kingdom).

Hodson, N., et al.: Identification That KfiA, a Protein Essential for the Biosynthesis of the *Escherichia coli* K5 Capsular Polysaccharide, Is a UDP-GlcNAc Glycosyltransferase. The Journal of Biological Chemistry, vol. 275, No. 35, ISSN: Sep. 1, pp. 27311-27315, 2000. (United Kingdom).

Townsend, K.M., et al.: Genetic Organization of *Pasteurella multocida cap* Loci and Development of a Multiplex Capsular PCR Typing System. Journal of Clinical Microbiology, Mar. 2001, pp. 924-929. (Australia).

Boyce, J.D., et al.: *Pasteurella multocida* capsule: composition, function and genetics. Journal of Biotechnology 83 (2000) pp. 153-160. (Australia).

Rimler, R.B., et al.: Influence of chondroitinase on direct hemagglutination titers and phagocytosis of *Pasteurella multocida* serogroups A, D and F. Veterinary Microbiology 47 (1995) pp. 287-294. (USA).

Rigg, G.P., et al.: The localization of KpsC, S and T, and KfiA, C and D Proteins Involved in the biosynthesis of the *Escherichia coli* K5 capsular polysaccharide: evidence for a membrane-bound complex. Microbiology (1998), 144, 2905-2914. (United Kingdom).

DeAngelis, P.L., et al.: Identification of the capsular polysaccharides of Type D and F *Pasteurella multocida* as unmodified heparin and chondroitin, respectively. Carbohydrate Research 337 (2002) pp. 1547-1552. (USA).

Jing, W., et al.: Structure function analysis of *Pasteurella glycosaminoglycan* synthesis. Glycobiology 2002 12: abstract 188. (USA).

McCormick, C., et al.: The putative tumor suppressors EXT1 and EXT2 form a stable complex that accumulates in the Golgi apparatus and catalyzes the synthesis of heparan sulfate. PNAS, Jan. 18, 2000, vol. 97, No. 2, pp. 668-673. (Canada).

Cheung, P.K., et al.: Etiological Point Mutations in the Hereditary Multiple Exostoses Gene EXT1: A Functional Analysis of Heparan Sulfate Polymerase Activity. Am. J. Hum. Genet. 69:55-66, 2001. (Canada).

Wyatt Technology Corporation: Heparin Characterization. Apr. 5, 1997; www.tigc.org.

Soldani, G., et al.: Experimental and Clinical Pharmacology of Glycosaminoglycans (GAGs). Drugs Exptl. Clin. Res. XVII(1) 81-85 (1991). (Italy).

Van Aken, H., et al.: Anticoagulation: The Present and Future. Clin. Appl. Thrombosis/Hemostasis, 7(3): 195-204, 2001. (Germany).

Lidholt, K., et al.: Substrate specificities of glycosyltransferases involved in formation of heparin precursor and *E. Coli* K5 capsular polysaccharides. Carbohydrate Research, 255 (1994) 87-101. (Sweden).

Roberts, I., et al.: Molecular Cloning and Analysis of Genes for Production of K5, K7, K12, and K92 Capsular Polysaccharides in *Escherichia coli*. J. Bacteriology; Dec. 1986, pp. 1228-1233. (Germany).

Kroncke, K.D., et al.: Expression of the *Escherichia coli* K5 Capsular Antigen: Immunoelectron Microscopic and Biochemical Studies with Recombinant *E. coli*. J. Bacteriology, Feb. 1990, pp. 1085-1091. (Germany).

Roberts, I.S., et al.: Common Organization of Gene Clusters for Production of Different Capsular Polysaccharides (K Antigens) in *Escherichia coli*. J. Bacteriology, Mar. 1988, pp. 1305-1310. (United Kingdom).

Petit, C., et al.: Region 2 of the *Escherichia coli* K5 capsule gene cluster encoding proteins for the biosynthesis of the K5 polysaccharide. Molecular Microbiology (1995) 17(4), pp. 611-620. (United Kingdom).

Smith, A.N., et al.: Molecular analysis of the *Escherichia coli* K5 *kps* locus: identification and characterization of an inner-membrane capsular polysaccharide transport system. Molecular Microbiology (1990) 4(11), pp. 1863-1869. (United Kingdom).

Bronner, D., et al.: Synthesis of the K5 (group II) capsular polysaccharide in transport-deficient recombinant *Escherichia coli*. FEMS Microbiology Letters 113 (1993), pp. 273-284. (Germany).

Pandit, K.K., et al.: Capsular hyaluronic acid in *Pasteurella multocida* type A and its counterpart in type D. Research in Veterinary Science. 54:20-24 (1993).

Linharrdt, R.J. et al.; "Isolation and characterization of human heparin". Biochemistry, vol. 31(49): 12441-12445 (1992).

DeAngelis, P.; "Microbial glycosaminoglycan glycosyltransferases". Glysobiology, vol. 12(1): 9R-16R (2002).

* cited by examiner

FIG. 1

```
         91                                                              140
HS1      APPLVSIIMTSHNTEKFIEASINSLLLQTYNNLEVIVVDDYSTDKTFQIA
KfiC     GKDLVSIIMSVFNSEDTIAYSLHSLLNQTYENIEILVCDDCSSDKSLEII
con      ...LVSIIM*..N*E..I...S..SLL.QTY#N.E!.V.DD.S*DK*.#I.

141                                                             190
HS1      SRIANSTSKVKTFRLNSNLGTYFAKNTGILKSKGDIFFQDSDDVCHHER
KfiC     KSIAYSSSRVKVYSSRKNQGPYNIRNELIKKAHGNFITFQDADDLSHPER
con      ..IA.S*S*VK.%.....N.G.Y....N..I.K..G#..I.FQD.DD..H.ER 191                                                             240
HS1      IERCVNALLSNKDNIAVRCAYSRINLETQNIIKVNDNKYKLGLITLGVYR
KfiC     IQRQVEVLRNNKAVICM.ANWIRVASNGKIQFFYDDKATRMSVVSSMIKK
con      I#R.V#.L..NK..I......R!..#......#D...*$..!.!.*

441                                                             490
HS2      YITCDDDIRYPADYINTMIKKINKYND.KAAIGLHGVIFPSRVNKYFSSD
KfiA     IVLTDDDIIYPPDYVEKMLNFYNSFAIFNCIVGIHGCIYIDAFDGD.QSK
con      .!..DDDI.YP.DY!.#..M....N.%......!G.HG.I%....#....S.

491                                                             540
HS2      RIVYNFQKTFRKDTAVNILGTGTVAFRVSIFNKFSLSDFEHPGMVDIYFS
KfiA     RKVFSFTQGLLRPRVVNQLGTGTVFLKADQLPSLKYMDGSQR.FVDVRFS
con      R.V%.F.....*....VN.LGTGTV..*.........D.......VD!.FS
```

FIG. 4A

```
              1           10          20          30          40          50          60          70
              |-----------+-----------+-----------+-----------+-----------+-----------+-----------|
KfiC          GKDLVSIIMSYFNSEDTIAYSLHSLLNQTYENIEILVCDDCSSQKSLEIIKSIAYSSSRVKVYSSRKNQG
HSA1          APPLVSIIMTSHNTEKFIEASINSLLLQTYNNLEVIVVDDYSTDKTFQIASRIANSTSKVKTFRLNSNLG
kfiA          MIYANMSSYPPRKKELVHSIQSLHAQV-DKIMLCLNEFEEIPEELDGFSKLNPYI----PDKDYKDVG
HSA2          IPYYINICSIPSRIKQLQYTIGVLKNQC-DHFHIYLDGYPEVPQFIKKLGNKATYINCQNKNESIRDNG
Consensus     ..p.v.ni.s.p.r.k.l.ysi.sL.nQ..#..i.l....e.P..l....s..a.vi.......s..k#.G 71           80          90         100         110         120         130        140
              |-----------+-----------+-----------+-----------+-----------+-----------+-----------|
KfiC          PYNIRNELIKKAHGNFITFQDADDLSHPERIQRQVEVLRNNKAVICH-ANHIRVASNGKIQFFYDDKATR
HSA1          TYFAKNTGILKSKGDIIFFQDSDDVCHHERIERCVNALLSNKONIAVRCAYSRINLETQNIIKVNDNKYK
kfiA          KFIF-----PCAKMDMIVLTDDDIIYPPDYVEKMLNFYNSFAIFNCIVGIHGCIYIDAFDGD-QSKRKV-
HSA2          KFILLEKLIKENKDGYYITCDDDIRYPADYINTHIKKINKYND-KAAIGLHGVIFPSRVNKYFSSDRIV-
Consensus     k%i....lik.ak.d.i....DdDi.ypp#y!#.n.n..ns..d..a..g.hg.!.....n..f..sdrkv.

141          150         160         170         180         190         200        210
              |-----------+-----------+-----------+-----------+-----------+-----------+-----------|
KfiC          MSVVSSHIKKDIFATVGGYRQSLIGADTEFYETVIMRYGRESIVRLLQPLILGLWGDSGLTRNKGTEALP
HSA1          LGLITLGVYRKVFMEIGFFNCITKASDDEFYHRIIKYYGKNRINMLFLPLYYNTHREDSLFSOM-VEHVD
kfiA          FSFTQGLLRPRVVNQLG--TGTVFLKADQLPSLKYMDGSQR-FVDVRFSRYMLENEIGMICVPREKNHLR
HSA2          YNFQKTFRKDTAVMILG--TGTVAFRVSIFNKFSLSDFEHPGMVDIYFSILCKKNNILQVCISRPSNWLT
Consensus     .sf.....k..vvn.lG..tgtv....d.f.....md......vd..fs..y....n.i...c..r..#wl.

211          220         230         240         250         260263
              |-----------+-----------+-----------+-----------+-----------+--|
KfiC          DGYISQSRREYSDIAARQRVLGKSIYSDKDVRGLLSRYGLFKDYSGIIEQ
HSA1          ENNIKQKTSDARQMYLHEFQKIHNERKFNELKEIFS-FPRIHDALPISKEMSK
kfiA          EVS-SGSMEGLANTFTKKAPLDI-IKETQAIAGYSKLNLELVYNVEG
HSA2          EDN-KNT-ETLFHEFQNRDEIQSKLIISNMPWGYASSIYPLLNNNANYSELIPC
Consensus     #.n.k.s.e.l....f.....l...i....n...gyss.ypll..n...se....
```

FIG. 4B

```
             1         10        20        30        40        50        60        70
             |---------+---------+---------+---------+---------+---------+---------|
    pnHS                             MSLFKRATELFKSGNYKDALTLYENIAKIYG----SESLVKYNIDI
    pglA     MKRKKEHTQKQHTKNPPQHEKENELNTFQNKIDSLKTTLNKDIISQQTLLAKQDSKHPLSASLENENKLL
    DcbF                             MSLFKRATELFKSGNYKDALTLYENIAKIYG----SESLVKYNIDI
Consensus    ...................$slFkrat#lfKsgnyKDaltlyeniAKiyg....SeSLvkyNidi 71        80        90        100       110       120       130       140
             |---------+---------+---------+---------+---------+---------+---------|
    pnHS     CKK-NITQSKSNKIEEDNISGENKF-----SVSIKDLYNEISNSELGITKERLGAPPLVSIIMTSHNTEK
    pglA     LKQLQLVLQEFEKIYTYNQALEAKLEKDKQTTSITDLYNEVAKSDLGLVKETNSVNPLVSIIMTSHNTAQ
    DcbF     CKK-NITQSKSNKIEEDNISGENEF-----SVSIKDLYNEISNSELGITKERLGAPPLVSIIMTSHNTEK
Consensus    cKk.#itqsks#KIeedNisgEnkf.....svSIkDLYNE!snS#LGitKErlgapPLVSIIMTSHNTek 141       150       160       170       180       190       200       210
             |---------+---------+---------+---------+---------+---------+---------|
    pnHS     FIEASINSLLLQTYNNLEVIVVDDYSTDKTFQIASRIANSTSKVKTFRLNSNLGTYFAKNTGILKSKGDI
    pglA     FIEASINSLLLQTYKNIEIIIVDDDSSDNTFEIASRIANTTSKVRVFRLNSNLGTYFAKNTGILKSKGDI
    DcbF     FIEASINSLLLQTYNNLEVIVVDDYSTDKTFQIASRIANSTSKVKTFRLNSNLGTYFAKNTGILKSKGDI
Consensus    FIEASINSLLLQTYnNlE!I!VDDgStDkTF#IASRIANsTSKVktFRLNSNLGTYFAKNTGILKSKGDI 211       220       230       240       250       260       270       280
             |---------+---------+---------+---------+---------+---------+---------|
    pnHS     IFFQDSDDVCHHERIERCVNALLSNKDNIAVRCAYSRINLETQNIIKVNDNKYKLGLITLGVYRKVFNEI
    pglA     IFFQDSDDVCHHERIERCVNILLANKETIAVRCAYSRLAPETQHIIKVNNNMDYRLGFITLGMHRKVFQEI
    DcbF     IFFQDSDDVCHHERIERCVNALLSNKDNIAVRCAYSRINLETQNIIKVNDNKYKLGLITLGVYRKVFNEI
Consensus    IFFQDSDDVCHHERIERCVNaLLsNK#nIAVRCAYSRinlETQnIIKVN#nkYkLGlITLGvyRKVF#EI 281       290       300       310       320       330       340       350
             |---------+---------+---------+---------+---------+---------+---------|
    pnHS     GFFNCTTKASDDEFYHRIIKYYGKNRIHNLFLPLYYNTHREDSLFSDMVEHVDENNIKQKTSDARQNYLH
    pglA     GFFNCTTKGSDDEFFHRIAKYYGKEKIKNLLLPLYYNTHRENSLFTDMVEHIDNHNIIQKMSDTRQHYAT
    DcbF     GFFNCTTKASDDEFYHRIIKYYGKNRIHNLFLPLYYNTHREDSLFSDMVEHVDENNIKQKTSDARQNYLH
Consensus    GFFNCTTKaSDDEF%HRIiKYYGK#rInNLfLPLYYNTHRE#SLFsDMVEH!D#nNIkQKtSDaRQnYlh 351       360       370       380       390       400       410       420
             |---------+---------+---------+---------+---------+---------+---------|
    pnHS     EFQKIHNERKLNELKEIFSFPRIHDALPISKEMSKLSNPKIPVYINICSIPSRIKQLQYTIGVLKNQCDH
    pglA     LFQRMHNETASHDFKNLFQFPRIYDALPVPQEMSKLSNPKIPVYINICSIPSRIAQLRRIIGILKNQCDH
    DcbF     EFQKIHNERKFNELKEIFSFPRIHDALPISKEMSKLSNPKIPVYINICSIPSRIKQLQYTIGVLKNQCDH
Consensus    eFQkiHNErk.n#lK#iFsFPRIhDALP!skEMSKLSNPKIPVYINICSIPSRIkQLqytIG!LKNQCDH 421       430       440       450       460       470       480       490
             |---------+---------+---------+---------+---------+---------+---------|
    pnHS     FHIYLDGYPEVPDFIKKLGNKATVINCQNKNESIRDNGKFILLEKLIKENKDGYYITCDDDIRYPADYTN
    pglA     FHIYLDGYVEIPDFIKNLGNKATVVHCKDKDNSIRDNGKFILLEELIEKNQDGYYITCDDDIIYPSDYIN
    DcbF     FHIYLDGYPEVPDFIKKLGNKATVINCQNKNESIRDNGKFILLEKLIKENKDGYYITCDDDIRYPADYIN
Consensus    FHIYLDGYpE!PDFIKkLGNKATV!nCq#K##SIRDNGKFILLEkLIkeNkDGYYITCDDDIrYPaDYiN 491       500       510       520       530       540       550       560
             |---------+---------+---------+---------+---------+---------+---------|
    pnHS     TMIKKINKYNDKARIGLHGVIFPSRVNKYFSSDRIVYNFQKPLENDTAVNILGTGTVAFRVSIFNKFSLS
    pglA     TMIKKLNEYDDKAVIGLHGILFPSRMTKYFSADRLVYSFYKPLEKDKAVNVLGTGTVSFRVSLFNQFSLS
    DcbF     TMIKKINKYNDKARIGLHGVIFPSRVNKYFSSDRIVYNFQKTFRK
Consensus    TMIKKiNkY#DKAaIGLHG!iFPSRvnKYFSsDRiVYnFqKplekd.avn.lgtgtv.frvs.fn.fsls 561       570       580       590       600       610       620       630
             |---------+---------+---------+---------+---------+---------+---------|
    pnHS     DFEHPGMVDIYFSILCKKNNILQVCISRPSNWLTEDNKNTETLFHEFQNRDEIQSKLIISHNPHGYSSIY
    pglA     DFTHSGMADIYFSLLCKKNNILQICISRPANWLTEDNRDSETLYHQYRDNDEQQTQLIMENGPHGYSSIY
    DcbF
Consensus    df.h.gm.diyfs.lckknnilq.cisrp.nwltedn...etl.h.....de.q..li..n.pwgyssiy 631       640       651
             |---------+---------+|
    pnHS     PLLNNNRANYSELIPCLSFYNE
    pglA     PLVKNHPKFTDLIPCLPFYFL
    DcbF
Consensus    pl..n......lipcl.fy..
```

FIG. 4C

```
Multalin version 5.4.1
Copyright I.N.R.A. France 1989, 1991, 1994, 1996
Published research using this software should cite
Multiple sequence alignment with hierarchical clustering
F. CORPET, 1988, Nucl. Acids Res., 16 (22), 10881-10890
Symbol comparison table: blosum62
Gap weight: 12
Gap length weight: 2
Consensus levels: high=90% low=50%
Consensus symbols:
 ! is anyone of IV
 $ is anyone of LM
 % is anyone of FY
 # is anyone of NDQEBZ MSF:      651    Check:    0       ..
 Name: A              Len:  651   Check:  612   Weight:  0.58
 Name: B              Len:  651   Check:  249   Weight:  0.58
 Name: pglA           Len:  651   Check: 7677   Weight:  1.08
 Name: DcbF           Len:  651   Check: 7537   Weight:  1.76
 Name: Consensus      Len:  651   Check: 5816   Weight:  0.00

//

1                                                       50
           A2      .......... ..........  ....MSLFKR ATELFKSGNY KDALTLYENI
           B10     .......... ..........  ....MSLFKR ATELFKSGNY KDALTLYENI
           pglA    MKRKKEMTQK QMTKNPPQHE   KENELNTFQN KIDSLKTTLN KDIISQQTLL
           DcbF    .......... ..........  ....MSLFKR ATELFKSGNY KDALTLYENI
           sensus  .......... ..........  ....$slFkr at#lfKsgny KDaltlyeni 51                                                     100
           A2      AKIYG....S ESLVKYNIDI  CKK.NITQSK SNKIEEDNIS GENKF.....
           B10     AKIYG....S ESLVKYNIDI  CKK.NITQSK SNKIEEDNIS GENKF.....
           pglA    AKQDSKHPLS ASLENENKLL  LKQLQLVLQE FEKIYTYNQA LEAKLEKDKQ
           DcbF    AKIYG....S ESLVKYNIDI  CKK.NITQSK SNKIEEDNIS GENEF.....
        Consensus  AKIyg....S eSLvkyNidi  cKk.#itqsk s#KIeedNis gEnkf.....

101                                                    150
           A2      SVSIKDLYNE ISNSELGITK  ERLGAPPLVS IIMTSHNTEK FIEASINSLL
           B10     SVSIKDLYNE ISNSELGITK  ERLGAPPLVS IIMTSHNTEK FIEASINSLL
           pglA    TTSITDLYNE VAKSDLGLVK  ETNSVNPLVS IIMTSHNTAQ FIEASINSLL
           DcbF    SVSIKDLYNE ISNSELGITK  ERLGAPPLVS IIMTSHNTEK FIEASINSLL
        Consensus  svSIkDLYNE !snS#LGitK  ErlgapPLVS IIMTSHNTek FIEASINSLL 151                                                    200
           A2      LQTYNNLEVI VVDDYSTDKT  FQIASRIANS TSKVKTFRLN SNLGTYFAKN
           B10     LQTYNNLEVI VVDDYSTDKT  FQIASRIANS TSKVKTFRLN SNLGTYFAKN
           pglA    LQTYKNIEII IVDDDSSDNT  FEIASRIANT TSKVRVFRLN SNLGTYFAKN
           DcbF    LQTYNNLEVI VVDDYSTDKT  FQIASRIANS TSKVKTFRLN SNLGTYFAKN
        Consensus  LQTYnNlE!I !VDDyStDkT  F#IASRIANs TSKVktFRLN SNLGTYFAKN
```

FIG. 4C contd.

```
           201                                                         250
        A2 TGILKSKGDI IFFQDSDDVC HHERIERCVN ALLSNKDNIA VRCAYSRINL
       B10 TGILKSKGDI IFFQDSDDVC HHERIERCVN ALLSNKDNIA VRCAYSRINL
      pglA TGILKSKGDI IFFQDSDDVC HHERIERCVN ILLANKETIA VRCAYSRLAP
      DcbF TGILKSKGDI IFFQDSDDVC HHERIERCVN ALLSNKDNIA VRCAYSRINL
 Consensus TGILKSKGDI IFFQDSDDVC HHERIERCVN aLLsNK#nIA VRCAYSRinl 251                                                         300
        A2 ETQNIIKVND NKYKLGLITL GVYRKVFNEI GFFNCTTKAS DDEFYHRIIK
       B10 ETQNIIKVND NKYKLGLITL GVYRKVFNEI GFFNCTTKAS DDEFYHRIIK
      pglA ETQHIIKVNN MDYRLGFITL GMHRKVFQEI GFFNCTTKGS DDEFFHRIAK
      DcbF ETQNIIKVND NKYKLGLITL GVYRKVFNEI GFFNCTTKAS DDEFYHRIIK
 Consensus ETQnIIKVN# nkYkLGlITL GvyRKVF#EI GFFNCTTKaS DDEF%HRiiK 301                                                         350
        A2 YYGKNRINNL FLPLYYNTMR EDSLFSDMVE WVDENNIKQK TSDARQNYLH
       B10 YYGKNRINNL FLPLYYNTMR EDSLFSDMVE WVDENNIKQK TSDARQNYLH
      pglA YYGKEKIKNL LLPLYYNTMR ENSLFTDMVE WIDNHNIIQK MSDTRQHYAT
      DcbF YYGKNRINNL FLPLYYNTMR EDSLFSDMVE WVDENNIKQK TSDARQNYLH
 Consensus YYGK#rInNL fLPLYYNTMR E#SLFsDMVE W!D#nNIkQK tSDaRQnYlh 351                                                         400
        A2 EFQKIHNERK LNELKEIFSF PRIHDALPIS KEMSKLSNPK IPVYINICSI
       B10 EFQKIHNERK LNELKEIFSF PRIHDALPIS KEMSKLSNPK IPVYINICSI
      pglA LFQAMHNETA SHDFKNLFQF PRIYDALPVP QEMSKLSNPK IPVYINICSI
      DcbF EFQKIHNERK FNELKEIFSF PRIHDALPIS KEMSKLSNPK IPVYINICSI
 Consensus eFQkiHNErk .n#lK#iFsF PRIhDALP!s kEMSKLSNPK IPVYINICSI 401                                                         450
        A2 PSRIKQLQYT IGVLKNQCDH FHIYLDGYPE VPDFIKKLGN KATVINCQNK
       B10 PSRIKQLQYT IGVLKNQCDH FHIYLDGYPE VPDFIKKLGN KATVINCQNK
      pglA PSRIAQLRRI IGILKNQCDH FHIYLDGYVE IPDFIKNLGN KATVVHCKDK
      DcbF PSRIKQLQYT IGVLKNQCDH FHIYLDGYPE VPDFIKKLGN KATVINCQNK
 Consensus PSRIkQLqyt IG!LKNQCDH FHIYLDGYpE !PDFIKkLGN KATV!nCq#K 451                                                         500
        A2 NESIRDNGKF ILLEKLIKEN KDGYYITCDD DIRYPADYTN TMIKKINKYN
       B10 NESIRDNGKF ILLEKLIKEN KDGYYITCDD DIRYPADYIN TMIKKINKYN
      pglA DNSIRDNGKF ILLEELIEKN QDGYYITCDD DIIYPSDYIN TMIKKLNEYD
      DcbF NESIRDNGKF ILLEKLIKEN KDGYYITCDD DIRYPADYIN TMIKKINKYN
 Consensus ##SIRDNGKF ILLEkLIkeN kDGYYITCDD DIrYPaDYiN TMIKKiNkY#

501                                                         550
        A2 DKAAIGLHGV IFPSRVNKYF SSDRIVYNFQ KPLENDTAVN ILGTGTVAFR
       B10 DKAAIGLHGV IFPSRVNKYF SSDRIVYNFQ KPLENDTAVN ILGTGTVAFR
      pglA DKAVIGLHGI LFPSRMTKYF SADRLVYSFY KPLEKDKAVN VLGTGTVSFR
      DcbF DKAAIGLHGV IFPSRVNKYF SSDRIVYNFQ KTFRK..... ..........
 Consensus DKAaIGLHG! iFPSRvnKYF SsDRiVYnFq Kplekd.avn .lgtgtv.fr 551                                                         600
        A2 VSIFNKFSLS DFEHPGMVDI YFSILCKKNN ILQVCISRPS NWLTEDNKNT
       B10 VSIFNKFSLS DFEHPGMVDI YFSILCKKNN ILQVCISRPS NWLTEDNKNT
      pglA VSLFNQFSLS DFTHSGMADI YFSLLCKKNN ILQICISRPA NWLTEDNRDS
      DcbF .......... .......... .......... .......... ..........
 Consensus vs.fn.fsls df.h.gm.di yfs.lckknn ilq.cisrp. nwltedn...
```

FIG. 4C contd.

```
            601                                                    650
       A2   ETLFHEFQNR DEIQSKLIIS NNPWGYSSIY PLLNNNANYS ELIPCLSFYN
      B10   ETLFHEFQNR DEIQSKLIIS NNPWGYSSIY PLLNNNANYS ELIPCLSFYN
     pglA   ETLYHQYRDN DEQQTQLIME NGPWGYSSIY PLVKNHPKFT DLIPCLPFYF
     DcbF   .......... .......... .......... .......... ..........
Consensus   etl.h..... de.q..li.. n.pwgyssiy pl...n..... .lipcl.fy.

651
       A2   E
      B10   E
     pglA   L
     DcbF   .
Consensus   .
```

FIG. 4D

```
Multalin version 5.4.1
Copyright I.N.R.A. France 1989, 1991, 1994, 1996
Published research using this software should cite
Multiple sequence alignment with hierarchical clustering
F. CORPET, 1988, Nucl. Acids Res., 16 (22), 10881-10890
Symbol comparison table: blosum62
Gap weight: 12
Gap length weight: 2
Consensus levels: high=90% low=50%
Consensus symbols:
 ! is anyone of IV
 $ is anyone of LM
 % is anyone of FY
 # is anyone of NDQEBZ MSF:    651     Check:     0       ..
Name: pmHS         Len:   651  Check:  612   Weight: 0.75
Name: pglA         Len:   651  Check: 7677   Weight: 0.75
Name: DcbF         Len:   651  Check: 7537   Weight: 1.49
Name: Consensus    Len:   651  Check: 5816   Weight: 0.00

//

1                                                          50
         pmHS      .......... ..........  ....MSLFKR ATELFKSGNY KDALTLYENI
         pglA      MKRKKEMTQK QMTKNPPQHE  KENELNTFQN KIDSLKTTLN KDIISQQTLL
         DcbF      .......... ..........  ....MSLFKR ATELFKSGNY KDALTLYENI
    Consensus      .......... ..........  ....$slFkr at#lfKsgny KDaltlyeni 51                                                        100
         pmHS      AKIYG....S ESLVKYNIDI  CKK.NITQSK SNKIEEDNIS GENKF.....
         pglA      AKQDSKHPLS ASLENENKLL  LKQLQLVLQE FEKIYTYNQA LEAKLEKDKQ
         DcbF      AKIYG....S ESLVKYNIDI  CKK.NITQSK SNKIEEDNIS GENEF.....
    Consensus      AKIyg....S eSLvkyNidi  cKk.#itqsk s#KIeedNis gEnkf.....

101                                                       150
         pmHS      SVSIKDLYNE ISNSELGITK  ERLGAPPLVS IIMTSHNTEK FIEASINSLL
         pglA      TTSITDLYNE VAKSDLGLVK  ETNSVNPLVS IIMTSHNTAQ FIEASINSLL
         DcbF      SVSIKDLYNE ISNSELGITK  ERLGAPPLVS IIMTSHNTEK FIEASINSLL
    Consensus      svSIkDLYNE !snS#LGitK  ErlgapPLVS IIMTSHNTek FIEASINSLL 151                                                       200
         pmHS      LQTYNNLEVI VVDDYSTDKT  FQIASRIANS TSKVKTFRLN SNLGTYFAKN
         pglA      LQTYKNIEII IVDDDSSDNT  FEIASRIANT TSKVRVFRLN SNLGTYFAKN
         DcbF      LQTYNNLEVI VVDDYSTDKT  FQIASRIANS TSKVKTFRLN SNLGTYFAKN
    Consensus      LQTYnNlE!I !VDDyStDkT  F#IASRIANs TSKVktFRLN SNLGTYFAKN 201                                                       250
         pmHS      TGILKSKGDI IFFQDSDDVC  HHERIERCVN ALLSNKDNIA VRCAYSRINL
         pglA      TGILKSKGDI IFFQDSDDVC  HHERIERCVN ILLANKETIA VRCAYSRLAP
         DcbF      TGILKSKGDI IFFQDSDDVC  HHERIERCVN ALLSNKDNIA VRCAYSRINL
    Consensus      TGILKSKGDI IFFQDSDDVC  HHERIERCVN aLLSNK#nIA VRCAYSRinl 251                                                       300
         pmHS      ETQNIIKVND NKYKLGLITL  GVYRKVFNEI GFFNCTTKAS DDEFYHRIIK
         pglA      ETQHIIKVNN MDYRLGFITL  GMHRKVFQEI GFFNCTTKGS DDEFFHRIAK
         DcbF      ETQNIIKVND NKYKLGLITL  GVYRKVFNEI GFFNCTTKAS DDEFYHRIIK
    Consensus      ETQnIIKVN# nkYkLGlITL  GvyRKVF#EI GFFNCTTKaS DDEF%HRIiK
```

FIG. 4D contd.

```
            301                                                        350
     pmHS   YYGKNRINNL FLPLYYNTMR EDSLFSDMVE WVDENNIKQK TSDARQNYLH
     pglA   YYGKEKIKNL LLPLYYNTMR ENSLFTDMVE WIDNHNIIQK MSDTRQHYAT
     DcbF   YYGKNRINNL FLPLYYNTMR EDSLFSDMVE WVDENNIKQK TSDARQNYLH
Consensus   YYGK#rInNL fLPLYYNTMR E#SLFsDMVE W!D#nNIkQK tSDaRQnYlh 351                                                        400
     pmHS   EFQKIHNERK LNELKEIFSF PRIHDALPIS KEMSKLSNPK IPVYINICSI
     pglA   LFQAMHNETA SHDFKNLFQF PRIYDALPVP QEMSKLSNPK IPVYINICSI
     DcbF   EFQKIHNERK FNELKEIFSF PRIHDALPIS KEMSKLSNPK IPVYINICSI
Consensus   eFQkiHNErk .n#lK#iFsF PRIhDALP!s kEMSKLSNPK IPVYINICSI 401                                                        450
     pmHS   PSRIKQLQYT IGVLKNQCDH FHIYLDGYPE VPDFIKKLGN KATVINCQNK
     pglA   PSRIAQLRRI IGILKNQCDH FHIYLDGYVE IPDFIKNLGN KATVVHCKDK
     DcbF   PSRIKQLQYT IGVLKNQCDH FHIYLDGYPE VPDFIKKLGN KATVINCQNK
Consensus   PSRIkQLqyt IG!LKNQCDH FHIYLDGYpE !PDFIKkLGN KATV!nCq#K 451                                                        500
     pmHS   NESIRDNGKF ILLEKLIKEN KDGYYITCDD DIRYPADYTN TMIKKINKYN
     pglA   DNSIRDNGKF ILLEELIEKN QDGYYITCDD DIIYPSDYIN TMIKKLNEYD
     DcbF   NESIRDNGKF ILLEKLIKEN KDGYYITCDD DIRYPADYIN TMIKKINKYN
Consensus   ##SIRDNGKF ILLEkLIkeN kDGYYITCDD DIrYPaDYiN TMIKKiNkY#

501                                                        550
     pmHS   DKAAIGLHGV IFPSRVNKYF SSDRIVYNFQ KPLENDTAVN ILGTGTVAFR
     pglA   DKAVIGLHGI LFPSRMTKYF SADRLVYSFY KPLEKDKAVN VLGTGTVSFR
     DcbF   DKAAIGLHGV IFPSRVNKYF SSDRIVYNFQ KTFRK..... ..........
Consensus   DKAaIGLHG! iFPSRvnKYF SsDRiVYnFq Kplekd.avn .lgtgtv.fr 551                                                        600
     pmHS   VSIFNKFSLS DFEHPGMVDI YFSILCKKNN ILQVCISRPS NWLTEDNKNT
     pglA   VSLFNQFSLS DFTHSGMADI YFSLLCKKNN ILQICISRPA NWLTEDNRDS
     DcbF   .......... .......... .......... .......... ..........
Consensus   vs.fn.fsls df.h.gm.di yfs.lckknn ilq.cisrp. nwltedn...

601                                                        650
     pmHS   ETLFHEFQNR DEIQSKLIIS NNPWGYSSIY PLLNNNANYS ELIPCLSFYN
     pglA   ETLYHQYRDN DEQQTQLIME NGPWGYSSIY PLVKNHPKFT DLIPCLPFYF
     DcbF   .......... .......... .......... .......... ..........
Consensus   etl.h..... de.q..li.. n.pwgyssiy pl..n..... .lipcl.fy.

651
     pmHS   E
     pglA   L
     DcbF   .
Consensus   .
```

HEPARIN/HEPAROSAN SYNTHASE FROM *P. MULTOCIDA* AND METHODS OF MAKING AND USING SAME

CROSS-REFERENCE TO RELATED APPLICATIONS

This application is a divisional of U.S. Ser. No. 10/142,143, filed May 8, 2002, now U.S. Pat. No. 7,307,159, issued Dec. 11, 2007; which claims priority under 35 U.S.C. §119(e) of provisional applications U.S. Ser. No. 60/289,554, filed May 8, 2001; U.S. Ser. No. 60/296,386, filed Jun. 6, 2001; U.S. Ser. No. 60/303,691, filed Jul. 6, 2001; and U.S. Ser. No. 60/313,258, filed Aug. 17, 2001. The entire contents of each of the above-referenced patent applications are hereby expressly incorporated herein by reference.

STATEMENT REGARDING FEDERALLY FUNDED RESEARCH

The government owns certain rights in and to this application pursuant to a grant from the National Science Foundation (NSF), Grant No. MCB-9876193.

BACKGROUND OF THE INVENTION

1. Field of the Invention

The presently claimed and disclosed invention relates, in general, to dual action heparin synthases and, more particularly, to dual action heparin synthases obtained from *Pasteurella multocida*. The presently claimed and disclosed invention also relates to heparosan, heparin and heparin-like molecules produced according to recombinant techniques and methods of using such molecules. The presently claimed and disclosed invention also relates to methods, and molecules produced according to such methods, for using the presently claimed and disclosed heparosan and/or heparin synthases for polymer grafting and the production of non-naturally occurring chimeric polymers incorporating stretches of one or more acidic GAG molecules, such as heparin, chondroitin, hyaluronan, and/or heparosan.

2. Background Information Relating to this Application

Glycosaminoglycans [GAGs] are long linear polysaccharides consisting of disaccharide repeats that contain an amino sugar and are found in most animals. Chondroitin [$\beta(1,4)$GlcUA-$\beta(1,3)$GalNAc]$_n$, heparin/heparosan ($\beta1,4$)GlcUA-[$\alpha(1, 4)$GlcNAc]$_n$, and hyaluronan [$\beta(1,4)$GlcUA-$\beta(1,3)$GlcNAc]$_n$ are the three most prevalent GAGs found in humans and are also the only known acidic GAGs. Chondroitin and heparin typically have n=20 to 100, while hyaluronan typically has n=$10^3$. Chondroitin and heparin are synthesized as glycoproteins and are sulfated at various positions in vertebrates. Hyaluronan is not sulfated in vertebrates. A substantial fraction of the GlcUA residues of heparin and chondroitin are epimerized to form iduronic acid. A simplified nomenclature has been developed for these GAGs. For example, heparin/heparosan's structure is noted as $\beta$4-GlcUA-$\alpha$4-GlcNAc.

The capsular polysaccharide produced by the Type D strain of *Pasteurella multocida* is N-acetyl heparosan (heparosan is unmodified heparin—i.e., sulfation or epimerization have not occurred). In vertebrates, one or more modifications including O-sulfation of certain hydroxyls, deacetylation and subsequent N-sulfation, or epimerization of glucuronic acid to iduronic acid modifies the precursor N-acetyl heparosan to heparin/heparan. Hereinafter, for convenience and/or ease of discussion, heparin and/or heparosan are defined as polymers having the $\beta$4GlcUA-$\alpha$4GlcNAc backbone.

Many lower animals possess these same GAGs or very similar molecules. GAGs play both structural and recognition roles on the cell surface and in the extracellular matrix. By virtue of their physical characteristics, namely a high negative charge density and a multitude of polar hydroxyl groups, GAGs help hydrate and expand tissues. Numerous proteins bind selectively to one or more of the GAGs. Thus the proteins found on cell surfaces or the associated extracellular matrices (e.g., CD44, collagen, fibronectin) of different cell types may adhere or interact via a GAG intermediate. Also GAGs may sequester or bind certain proteins (e.g., growth or coagulation factors) to cell surfaces.

Certain pathogenic bacteria produce an extracellular polysaccharide coating, called a capsule, which serves as a virulence factor. In a few cases, the capsule is composed of GAG or GAG-like polymers. As the microbial polysaccharide is identical or very similar to the host GAG, the antibody response is either very limited or non-existent. The capsule is thought to assist in the evasion of host defenses such as phagocytosis and complement. Examples of this clever strategy of molecular camouflage are the production of an authentic HA polysaccharide by Gram-negative Type A *Pasteurella multocida* and Gram-positive Group A and C *Streptococcus*. The HA capsule of these microbes increases virulence by $10^2$ to $10^3$-fold as measured by LD$_{50}$ values, the number of colony forming units that will kill 50% of the test animals after bacterial challenge.

The invasiveness and pathogenicity of certain *E. coli* strains has also been attributed to their polysaccharide capsules. Two *Escherichia coli* capsular types, K4 and K5, make polymers composed of GAG-like polymers. The *E. coli* K4 polymer is an unsulfated chondroitin backbone decorated with fructose side-branches on the C3 position of the GlcUA residues. The K5 capsular material is a polysaccharide, called heparosan, identical to mammalian heparin except that the bacterial polymer is unsulfated and there is no epimerization of GlcUA to iduronic acid.

The studies of GAG biosynthesis have been instrumental in understanding polysaccharide production in general. The HA synthases were the first GAG glycosyltransferases to be identified at the molecular level. These enzymes utilize UDP-sugar nucleotide substrates to produce large polymers containing thousands of disaccharide repeats. The genes encoding bacterial, vertebrate, and viral HAS enzymes have been cloned. In all these cases, expression studies have demonstrated that transformation with DNA encoding a single HAS polypeptide conferred the ability of foreign hosts to synthesize HA. Except for the most recent HAS to be identified, *P. multocida* pmHAS, these proteins have similar amino acid sequences, repeating conserved amino acid motifs, and predicted topology in the membrane. Likewise, as presently disclosed and claimed herein, heparosan and/or heparin synthases have been identified that confer upon a foreign host the ability to produce heparin.

With respect to related microbial GAG synthases other than the HASs, the *E. coli* K5 heparin glycosyltransferases, KfiA (SEQ ID NO:7) and KfiC (SEQ ID NO:8), have been identified by genetic and biochemical means. These K5 glycosyltransferases synthesize heparosan (unsulfated and unepimerased heparin) in vivo. The KfiA and KfiC require KfiB (SEQ ID NO:9), an accessory protein, with unknown function in order to synthesize heparosan, however. In vitro, the reactions are limited to adding one or two sugars; as such, it appears that some co-factor or reaction condition is missing—thus, extended polymerization does not occur in vitro when KfiA, KfiB, and KfiC are used. As such, the presently claimed and disclosed heparosan/heparin synthases provide a novel heretofore unavailable means for recombinatly producing heparin (the sulfated and epimerized molecule). In contrast to the HASs, the pmCS chondroitin synthase(s), and the presently disclosed and claimed heparin synthases, it appears that K5 requires two proteins, KfiA and KfiC, to transfer the sugars of the disaccharide repeat to the growing polymer chain. The presently claimed and disclosed heparin synthases (designated "pmHS and PgIA") are dual action enzymes capable of transferring both sugars of the growing heparin polymer chain. These enzymes polymerize heparosan in vivo and in vitro.

Many *P. multocida* isolates produce GAG or GAG-like molecules as assessed by enzymatic degradation and removal of the capsule of living bacterial cells. Type A *P. multocida*, the major fowl cholera pathogen, makes a capsule that is sensitive to hyaluronidase. Subsequent NMR structural studies of capsular extracts confirmed that HA was the major polysaccharide present. A specific HA-binding protein, aggrecan, also interacts with HA from Type A *P. multocida*. Two other distinct *P. multocida* types, a swine pathogen, Type D, and a minor fowl cholera pathogen, Type F, produce polymers that are chondroitin or chondroitin-like based on the observation that their capsules are degraded by *Flavobacterium* chondroitin AC lyase. After enzymatic removal of the capsule, both types were more readily phagocytosed by neutrophils in vitro. The capsule of Type D cells, but not Type F cells, also appear to be degraded by heparinase III, indicating that a heparin-type molecule is present as well.

Heparin acts as an anticoagulant and is used to avoid coagulation problems during extra corporal circulation and surgery as well as for treatment after thrombosis has been diagnosed. Heparin is used in the prevention and/or treatment of deep venous thrombosis, pulmonary embolism, mural thrombus after myocardial infarction, post thrombolytic coronary rethrombosis, unstable angina, and acute myocardial infarction. In addition to use as a treatment for various medical conditions, heparin is also used to coat medical instruments and implants, such as stents, to prevent blood clotting. Using heparin to coat various medical items eliminates the need to prescribe anti-clotting medication in some cases.

Where heparin is used to treat medical conditions as those described above, two different methods and two different types of heparin are used. The two methods are intravenous infusion of standard heparin and injection of low molecular mass heparin. Patients undergoing intravenous infusion are hospitalized and the activated partial thromoplastin time (aPTT) is monitored. This type of treatment requires that the patient remain hospitalized until warfarin is administered to achieve an International Normalized Ratio (INR) between 2.0 and 3.0 often resulting in a three to seven day hospital stay. The alternative treatment involves twice daily injections of low-molecular-weight heparin. The injection treatment allows the patient to self-administer or have a visiting nurse or family member administer the injections.

Low molecular weight heparin has a molecular weight of 1,000 to 10,000 Daltons as compared to the molecular weight of standard heparin of 5,000 to 30,000 Daltons. Low molecular weight heparin binds less strongly to protein than standard heparin, has enhanced bioavailability, interacts less with platelets and yields more predictable blood levels. The predictability of blood levels eliminates the need to monitor the aPPT. In addition, low molecular weight heparin offers a lower likelihood of bleeding and no reports of thrombocytopenia or osteoporosis have been issued with respect to low molecular weight heparin.

In the presently claimed and disclosed invention, the monosaccharide composition of the *P. multocida* Type D polysaccharide has been identified and analyzed. The DNA sequence information of the Type A HA biosynthesis locus and the Type F biosynthesis locus allowed for the prediction of the general properties of the Type D locus. From this information on potential precursor genes required by a heparin synthase, pmHS was identified (*P. multocida* Heparin Synthase), the first dual action microbial heparin synthase to be identified and molecularly cloned from any source. With respect to the pmHS, a single polypeptide is responsible for the copolymerization of the GlcUA and GlcNAc sugars—i.e., it is a dual action enzyme as opposed to the single action nature of the at least three enzymes of *E. coli* K5 heparosan biosynthesis locus that are required for heparin production. The identification of pmHS also allowed for the identification of the existence of another heparin synthase found in Type A, D and F *P. multocida*. A gene with unknown function, called PgIA, was found in a genome sequencing project of Type A *P. multocida*; no enzymatic function (or any function) has been previously described with respect to this PgIA gene. Hereinafter, and is contemplated and included within the presently disclosed and claimed invention, is disclosed that the PgIA enzyme, which is 70% identical to pmHS, is also a heparin synthase. This unexpected cryptic gene is functional in vitro in recombinant systems. The Type D capsular polymer has been identified as a heparin polymer. Organisms with the heparin synthase gene (Type D *P. multocida*) as new sources of heparin polymer have also been identified, purified, and characterized.

SUMMARY OF THE INVENTION

The presently claimed and disclosed invention relates, in general, to dual action heparin synthases and, more particularly, to dual action heparin synthases obtained from *Pasteurella multocida*. The presently claimed and disclosed invention also relates to heparosan, heparin and heparin-like molecules produced according to recombinant techniques and methods of using such molecules. The presently claimed and disclosed invention also relates to methods, and molecules produced according to such methods, for using the presently claimed and disclosed heparosan and/or heparin synthases for polymer grafting and the production of non-naturally occurring chimeric polymers incorporating stretches of one or more acidic GAG molecules, such as heparin, chondroitin, hyaluronan, and/or heparosan.

BRIEF DESCRIPTION OF THE SEVERAL VIEWS OF THE DRAWINGS

FIG. 4(A-D) graphically depicts the alignment of the pmHS (two clones: A2, B10) with PgIA, KfiA, KfiC, and DcbF. pmHS is shown in various forms: HSA1 and HSA2 are the two putative domains of pmHS; pORF=partial open reading frame which was obtained before complete sequence determined; recon=reconstructed open reading frame with sequence from multiple sources. FIG. 4A: KfiC, SEQ ID NO:29; HSA1, SEQ ID NO:30; KfiA, SEQ ID NO:7; HSA2, SEQ ID NO:31; Consensus, SEQ ID NO:32. FIG. 4B: pmHS, SEQ ID NO:2; pgIA, SEQ ID NO:6; DcbF, SEQ ID NO:17; Consensus, SEQ ID NO:33. FIG. 4C: A2, SEQ ID NO:2; B10, SEQ ID NO:4; pgIA, SEQ ID NO:6; DcbF, SEQ ID NO:17; Consensus, SEQ ID NO:34. FIG. 4D: pmHS, SEQ ID NO:2; pgIA, SEQ ID NO:6; DcbF, SEQ ID NO:17; and Consensus, SEQ ID NO:35.

DETAILED DESCRIPTION OF THE INVENTION

Figure 1:
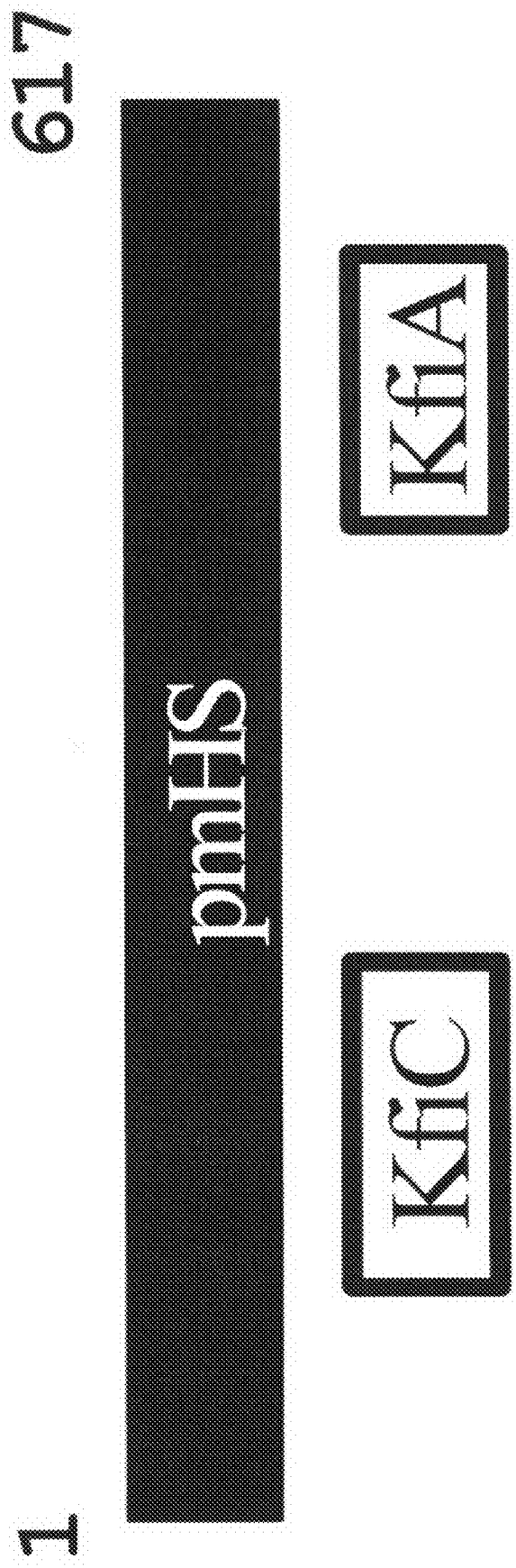
FIG. 1 graphically depicts Sequence Similarity of pmHS with KfiA and KfiC. Elements of the *Pasteurella* heparosan synthase, HS1 (containing residues 91-240SEQ ID NO: 23) and HS2 (containing residues 441-540; SEQ ID NO:26) are very similar to portions of two proteins from the *E. coli* K5 capsular locus (A, residues 75-172 of KfiA, SEQ ID NO:27 ; C, residues 262-410 of KfiC, SEQ ID NO:24) as shown by this modified Multalin alignment (ref. 21; numbering scheme corresponds to the pmHS sequence). The HS1 and HS2 elements may be important for hexosamine transferase or for glucuronic acid transferase activities, respectively. (con, consensus symbols: asterisks, [K or R] and [S or T]; %, any one of F,Y,W; $, any one of L,M; !, any one of I,V; #, any one of E,D,Q,N). The consensus sequence of the alignment of HS1 and KfiC has been assigned SEQ ID NO:25, while the consensus sequence of the alignment of HS2 and KfiA is assigned SEQ ID NO:28.
Figure 2:
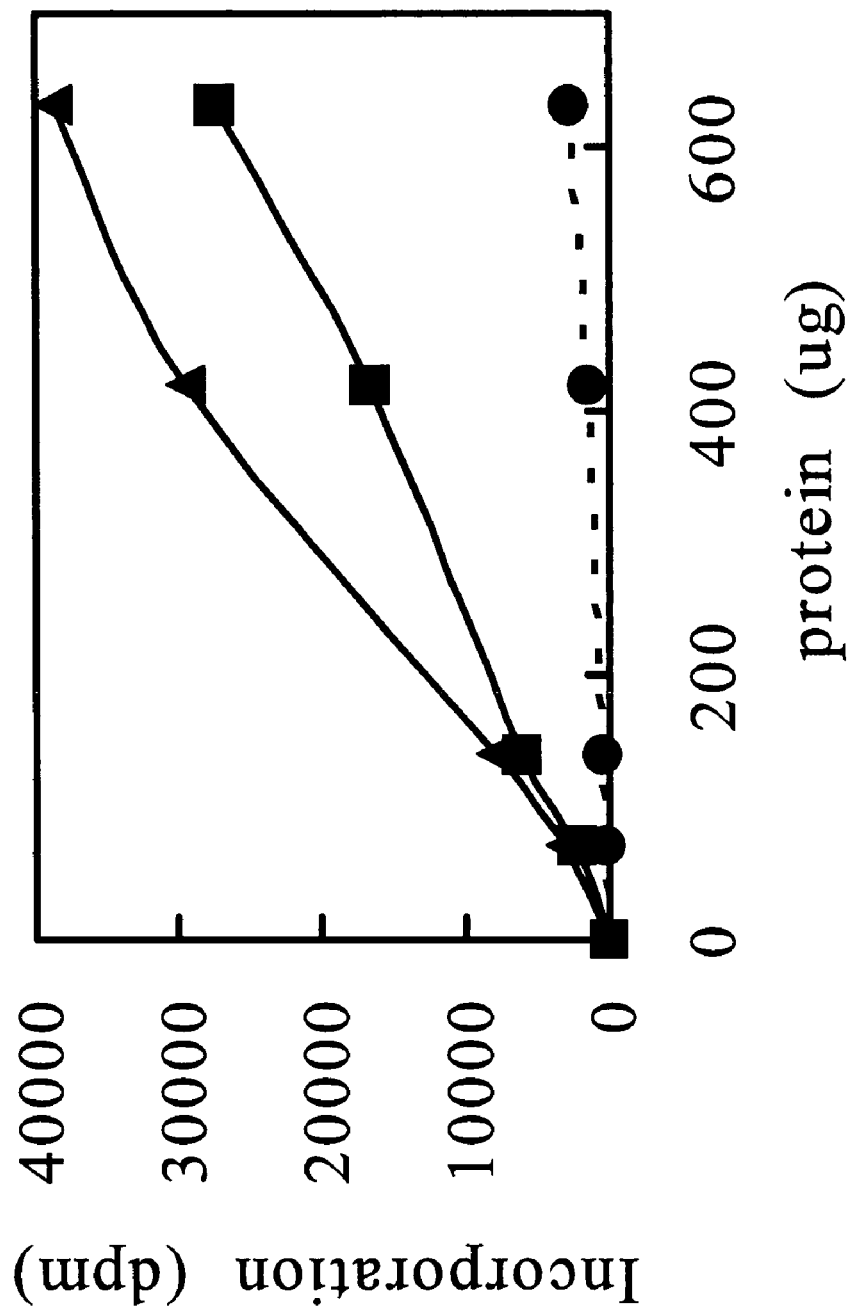
FIG. 2 depicts pmHS Activity Dependence on Acceptor and Enzyme Concentration. Various amounts of crude membranes containing the full-length enzyme, pmHS1-617, were incubated in 50 µl of buffer containing 50 mM Tris, pH 7.2, 10 mM $MgCl_2$, 10 mM $MnCl_2$, 500 µM UDP-[$^{14}$C]GlcUA (0.15 µCi), and 500 µM UDP-GlcNAc. Three parallel sets of reactions were performed with either no acceptor (circles) or two concentrations of heparosan polymer acceptor (uronic acid: 0.6 µg, squares; 1.7 µg, triangles). After 40 min, the reaction was terminated and analyzed by paper chromatography. The background incorporation due to vector membranes alone (630 µg total protein; not plotted) with the high concentration of acceptor was 75 dpm [$^{14}$C]GlcUA. The activity of pmHS is greatly stimulated by exogenous acceptor.
Figure 3:
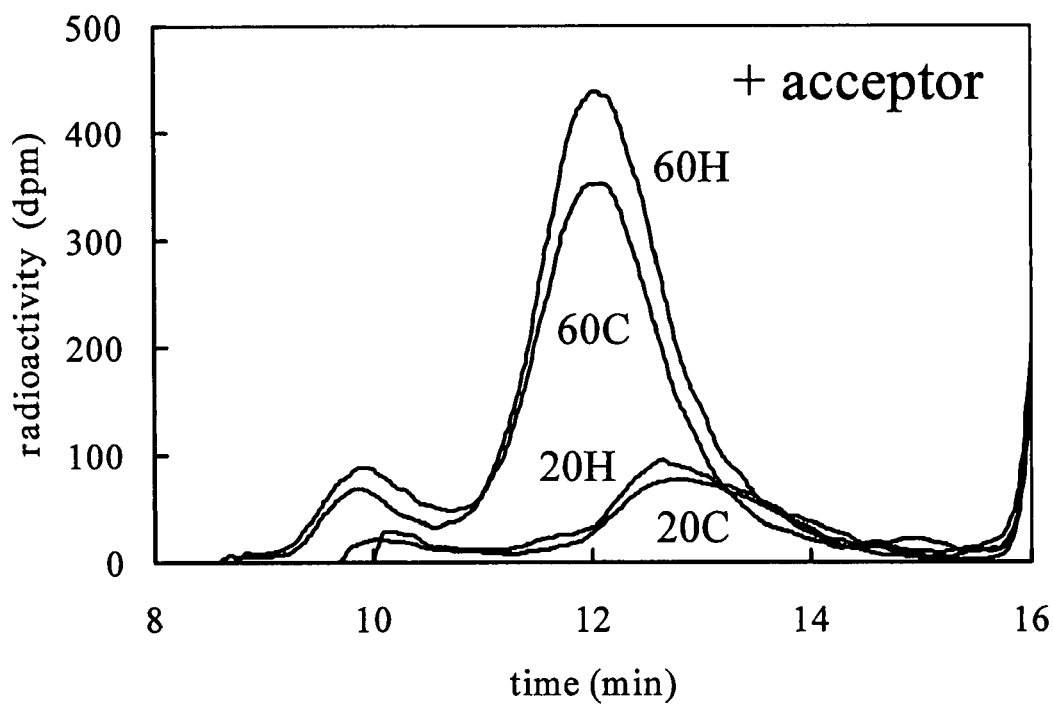
FIG. 3 Gel Filtration Analysis of Radiolabeled Polymer Synthesized in vitro. The crude membranes containing pmHS (0.7 mg total protein) were incubated with UDP-[$^{14}$C]GlcUA and UDP-[$^3$H]GlcNAc (each 500 µM, 0.4 µCi) in a 200 µl reaction volume either in the presence (top panel) or absence (bottom panel) of acceptor polymer (1 µg uronic acid). After various reaction times (denoted on curves: 20, 60, or 270 min), portions of the samples (75%) were analyzed on the PolySep column (calibration elution times in minutes: void volume, 9.8; 580 kDa dextran, 12.3; 145 kDa dextran, 12.75, totally included volume, 16.7). The starting acceptor polymer eluted at 12.8 min. Large polymers composed of both radio-labeled sugars ($^{14}$C, C; $^3$H, H) in an equimolar ratio were synthesized by pmHS.
Figure 3:
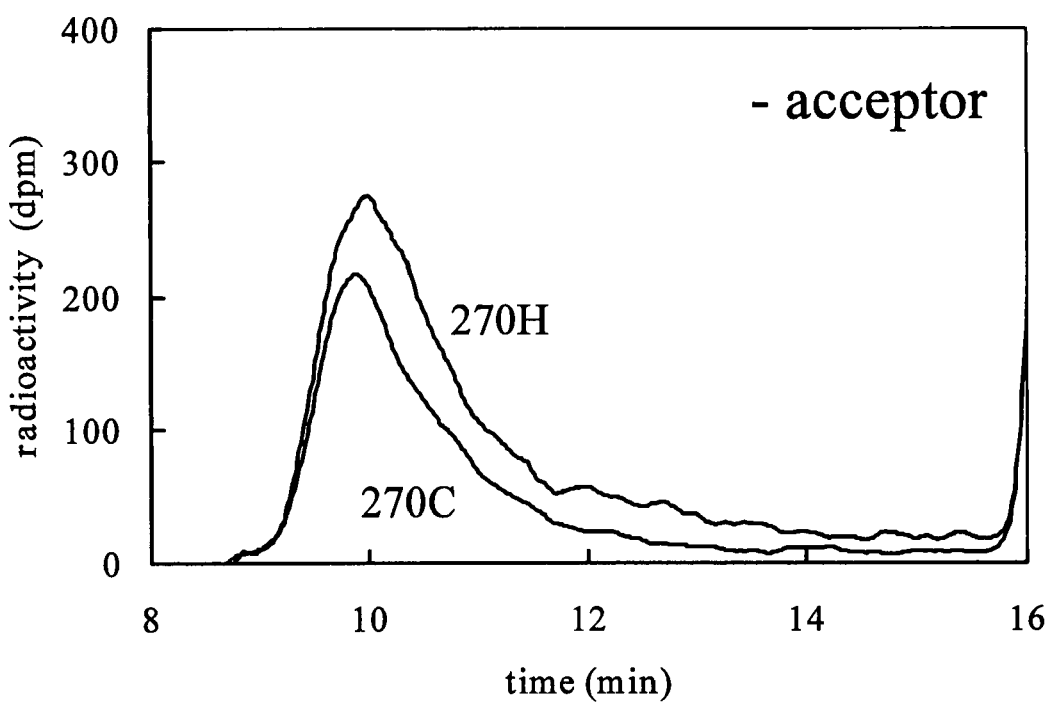

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Heparin Synthase ("HS") coding sequence yet is isolated away from, or purified free from, unrelated genomic DNA, for example, total *Pasteurella multocida* or, for example, mammalian host genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified pmHS (*Pasteurella multocida* Heparin Synthase) gene or a PgIA gene refers to a DNA segment including HS coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case pmHS or PgIA, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the HS genes from *Pasteurella multocida*. One such advantage is that, typically, eukaryotic enzymes may require significant post-translational modifications that can only be achieved in an eukaryotic host. This will tend to limit the applicability of any eukaryotic HS genes that are obtained. Additionally, such eukaryotic HS genes are dainty, fragile, and difficult, if not impossible, to transfer into prokaryotic hosts for large scale polymer production. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library; and (b) the ease of manipulation because the overall size of the coding region of a prokaryotic gene is significantly smaller due to the absence of introns. Furthermore, if the product of the HS genes (i.e., the enzyme) requires posttranslational modifications or cofactors, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode a HS gene such as pmHS or PgIA. In the case of pmHS, the isolated DNA segments and recombinant vectors incorporating DNA sequences which include within their amino acid sequences an amino acid sequence in accordance with SEQ ID NO:2 or SEQ ID NO:4; for PgIA, an amino acid sequence in accordance with SEQ ID NO: 6. Moreover, in other particular embodiments, the invention concerns isolated DNA segments and recombinant vectors incorporating DNA sequences which encode a gene that includes within its amino acid sequence the amino acid sequence of an HS gene or DNA, and in particular to a HS gene or cDNA, corresponding to *Pasteurella multocida* Heparin Synthases—pmHS and PgIA. For example, where the DNA segment or vector encodes a full length HS protein, or is intended for use in expressing the HS protein, preferred sequences are those which are essentially as set forth in SEQ ID NO:2 or SEQ ID NO:4 or SEQ ID NO:6. Additionally, sequences which have at least one or more amino acid motifs (discussed in detail hereinafter) and encode a functionally active heparosan/heparin synthase are contemplated for use.

The presently claimed and disclosed pmHS includes SEQ ID NOS:1 and 3 (nucleotide sequence) and SEQ ID NOS:2 and 4 (amino acid sequences) that have been assigned GenBank Accession Nos. AAL84702 and AAL84705, respectively. The presently claimed and disclosed PglA includes SEQ ID NO:5 (nucleotide sequence) and SEQ ID NO:6 (amino acid sequence) that have been assigned GenBank Accession No. NP_245351. Amino acid motifs for enzymatically active heparosan/heparin synthases are disclosed in detail hereinafter.

Nucleic acid segments having heparin synthase activity may be isolated by the methods described herein. The term "a sequence essentially as set forth in SEQ ID NO:2 or 4 or 6" means that the sequence substantially corresponds to a portion of SEQ ID NO:2 or 4 or 6 and has relatively few amino acids which are not identical to, or a biologically functional equivalent of, the amino acids of SEQ ID NO:2 or 4 or 6. The term "biologically functional equivalent" is well understood in the art and is further defined in detail herein, as a gene having a sequence essentially as set forth in SEQ ID NO:2 or 4 or 6, and that is associated with the ability of prokaryotes to produce heparin/heparosan or a "heparin like" polymer or a heparin synthase polypeptide. For example, PglA is approximately 70% identical to pmHS and PglA is shown, hereinafter, to be an enzymatically active heparin/heparosan synthase.

One of ordinary skill in the art would appreciate that a nucleic acid segment encoding enzymatically active heparin synthase may contain conserved or semi-conserved substitutions to the sequences set forth in SEQ ID NOS: 1, 2, 3, 4, 5 or 6 and yet still be within the scope of the invention.

In particular, the art is replete with examples of practitioner's ability to make structural changes to a nucleic acid segment (i.e., encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019-1029 (1988) [" . . . according to the observed exchangeability of amino acid side chains, only four groups could be delineated; (i) Ile and Val; (ii) Leu and Met, (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns . . . " Compatible changes can be made]. Each of these articles, to the extent that they provide additional details to one of ordinary skill in the art in the methods of making such conserved or semi-conserved amino acid substitutions, are hereby expressly incorporated herein in their entirety as though set forth herein.

These references and countless others available to one of ordinary skill in the art, indicate that given a nucleic acid sequence, one of ordinary skill in the art could make substitutions and changes to the nucleic acid sequence without changing its functionality. Also, a substituted nucleic acid segment may be highly identical and retain its enzymatic activity with regard to its unadulterated parent, and yet still fail to hybridize thereto (i.e., spHAS and seHAS, 70% identical yet do not hybridize under standard hybridization conditions as defined hereinafter). Therefore, the ability of two sequences to hybridize to one another can be a starting point for comparison but should not be the only ending point—rather, one of ordinary skill in the art must look to the conserved and semi-conserved amino acid stretches between the sequences between the sequences and also must assess functionality. Thus, given that two sequences may have conserved and/or semi-conserved amino acid stretches, functionality must be assessed.

One of ordinary skill in the art would also appreciate that substitutions can be made to the pmHS nucleic acid segment listed in SEQ ID NO: 1 or 3 tha do not affect the amino acid sequences they encode or result in conservative or semi-conservative substitutions in the amino acid sequences they encode without deviating outside the scope and claims of the present invention. Standardized and accepted functionally equivalent amino acid substitutions are presented in Table I.

TABLE I

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Serine, Threonine, Cysteine, Asparagine, Glutamine |
| Negatively Charged R Groups | Aspartic Acid, Glutamic Acid |
| Positively Charged R Groups | Lysine, Arginine, Histidine |

A particular example would be SEQ ID NO NOS: 2 and 4, both of which encode a functionally active HS and yet have a single substitution at position 455 (Threonine for Isoleucine), and yet both enzymes are still capable of producing heparosan. Such a conservative or semi-conservative scheme is even more evident when comparing pmHS with PglA—they are only ~70% identical and yet still both produce functionally active HS enzymes.

Another preferred embodiment of the present invention is a purified nucleic acid segment that encodes a protein in accordance with SEQ ID NO:2 or 4 or 6 further defined as a recombinant vector. As used herein, the term "recombinant vector" refers to a vector that has been modified to contain a nucleic acid segment that encodes a HS protein, or fragment thereof. The recombinant vector may be further defined as an expression vector comprising a promoter operatively linked to said HS encoding nucleic acid segment.

A further preferred embodiment of the present invention is a host cell, made recombinant with a recombinant vector comprising a HS gene. The preferred recombinant host cell may be a prokaryotic cell. In another embodiment, the recombinant host cell is an eukaryotic cell. As used herein, the term "engineered" or "recombinant" cell is intended to refer to a cell into which a recombinant gene, such as a gene encoding HS, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, one or more copies of a genomic gene, or will include genes positioned adjacent to a promoter not naturally associated with the particular introduced gene.

Where one desires to use a host other than *Pasteurella*, as may be used to produce recombinant heparin/heparosan synthase, it may be advantageous to employ a prokaryotic system such as *E. coli, B. subtilis, Lactococcus sp.*, (see, for example, U.S. patent application Ser. No. 09/469,200, which discloses the production of HA through the introduction of a HAS gene into *Bacillus* host—the contents of which are expressly incorporated herein in their entirety), or even eukaryotic systems such as yeast or Chinese hamster ovary, African green monkey kidney cells, VERO cells, or the like. Of course, where this is undertaken it will generally be desirable to bring the heparin/heparosan synthase gene under the control of sequences which are functional in the selected alternative host. The appropriate DNA control sequences, as well as their construction and use, are generally well known in the art as discussed in more detail hereinbelow.

In preferred embodiments, the heparin/heparosan synthase-encoding DNA segments further include DNA sequences, known in the art functionally as origins of replication or "replicons", which allow replication of contiguous sequences by the particular host. Such origins allow the preparation of extrachromosomally localized and replicating chimeric segments or plasmids, to which HS DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HS coding gene sequence together with an appropriate replication origin and under the control of selected control regions.

Thus, it will be appreciated by those of ordinary skill in the art that other means may be used to obtain the HS gene or cDNA, in light of the present disclosure. For example, polymerase chain reaction or RT-PCR produced DNA fragments may be obtained which contain full complements of genes or cDNAs from a number of sources, including other strains of *Pasteurella* or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HS, and in a more preferred embodiment, the isolated nucleic acids should encode an amino acid sequence that contains at least one of the HS amino acid motifs described in detail hereinafter.

Once the DNA has been isolated it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* or *P. multocida* are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade *Lactococcus* or *Bacillus* strain for production of heparin/heparosan. These are benign and well studied organisms used in the production of certain foods and biotechnology products—otherwise known in the art as GRAS (Generally Regarded As Safe). GRAS organisms are advantageous in that one can augment the *Lactococcus* or *Bacillus* strain's ability to synthesize heparin/heparosan through gene dosaging (i.e., providing extra copies of the HA synthase gene by amplification) and/or the inclusion of additional genes to increase the availability of the heparin/heparosan precursors UDP-GlcUA and UDP-GlcNAc and/or the inclusion of genes that include enzymes that will make modifications (such as sulfation and epimerization) to the heparosan polymer in order to convert it to heparin. Sugar precursors are made by the enzymes with UDP-glucose dehydrogenase and UDP-N-acetylglucosamine pyrophosphorylase activity, respectively. The inherent ability of a bacterium to synthesize heparin/heparosan is also augmented through the formation of extra copies, or amplification, of the plasmid that carries the heparin/heparosan synthase gene. This amplification can account for up to a 10-fold increase in plasmid copy number and, therefore, the HS gene copy number.

Another procedure that would further augment HS gene copy number is the insertion of multiple copies of the gene into the plasmid. Another technique would include integrating the HS gene into chromosomal DNA. This extra amplification would be especially feasible, since the HS gene size is small. In some scenarios, the chromosomal DNA-ligated vector is employed to transfect the host that is selected for clonal screening purposes such as *E. coli* or *Bacillus*, through the use of a vector that is capable of expressing the inserted DNA in the chosen host. In certain instances, especially to confer stability, genes such as the HS gene, may be integrated into the chromosome in various positions in an operative fashion. Unlike plasmids, integrated genes do not need selection pressure for maintenance of the recombinant gene.

Where an eukaryotic source such as dermal or synovial fibroblasts or rooster comb cells is employed, one will desire to proceed initially by preparing a cDNA library. This is carried out first by isolation of mRNA from the above cells, followed by preparation of double stranded cDNA and ligation of the cDNA with the selected vector. Numerous possibilities are available and known in the art for the preparation of the double stranded cDNA, and all such techniques are believed to be applicable. A preferred technique involves reverse transcription utilizing an enzyme having reverse transcriptase activity. Once a population of double stranded cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as λgt11, λgt12, λGem11, and/or λZAP for the cloning and expression screening of cDNA clones.

In certain other embodiments, the invention concerns isolated DNA segments and recombinant vectors that include within their sequence a nucleic acid sequence essentially as set forth in SEQ ID NO:1 or 3 or 5. The term "essentially as set forth in SEQ ID NO:1 or 3 or 5" is used in the same sense as described above with respect to the amino acid sequences and means that the nucleic acid sequence substantially corresponds to a portion of SEQ ID NO:1 or 3 or 5, and has relatively few codons that are not identical, or functionally equivalent, to the codons of SEQ ID NO:1 or 3 or 5 and encodes a enzymatically active HS. The term "functionally equivalent codon" is used herein to refer to codons that encode the same amino acid, such as the six codons for arginine or serine, and also refers to codons that encode biologically equivalent amino acids. "Biologically Equivalent Amino Acids" of Table I refers to residues that have similar chemical or physical properties that may be easily interchanged for one another.

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzymatic activity is concerned. The addition of terminal sequences particularly applies to nucleic acid sequences which may, for example, include various non-coding sequences flanking either of the 5' or 3' portions of the coding region or may include various internal sequences, which are known to occur within genes.

Likewise, deletion of certain portions of the polypeptide can be desirable. For example, functional truncated versions of pmHAS, the *Pasteurella* hyaluronan synthase, missing the carboxyl terminus enhances the utility for in vitro use. The truncated pmHAS enzyme is a soluble protein that is easy to purify in contrast to the full-length protein (972 residues). Also, expression level of the enzyme increases greatly as the membrane is not overloaded. It is also contemplated that a truncated version of pmHS would also be useful and is contemplated as falling within the scope of the presently claimed and disclosed invention. Such a truncated version would also be highly soluble and increase expression of the enzyme; the native membrane proteins are found in low levels and are not soluble without special treatment with detergents.

Allowing for the degeneracy of the genetic code as well as conserved and semi-conserved substitutions, sequences which have between about 40% and about 80%; or more preferably, between about 80% and about 90%; or even more preferably, between about 90% and about 99% of nucleotides which are identical to the nucleotides of SEQ ID NO:1 or 3 or 5 will be sequences which are "essentially as set forth in SEQ ID NO:1 or 3 or 5". In a preferred embodiment, the sequences would be 70% identical. Sequences which are essentially the same as those set forth in SEQ ID NO:1 or 3 or 5 may also be functionally defined as sequences which are capable of hybridizing to a nucleic acid segment containing the complement of SEQ ID NO:1 or 3 or 5 under standard or less stringent hybridizing conditions. Suitable standard hybridization conditions will be well known to those of skill in the art and are clearly set forth hereinbelow. As certain domains and active sites are formed from a relatively small portion of the total polypeptide, these regions of sequence identity or similarity may be present only in portions of the gene. Additionally, sequences which are "essentially as set forth in SEQ ID NO:1 or 3 or 5" will include those amino acid sequences that have at least one of the amino acid motifs (described hereinafter in detail) and that also retain the functionality of an enzymatically active HS.

As is well known to those of ordinary skill in the art, most of the amino acids in a protein are present to form the "scaffolding" or general environment of the protein. The actual working parts responsible for the specific desired catalysis are usually a series of small domains or motifs. Thus, a pair of enzymes that possess the same or similar motifs would be expected to possess the same or similar catalytic activity, thus they are functionally equivalent. Utility for this hypothetical pair of enzymes may be considered interchangeable unless one member of the pair has a subset of distinct, useful properties. In a similar vein, certain non-critical motifs or domains may be dissected from the original, naturally occurring protein and function will not be affected; removal of non-critical residues does not perturb the important action of the remaining critical motifs or domains. By analogy, with sufficient planning and knowledge, it is possible to translocate motifs or domains from one enzyme to another polypeptide to confer the new enzyme with desirable characteristics intrinsic to the domain or motif. Such motifs for HS are disclosed in particularly hereinafter.

The term "standard hybridization conditions" as used herein, is used to describe those conditions under which substantially complementary nucleic acid segments will form standard Watson-Crick base-pairing. A number of factors are known that determine the specificity of binding or hybridization, such as pH, temperature, salt concentration, the presence of agents such as formamide and dimethyl sulfoxide, the length of the segments that are hybridizing, and the like. When it is contemplated that shorter nucleic acid segments will be used for hybridization, for example fragments between about 14 and about 100 nucleotides, salt and temperature preferred conditions for overnight standard hybridization will include 1.2-1.8×HPB (High Phosphate Buffer) at 40-50° C. or 5×SSC (Standard Saline Citrate) at 50° C. Washes in low salt (10 mM salt or 0.1×SSC) are used for stringent hybridizations with room temperature incubations of 10-60 minutes. Washes with 0.5× to 1×SSC, 1% Sodium dodecyl sulfate at room temperature are used in lower stringency washes for 15-30 minutes. For all hybridizations: (where 1×HPB=0.5 m NaCl, 0.1 m $Na_2HPO_4$, 5 mM EDTA, pH 7.0) and (where 20×SSC=3 m NaCl, 0.3 m Sodium Citrate with pH 7.0).

Naturally, the present invention also encompasses DNA segments which are complementary, or essentially complementary, to the sequence set forth in SEQ ID NOS:1, 2, 3, 4, 5, or 6. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1, 2, 3, 4, 5, or 6 under the above-defined standard hybridization conditions.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. For example, functional spHAS-$(Histidine)_6$ and x1 HAS1-(Green Fluorescent Protein) fusion proteins have been reported. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular nucleic acid and amino acid sequences of SEQ ID NOS:1, 2, 3, 4, 5, or 6. Recombinant vectors and isolated DNA segments may therefore variously include the HS coding regions themselves, coding regions bearing selected alterations or modifications in the basic coding region, or they may encode larger polypeptides which nevertheless include HS coding regions or may encode biologically functional equivalent proteins or peptides which have variant amino acid sequences.

The DNA segments of the present invention encompass biologically functional equivalent HS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HS protein or to test HS mutants in order to examine HS activity at the molecular level.

Also, specific changes to the HS coding sequence will result in the production of heparin/heparosan having a modified size distribution or structural configuration. One of ordinary skill in the art would appreciate that the HS coding sequence can be manipulated in a manner to produce an altered HS which in turn is capable of producing heparin/heparosan having differing polymer sizes and/or functional capabilities. The utility of such a modified polymer is easily appreciated from the above "Background of the Invention." For example, the HS coding sequence may be altered in such a manner that the HS has an altered sugar substrate specificity so that the HS creates a new heparin/heparosan-like chimeric polymer incorporating a different structure via the inclusion of a previously unincorporated sugar or sugar derivative. This newly incorporated sugar results in a modified heparin/heparosan having different and unique functional properties. As will be appreciated by one of ordinary skill in the art given the HS coding sequences, changes and/or substitutions can be made to the HS coding sequence such that these desired properties and/or size modifications can be accomplished.

Basic knowledge on the substrate binding sites (e.g., the UDP-GlcUA site or UDP-GlcNAc site or oligosaccharide acceptor site) of pmHS or pgIA allows the targeting of residues for mutation to change the catalytic properties of the site. The identity of important catalytic residues of pmHAS, another GAG synthase, have recently been elucidated (Jing & DeAngelis, 2000, Glycobiology vol 10; pp. 883-889 the contents of which are expressly incorporated herein in their entirety). Appropriate changes at or near these residues alters UDP-sugar binding. Changes of residues in close proximity should allow other precursors to bind instead of the authentic heparin/heparosan sugar precursors; thus a new, modified polymer is synthesized. Polymer size changes are caused by differences in the synthase's catalytic efficiency or changes in the acceptor site affinity. Polymer size changes have been made in seHAS and spHAS (U.S. patent application Ser. Nos. 09/559,793 and 09/469,200, the contents of which are expressly incorporated herein by reference) as well as the vertebrate HAS, xIHAS1 (DG42) (Pummill & DeAngelis, in press and which is also incorporated herein in its entirety) by mutating various residues. As pmHS is a more malleable, robust enzyme than these other enzymes, similar or superior versions of mutant pmHS or pgIA which synthesize modified polymers are easily produced.

The term "modified structure" as used herein denotes a heparin/heparosan polymer containing a sugar or derivative not normally found in the naturally occurring heparin/heparosan polypeptide. The term "modified size distribution" refers to the synthesis of heparin/heparosan molecules of a size distribution not normally found with the native enzyme; the engineered size could be much smaller or larger than normal.

One of ordinary skill in the art given this disclosure would appreciate that there are several ways in which the size distribution of the heparin/heparosan polymer made by the HS could be regulated to give different sizes. First, the kinetic control of product size can be altered by environmental factors such as decreasing temperature, decreasing time of enzyme action and/or by decreasing the concentration of one or both sugar nucleotide substrates. Decreasing any or all of these variables will give lower amounts and smaller sizes of heparin/heparosan product. The disadvantages of these extrinsic approaches are that the yield of product is also decreased and it is difficult to achieve reproducibility from day to day or batch to batch. Secondly, the alteration of the intrinsic ability of the enzyme to synthesize a large or small heparin/heparosan product. Changes to the protein are engineered by recombinant DNA technology, including substitution, deletion and addition of specific amino acids (or even the introduction of prosthetic groups through metabolic processing). Such changes that result in an intrinsically slower enzyme then allow for more reproducible control of heparin/heparosan size by kinetic means. The final heparin/heparosan size distribution is determined by certain characteristics of the enzyme that rely on particular amino acids in the sequence. Among the residues absolutely conserved between the now known HS enzymes, there is a set of amino acids at unique positions that control or greatly influence the size of the polymer that the enzyme can make.

Finally, using post-synthesis processing larger molecular weight heparin can be degraded with specific glycasidases or ultrasonication, acids or a combination thereof to make lower molecular weight heparin/heparosan. This practice, however, is very difficult to achieve reproducibility and one must meticulously repurify the heparin/heparosan to remove the cleavage reagent and unwanted digestion products.

Structurally modified heparin/heparosan is no different conceptually than altering the size distribution of the heparin/heparosan product by changing particular amino acids in the desired HS and/or more particularly, but not limiting thereto, pmHS or PgIA. Derivatives of UDP-GlcNAc, in which the acetyl group is missing from the amide (UDP-GlcN) or replaced with another chemically useful group (for example, phenyl to produce UDP-GlcNPhe), are expected to be particularly useful. The free amino group would be available for chemical reactions to derivatize heparin/heparosan in the former case with GlcN incorporation. In the latter case, GlcN-Phe, would make the polymer more hydrophobic or prone to making emulsions. The strong substrate specificity may rely on a particular subset of amino acids among the residues that are conserved. Specific changes to one or more of these residues creates a functional HS that interacts less specifically with one or more of the substrates than the native enzyme. This altered enzyme then utilizes alternate natural or special sugar nucleotides to incorporate sugar derivatives designed to allow different chemistries to be employed for the following purposes: (i) covalently coupling specific drugs, proteins, or toxins to the structurally modified heparin/heparosan for general or targeted drug delivery, radiological procedures, etc. (ii) covalently cross linking the heparin/heparosan itself or to other supports to achieve a gel, or other three dimensional biomaterial with stronger physical properties, and (iii) covalently linking heparin/heparosan to a surface to create a biocompatible film or monolayer.

EXPERIMENTAL

As stated hereinabove, Pasteurella multocida Type D, a causative agent of atrophic rhinitis in swine and pasteurellosis in other domestic animals, produces an extracellular polysaccharide capsule that is a putative virulence factor. It has been reported that the capsule of Type D was removed by treating microbes with heparin lyase III. A 617-residue enzyme, pmHS, and a 651-residue enzyme, PgIA, which are both authentic heparosan (unsulfated, unepimerized heparin) synthase enzymes have been molecularely cloned and are presently claimed and disclosed herein. Recombinant Escherichia coli-derived pmHS or PgIA catalyzes the polymerization of the monosaccharides from UDP-GlcNAc and UDP-GlcUA. Other structurally related sugar nucleotides do not substitute. Synthase activity was stimulated about 7- to 25-fold by the addition of an exogenous polymer acceptor. Molecules composed of ~500 to 3,000 sugar residues were produced in vitro. The polysaccharide was sensitive to the action of heparin lyase III but resistant to hyaluronan lyase. The sequence of pmHS enzyme is not very similar to the vertebrate heparin/heparan sulfate glycosyltransferases, EXT1/2, or to other Pasteurella glycosaminoglycan synthases that produce hyaluronan or chondroitin. Certain motifs do exist however, between the pmHS, pgIA, and KfiA and KfiC thereby leading to deduced amino acid motifs that are conserved throughout this class of GAG synthases for the production of heparin/heparosan The pmHS enzyme is the first microbial dual-action glycosyltransferase to be described that forms a polysaccharide composed of β4GlcUA-α4GlcNAc disaccharide repeats. In contrast, heparosan biosynthesis in E. coli K5 requires at least two separate polypeptides, KfiA and KfiC, to catalyze the same polymerization reaction.

Glycosaminoglycans [GAGs] are long linear polysaccharides consisting of disaccharide repeats that contain an amino sugar [1-2]. Heparin/heparan [β4GlcUA-α4GlcNAc]$_n$, chondroitin [β4GlcUA-β3GalNAc]$_n$, and hyaluronan [β4GlcUA-β3GlcNAc]$_n$ are three prevalent GAGs and the only known acidic GAGs. In the former two polymers, usually n=20 to 100 while in the case of HA, typically n=10³-4. In vertebrates, one or more modifications including O-sulfation of certain hydroxyls, deacetylation and subsequent N-sulfation, or epimerization of glucuronic acid to iduronic acid are found in most GAGs except HA[3]. A few clever microbes also produce GAG chains, however, sulfation or epimerization have not been described. The GAGs in pathogenic bacteria are found as extracellular polysaccharide coatings, called capsules, which serve as virulence factors[4]. The capsule is thought to assist in the evasion of host defenses such as phagocytosis and complement. As the microbial polysaccharide is identical or very similar to the host GAG, the antibody response is either very limited or non-existent.

The invasiveness and pathogenicity of certain Escherichia coli strains has been attributed to their polysaccharide capsule[4]. Two E. coli capsular types, K5 and K4, make polymers composed of GAG-like polymers. The K5 capsular material is a polysaccharide called heparosan, N-acetylheparosan, or desulfoheparin, which are identical to mammalian heparin/ heparin sulfate except that the bacterial polymer is unsulfated and there is no epimerization of GlcUA to iduronic acid[5].

The E. coli K4 polymer is an unsulfated chondroitin backbone decorated with fructose side-branches on the C3 position of the GlcUA residues[6].

The E. coli K5 capsule biosynthesis locus contains the open reading frames KfiA-D (also called Kfa in some reports; GenBank Accession Number X77617). At first, KfiC was stated to be a dual-action glycosyltransferase responsible for the alternating addition of both GlcUA and GlcNAc to the heparosan chain[7]. However, a later report by the same group reported that another protein, KfiA, was actually the αGlcNAc-transferase required for Heparosan polymerization[8]. Therefore, at least these two enzymes, KfiA and KfiC, the βGlcUA-transferase, work in concert to form the disaccharide repeat and the first report, that KfiC was a dual-action enzyme, was in error. Another deduced protein in the operon, KfiB, was suggested to stabilize the enzymatic complex during elongation in vivo, but perhaps not participate directly in catalysis[8]. The identity and the sequence of the E. coli K4 capsular glycosyltransferase(s) has recently been reported. This enzyme, KfoC, is approximately 60% identical to the Pasteurella chondroitin synthase (pmCS) and is also a dual-action enzyme.

Many P. multocida isolates produce GAG or GAG-like molecules as assessed by enzymatic degradation and removal of the capsule of living bacterial cells[9,10]. Carter Type A P. multocida, the major causative agent of fowl cholera and pasteurellosis, makes an HA capsule[11]. A single polypeptide, the HA synthase, pmHAS, polymerizes the HA chain by transferring both GlcUA and GlcNAc[12]. Type F P. multocida, the minor fowl cholera pathogen, produces a capsule composed of an unsulfated chondroitin sensitive to Flavobacterium chondroitin AC lyase[9,13,14]. Again, a dual-action chondroitin synthase, pmCS, polymerizes the chondroitin chain[14]. The capsule of another distinct P. multocida, Type D, was reported to be sensitive to heparin lyase III[9] which thereby led to the presently claimed and disclosed invention—the identification and characterization of pmHS (P. multocida heparin/heparosan synthase) and PgIA, the first and only known bacterial dual-action heparosan synthases.

Prior to recombinantly obtaining the pmHS gene and heterologously expressing it in a recombinant system, activity assays of *P. multocida* Type D enzymes were completed. Native membranes were prepared from a wild-type encapsulated Type D strain (P-3881; DeAngelis et al., 1996, the entirety of which is expressly incorporated herein in its entirety). The membranes were tested for in vitro sugar incorporation monitored by paper chromatography analysis. Characterization of the ability to co-polymerize the two sugars and utilize metal ions was performed. First, detection of co-polymerization activity of the Type D *P. multocida* strain was determined in vitro. The membranes+UDP-[$^{14}$C]GlcUA (300 μM; $1.5\times10^5$ dpm)+various combinations of the $2^{nd}$ sugar (UDP-GlcNAc, 900 μM) and/or EDTA chelator (45 mM) were mixed in 50 mM Tris, pH 7.2 with 20 mM $MnCl_2$ and 20 mM $MgCl_2$ reaction buffer. All reactions were performed at 30 degrees Celsius for 2.5 hours. The incorporation was measured by paper chromatography as disclosed in DeAngelis et al., 1996. The results of this co-polymerization activity are summarized in Table II.

TABLE II

| UDP-GlcNAc Added? | EDTA Added? | Incorporation (dpm) |
|---|---|---|
| No | No | 520 |
| Yes | No | 9150 |

TABLE II-continued

| UDP-GlcNAc Added? | EDTA Added? | Incorporation (dpm) |
|---|---|---|
| No | Yes | 35 |
| Yes | Yes | 160 |

Thus, it is apparent that the Type D *P. multocida* strain P-3881 has a metal-dependent enzyme that copolymerized both heparin precursors into a polymer.

Second, the metal requirement of the Type D *P. multocida* HS activity was tested in vitro. Membranes+UDP-[$^{14}$C]GlcUA+UDP-GlcNAc and buffer without the metals were mixed in a similar fashion as the preceding experiment except that various metals or EDTA (20 mM) were added as noted in Table III. The results of this metal specificity are summarized in Table III.

TABLE III

| Metal | dpm |
|---|---|
| None | 13 |
| Mg | 2960 |
| Mn | 3070 |
| Mn + Mg | 3000 |
| Co | 120 |

Thus, it is apparent that the Type D *P. multocida* HS requires either manganese or magnesium ion for enzymatic activity.

Further, the sugar specificity of the Type D *P. multocida* strain was determined in vitro in similar experiments. The ability to co-polymerize the sugars that compose the authentic backbone was tested by performing two parallel reactions:

A. UDP-[$^{14}$C]GlcUA+various combinations of $2^{nd}$ UDP-sugars.

B. UDP-[$^{3}$H]GlcNAc+various combinations of $2^{nd}$ UDP-sugars

The results of these experiments are summarized in Table IV. Significant $^{14}$C-GlcUA incorporation required UDP-GlcNAc and, conversely, significant $^{3}$H-GlcNAc incorporation required UDP-GlcUA; the enzyme copolymerizes the polysaccharide chain with both authentic heparin UDP-sugar precursors.

TABLE IV

| A. Hexosamine-transfer $2^{nd}$ Sugar Added | $^{14}$C dpm incorporation |
|---|---|
| None | 330 |
| UDP-GlcNAc | 2290 |
| UDP-GalNAc | 2790 |
| UDP-Glc | 450 |

| B. Uronic Acid Transfer $2^{nd}$ Sugar Added | $^{3}$H dpm incorporation |
|---|---|
| None | 170 |
| UDP-GlcUA | 1000 |
| UDP-GalUA | 290 |
| UDP-Glc | 185 |

It should be added that the above-described results show that the native Type D *P. multocida* membrane enzymes have relaxed hexosamine transfer specificity in vitro. Such relaxed hexosamine transfer specificity is an advantage for syntheses where the UDP-sugar supplied can be manipulated. In such a manner, novel and non-naturally occurring polymers can be created. These novel, non-naturally occurring polymers have significant utility and novel biological properties.

Experimental Procedures for Isolating HS Genes and Testing Function

Materials and *Pasteurella* Strains—Unless otherwise noted, all chemicals were from Sigma or Fisher, and all molecular biology reagents were from Promega. The wild-type encapsulated Type D *P. multocida* isolates, P-934 (swine), P-3881 (bovine), P-4058 (rabbit), and P-5695 (swine), were obtained from the USDA collection (Ames, Iowa). The strains were grown in brain heart infusion (Difco) at 37° C.

Analysis of Genomic DNA and Isolation of Capsule Biosynthesis Locus DNA—Preliminary data from Southern blot analysis using pmHAS-based hybridization probes[12] suggested that the Type A synthase and the putative Type D synthase were not very similar at the DNA level. However, PCR suggested that the UDP-glucose dehydrogenase genes, which encode an enzyme that produces the UDP-GlcUA precursor required for both HA and heparin biosynthesis, were very homologous. In most encapsulated bacteria, the precursor-forming enzymes and the transferases are located in the same operon. To make a hybridization probe predicted to detect the capsule locus, Type D chromosomal DNA served as a template in PCR reactions utilizing degenerate oligonucleotide primers (sense: GARTTYBTIMRIGARG-GIAARGCIYTITAYGAY (SEQ ID NO:12); antisense: RCARTAICCICCRTAICCRAAISWXG-GRTTRTTRTARTG (SEQ ID NO:13), where I=inosine; R=A or G; S=C or G; W=A or T; Y=C or T) corresponding to a conserved central region in many known UDP-glucose dehydrogenase genes. The ~0.3-kb amplicon was generated using Taq DNA polymerase (Fisher), gel-purified, and labeled with digoxigenin (High Prime system, Boehringer Mannheim).

A lambda library of Sau3A partially digested P-3881 DNA (~4-9 kb average length insert) was made using the BamHI-cleaved λZap Express™ vector system (Stratagene). The plaque lifts were screened by hybridization (5×SSC, 50° C.; 16 hrs) with the digoxigenin-labeled probe using the manufacturer guidelines for colorimetric development. *E. coli* XLI-Blue MRF' was co-infected with the purified, individual positive lambda clones and ExAssist helper phage to yield phagemids. The resulting phagemids were transfected into *E. coli* XLOLR cells to recover the plasmids. Sequence analysis of the plasmids using a variety of custom primers as well as the GPS-1 Genome Priming System (New England Biolabs) revealed a novel open reading frame, which we called pmHS (DNA sequence facilities at Oklahoma State University and University of Oklahoma HSC). We amplified and sequenced the ORF from several highly encapsulated isolates (see hereinbelow); very similar sequences were obtained.

Expression of Recombinant *P. multocida* Heparosan Synthase—The pmHS ORF (617 amino acids) was amplified from the various Type D genomic DNA template by 18 cycles of PCR (16) with Taq polymerase. For constructing the full-length enzyme, the sense primer (ATGAGCTTATT-TAAACGTGCTACTGAGC (SEQ ID NO: 14)) corresponded to the sequence at the deduced amino terminus of the ORF and the antisense primer (TTTACTCGTTATAAAAA-GATAAACACGGAATAAG (SEQ ID NO:15)) encoded the carboxyl terminus including the stop codon. In addition, a truncated version of pmHS was produced by PCR with the same sense primer but a different antisense primer (TATATT-TACAGCAGTATCATTTTCTAAAGG (SEQ ID NO:16)) to yield a predicted 501-residue protein, DcbF (SEQ ID NO:17)

(GenBank Accession Number AAK17905)[15]; this variant corresponds to residues 1-497 of pmHS followed by the residues TFRK.

The amplicons were cloned using the pETBlue-1 Acceptor system (Novagen) according to the manufacturer's instructions. The Taq-generated single A overhang is used to facilitate the cloning of the open reading frame downstream of the T7 promoter and the ribosome binding site of the vector. The ligated products were transformed into E. coli NovaBlue and plated on LB carbenicillin (50 µg/ml) and tetracycline (13 µg/ml) under conditions for blue/white screening. White colonies were analyzed by PCR-based screening and by restriction digestion. Plasmids with the desired ORF were transformed into E. coli Tuner, the T7 RNA polymerase-containing expression host, and maintained on LB media with carbenicillin and chloramphenicol (34 µg/ml) at 30° C. Mid-log phase cultures were induced with β-isopropylthiogalactoside (0.2 mM final) for 5 hrs. The cells were harvested by centrifugation, frozen, and membranes were prepared according to a cold lysozyme/sonication method[16] except 0.1 mM mercaptoethanol was included during the sonication steps. Membrane pellets were suspended in 50 mM Tris, pH 7.2, 0.1 mM EDTA and protease inhibitors.

Assays for Heparosan Synthase Activity—Incorporation of radiolabeled monosaccharides from UDP-[$^{14}$C]GlcUA and/or UDP-[$^3$H]GlcNAc precursors (NEN) was used to monitor heparosan synthase activity. Samples were assayed in a buffer containing 50 mM Tris, pH 7.2, 10 mM $MgCl_2$, 10 mM $MnCl_2$, 0-0.6 mM UDP-GlcUA, and 0-0.6 mM UDP-GlcNAc at 30° C. Depending on the experiment, a Type D acceptor polymer processed by extended ultrasonication of a capsular polysaccharide preparation (isolated by cetylpyridinium chloride precipitation of the spent Type D culture media)[14] was also added to the reaction mixture. The reaction products were separated from substrates by descending paper (Whatman 3M) chromatography with ethanol/1 M ammonium acetate, pH 5.5, development solvent (65:35). The origin of the paper strip was cut out, eluted with water, and the incorporation of radioactive sugars into polymer was detected by liquid scintillation counting with BioSafe II cocktail (RPI).

The metal preference of pmHS was assessed by comparing the signal from a "no metal" control reaction (0.5 mM EDTA) to reactions containing 10 to 20 mM manganese, magnesium, or cobalt chloride. To test the transfer specificity of pmHS, various UDP-sugars (UDP-GalNAc, UDPGalUA, or UDP-Glc) were substituted for the authentic heparosan precursors. The data from the recombinant construct containing pmHS gene from the P4058 strain is presented, but the results were similar to constructs derived from the P-934 or P-5695 strains.

Size Analysis and Enzymatic Degradation of Labeled Polymers—Gel filtration chromatography was used to analyze the size distribution of the labeled polymers. Separations were performed with a Polysep-GFC-P 4000 column (300× 7.8 mm; Phenomenex) eluted with 0.2 M sodium nitrate at 0.6 ml/min. Radioactivity was monitored with an in-line Radioflow LB508 detector (EG & G Berthold; 500 µl flow cell) using Unisafe I cocktail (1.8 ml/min; Zinsser). The column was standardized with fluorescein-labeled dextrans of various sizes. To further characterize the radiolabeled polymers, depolymerization tests with specific glycosidases was performed. The high molecular weight product was purified by paper chromatography. The origin of the strips was washed with 80% ethanol, air-dried, then extracted with water. The water extract was lyophilized, resuspended in a small volume of water and split into three aliquots. Two aliquots were treated with glycolytic enzymes for 2 days at 37° C. (Flavobacterium heparin lyase III, 6.7 mU/il, 50 mM sodium phosphate, pH 7.6, or Streptomyces HA lyase, 333 milliunits/il, 50 mM sodium acetate, pH 5.8). The last aliquot was mock-treated without enzyme in acetate buffer. The aliquots were quenched with SDS, subjected to paper chromatography, and the radiolabel at the origin was measured by liquid scintillation counting.

Results

Molecular Cloning of the Type D P. multocida Heparosan Synthase—A PCR product which contained a portion of the Type D UDP-glucose dehydrogenase gene was used as a hybridization probe to obtain the rest of the Type D P. multocida capsular locus from a lambda library. We found a functional heparosan synthase, which we named pmHS, in several distinct Type D strains from different host organisms isolated around the world. In every case, an open reading frame of 617 residues with very similar amino acid sequence (98-99% identical) was obtained. In the latter stages of our experiments, another group deposited a sequence from the capsular locus of a Type D organism in GenBank[15]. In their annotation, the carboxyl terminus of the pmHS homolog is truncated and mutated to form a 501-residue protein that was called DcbF (GenBank Accession Number AAK17905) (SEQ ID NO:17). No functional role for the protein except "glycosyltransferase" was described and no activity experiments were performed. As described herein, membranes or cell lysates prepared from E. coli with the recombinant dcbF gene do not possess heparosan synthase activity. The gene annotated as DcbF (SEQ ID NO:18) is truncated at the carboxyl terminus in comparison to the presently claimed and described P. multocida HS clones. The truncated (T) or the full-length (FL) open reading frames of DcbF were cloned into the expression system pETBlue-1 vector, as described hereinabove. Membranes isolated from the same host strain, E. coli Tuner with the various recombinant plasmids were tested in HS assays with both radiolabeled UDP-sugars. The results of these experiments are summarized in Table V.

TABLE V

| | Clone | |
|---|---|---|
| | [14C]GlcUA Incorp. (dpm) | [3H]GlcNAc Incorp. (dpm) |
| Negative Control | 160 | 40 |
| B1(FL) | 710(*) | 1040(*) |
| 012(T) | 40 | 265 |
| 013(T) | 70 | 1610 |
| 019(T) | 55 | 1105 |
| N2(T) | 70 | 1910 |
| N4(T) | 70 | 880 |
| N5(T) | 80 | 650 |

Five-fold less FL enzyme than T enzymes were tested in these parallel assays. At most, only a single GlcNAc sugar is added to the exogenously supplied acceptor in the truncated enzymes (T). Full-length HS from Type D P. multocida, however, adds both sugars (*) to the nascent chain. Thus, the previously annotated and deposited DcbF gene is not a functional heparosan synthase.

Another deduced gene was recently uncovered by the University of Minnesota in their Type A P. multocida genome project 17, called PgIA (GenBank Accession Number AAK02498), encoding 651 amino acids that are similar to pmHS (73% identical in the major overlapping region). However, the PgIA gene is not located in the putative capsule locus. This group made no annotation of the function of PgIA.

Our studies show that this PgIA protein also polymerizes GlcUA and GlcNAc residues to form heparosan. We also found that a Type D strain and a Type F strain also appear to contain a homologous PgIA gene as shown by PCR and activity analysis.

As mentioned before, during the pmHS cloning project in the present inventor(s)' laboratory, investigators at the Univ. of Minnesota published the complete genome of a *Pasteurella multocida* isolate. The fragments of the presently claimed and disclosed pmHS gene were utilized as the query in a BLAST search. A gene annotated as pgIA, but with no ascribed, predicted or demonstrated function was found to be very similar to the pmHS gene. The pgIA gene is not in the main capsule locus found by either the DeAngelis or the Adler groups. The pgIA open reading frame was obtained from two different encapsulated strains: Type A (P-1059 from a turkey—this strain is not the same as the Univ. of Minnesota strain—clones denoted as "A") and Type D (P-3881 from a cow—clones denoted as "D"). The pgIA gene was amplified from chromosomal templates prepared by method of Pitcher et al (*Letters in Applied Microbiology*, 1989). PCR with Taq polymerase (18 cycles) using custom flanking oligonucleotide primers that correspond to the region of the start codon and the stop codon of pgIA. An appropriate size amplicon corresponding to the pgIA gene was found in both Type A and D strains; this result was rather unexpected if one considers that the capsular compositions are HA and N-acetylheparosan polysaccharides, for Type A and Type D strains, respectively. The resulting ~1.9 kilobase PCR amplicons were ligated into an expression vector, pETBlue-1 (Novagen), transformed into the cloning host, *E. coli* Novablue (Novagen), and selected on LB carbenicillin and tetracycline plates at 30° C. The colonies were screened for the presence of insert in the proper orientation by PCR with a combination of vector and insert primers. Clones were streak isolated, small cultures were grown, and preparations of the plasmid DNA were made. The plasmids were transformed into the expression host, *E. coli* Tuner (Novagen), and selected on LB with carbenicillin and chloramphenicol.

After streak isolation, small cultures were grown at 30° C. as the starting inoculum (1:100) for larger cultures (50 ml) for protein expression and activity assay. These cultures were grown in the same LB supplemented with 1% casein amino acids and trace element solution with vigorous shaking (250 rpm) at 30° C. The cells were grown to mid-logarithmic phase (2.5 hours), induced with 0.5 mm IPTG, and grown for 4.5 hours. Cells were collected by centrifugation and frozen at −80° C. overnight. The membrane preparations were isolated by cold lysozyme/ultrasonication method of DeAngelis et al (*J. Biol. Chem.*, 1998; pmHAS isolation the contents of which are expressly incorporated herein in their entirety) except that 0.1 mM mercaptoethanol was used as the reducing agent. The membranes were assayed for radioactive sugar incorporation and descending paper chromatography (according to the methodology of DeAngelis and Padget-McCue, *J. Biol. Chem.*, 2000, the contents of which are expressly incorporated herein in their entirety).

In general, a mixture with membranes, 50 mM Tris, pH 7.2, 1 mM MgCl$_2$, 10 mM MnCl$_2$, 0.4 mM UDP-[$^3$H]GlcNAc, 0.2 mM UDP-[$^{14}$C]GlcUA, and heparin oligosaccharide acceptor (2 μg uronic acid) were incubated at 30° C. for 2.5 hours before analysis by paper chromatography. As expected for a polysaccharide synthase, both sugars were incorporated into polymer (Table VI). Negative controls using membranes from a plasmid with an irrelevant control insert, do not show incorporation (data not shown). Therefore, PgIA is a dual-action synthase capable of sugar biosynthesis as shown by functional expression of activity of one recombinant gene in a foreign host that normally does not make GlcUA/GlcNAc polymers. The relaxed specificity of UDP-sugar incorporation of PgIA should be of use for the design and production of new polymers with altered characteristics.

TABLE VI

In vitro incorporation of sugar by membranes containing recombinant pgIA.

| CLONE | [$^3$H]GlcNAc (dpm) | [$^{14}$C]GlcUA (dpm) |
|---|---|---|
| PgIA-A2 | 50,400 | 54,900 |
| PgIA-A4 | 39,100 | 41,000 |
| PgIA-D4 | 32,500 | 34,200 |
| PgIA-D7 | 44,800 | 46,600 |

The typical background for negative controls is less the 200 dpm incorporation. Type A and Type D isolates have the PgIA, a synthase that incorporates both GlcUA and GlcNAc sugars. (A=Type A; D=Type D; #=independent clone number).

Table VII shows PgIA Sugar Specificity test results. The experiments summarized in Table VII are similar to the experiments summarized in Table VI (with less enzyme) except that other UDP-sugars that are not normally found in heparin or heparosan were also tested (note—60 minute incubation times, 50 μl reactions). The Type A and the Type D enzymes behave in a similar fashion with relaxed sugar specificity in this test. The PgIA system can add a glucose instead of a GlcNAc sugar. The ability to co-polymerize the sugars that compose the authentic heparin backbone were tested by performing two parallel reactions:

UDP-[$^{14}$C]GlcUA+various combinations of 2$^{nd}$ UDP-sugars.

UDP-[$^3$H]GlcNAc+various combinations of 2$^{nd}$ UDP-sugars.

TABLE VII

Panel I. Type A PgIA-A2

| 2$^{nd}$ Sugar | [$^3$H]GlcNAc Incorporated into Polymer (dpm) |
|---|---|
| none | 450 |
| UDP-GlcUA | 12,900 |
| UDP-GalUA | 400 |
| UDP-Glc | 430 |

| 2$^{nd}$ Sugar | [$^{14}$C]GlcUA Incorporated into Polymer (dpm) |
|---|---|
| none | 60 |
| UDP-GlcNAc | 7,700 |
| UDP-GalNAc | 60 |
| UDP-Glc | 985 |

Panel II. Type D PgIA-D7

| 2$^{nd}$ Sugar | [$^3$H]GlcNAc Incorporated into Polymer (dpm) |
|---|---|
| none | 570 |
| UDP-GlcUA | 13,500 |
| UDP-GalUA | 530 |
| UDP-Glc | 500 |

| 2$^{nd}$ Sugar | [$^{14}$C]GlcUA Incorporated into Polymer (dpm) |
|---|---|
| none | 60 |
| UDP-GlcNAc | 6,500 |
| UDP-GalNAc | 40 |
| UDP-Glc | 660 |

Table VIII. Acceptor Usage of PgIA from Types A and D

The Type A and the Type D clones were tested for stimulation by addition of the Type D polysaccharide acceptor (described hereinbefore with respect to pmHS). Weaker stimulation of activity by acceptor on pgIA was observed in comparison to pmHS (comparison is not shown here).

| | [$^{14}$C-GlcUA] incorporation | |
|---|---|---|
| Clone | Acceptor | NO Acceptor |
| A2 | 1560 | 1210 |
| D7 | 1240 | 1080 |

*P. multocida* Type F-derived recombinant pgIA is thus also a heparosan synthase. As shown in the following Table IX, the Type F PgIA can incorporate the authentic heparin sugars.

TABLE IX

| | Activity of pgIA from Type F | | |
|---|---|---|---|
| Membranes | Acceptor | $^{3}$H-GlcNAc (dpm) | $^{14}$C-GlcUA (dpm) |
| Blank | 0 | 8 | 8 |
| PgIA F 3 | + | 7100 | 3100 |
| PgIA F 4 | 0 | 6100 | 3800 |
| PgIA F 4 | + | 11000 | 6400 |
| PgIA F 18 | 0 | 20000 | 10000 |
| PgIA F 18 | + | 23000 | 12000 |
| PgIA D 7 | 0 | 36000 | 17000 |

The pgIA homolog of *P. multocida* Type F strain P-4218 was amplified with flanking primers as described for the Type A and D strains. The ORF was subcloned into the pETBlue-1 system in *E. coli* Tuner cells for use as a source of membrane preparations as described. Three independent clones (F 3,4, 18) were assayed under standard HS assay measuring radiolabeled sugar incorporation with paper chromatography. A negative control, membranes from "Blank" vector and a positive control, the Type D pgIA clone D7, were tested in parallel. Reactions plus/minus the Type D polymer acceptor were assayed.

The next best heterologous matches for the pmHS enzyme in the Genbank database are KfiA and KfiC proteins from *E. coli* K5; these two proteins work together to make the heparosan polymer.[7,8] There is a good overall alignment of the enzyme sequences if smaller portions of pmHS ORF are aligned separately with KfiA (pmHS2, SEQ ID NO:11) and KfiC (pmHS1, SEQ ID NO:10) (FIG. 1). The MULTALIN alignment program (Corpet, 1988) identified regions that were very similar. Some of the most notable sequence similarities occur in the regions containing variants of the DXD amino acid sequence motif. Indeed, the first 1-360 residues of pmHS1 (denoted also as HSA1: SEQ ID NO:10) align with an approximate 38% identity to the *E. coli* KfiC, a single action GlcUA-transferase, while the 361-617 residues of pmHS2 (denoted also HSA2: SEQ ID NO:11) align with an approximate 31% identity to the *E. coli* KfiA, a GlcNAc-transferase. Thus, the pmHS is a naturally occurring fusion of two different glycosyltransferase domains. The pmHS is a dual action enzyme that alone makes heparin/heparosan polymers because both sugar transferase sites exist in one polypeptide enzyme.

Heterologous Expression of a Functional *P. multocida* Heparosan Synthase—

Membrane extracts derived from *E. coli* Tuner cells containing the plasmid encoding pmHS, but not samples from cells with the vector alone, synthesized polymer in vitro when supplied with both UDP-GlcUA and UDP-GlcNAc simultaneously. The identity of the polymer as heparosan was verified by its sensitivity to *Flavobacterium* heparin lyase III (~97% destroyed after treatment) and its resistance to the action of *Streptomyces* HA lyase. No substantial incorporation of radiolabeled [$^{14}$C]GlcUA into polymer was observed if UDP-GlcNAc was omitted, or if UDP-GalNAc was substituted for UDP-GlcNAc. Conversely, in experiments using UDP-[$^{3}$H]GlcNAc, substantial incorporation of radiolabel into polymer was only noted when UDP-GlcUA was also present. UDP-GalUA or UDP-Glc did not substitute for UDP-GlcUA. No polymerization or transferase activity was detected if the divalent metal ions were chelated with EDTA. Maximal activity was observed in reactions that contained Mn ion, but Mg also supported substantial incorporation (65%-85% maximal). Cobalt was a poorer cofactor (~30% maximal). The addition of the heparosan polymer acceptor increased sugar incorporation catalyzed by pmHS at least 7- to 25-fold in comparison to parallel reactions without acceptor (FIG. 2) in analogy to observations of pmHAS[18] and pmCS[14]. The acceptor stimulation of activity is due to the lower efficiency or slower rate of initiation of a new polymer chain in comparison to the elongation stage in vitro. The exogenous acceptor sugar associates with the recombinant enzyme's binding site for the nascent chain and then is elongated rapidly.

Analysis by gel filtration chromatography indicated that recombinant pmHS produced long polymer chains (~1-3× 103 monosaccharides or ~200-600 kDa) in vitro without acceptor (FIG. 3). If acceptor polymer was supplied to parallel reaction mixtures, then higher levels of shorter chains (~0.1-2×103 monosaccharides or ~20-400 kDa added to acceptor) were more rapidly produced. Radioactivity from both labeled GlcUA and GlcNAc sugars co-migrated as a single peak in all chromatography profiles. Some chains also appear to be initiated de novo in reactions with acceptor as evidenced by the small peak of higher molecular weight material near the void volume. Apparently, once pmHS either starts a new chain or binds an existing chain, then rapid elongation is performed.

We found in parallel tests that membranes or lysates prepared from recombinant cells containing the predicted dbcF gene[15] (SEQ ID NO:17), a truncated version of pmHS, in the same expression vector, do not exhibit heparosan synthase activity. Even with large amounts of total protein, repeated polymerization was not observed and no significant radiolabel incorporation above background levels was noted.

Discussion

We have molecularly cloned a dual-action glycosyltransferase responsible for polymerizing the heparosan backbone component of the Type D *P. multocida* capsular polysaccharide. As discussed earlier, the first 497 residues of the pmHS protein are virtually identical to the hypothetical DcbF sequence. We have sequenced the DNA from the equivalent P-934 isolate obtained from the same USDA collection as reported[15], as well as several other Type D strains, but our results do not agree with the dcbF open reading frame. The Adler group appears to have made a sequencing error that resulted in a frame-shift mutation; a conceptual premature termination led to the creation of the erroneously truncated dcbF annotation. Recently, we have determined that the *Pas-* teurella hyaluronan synthase, pmHAS, contains two active sites in a single polypeptide by generating mutants that transfer only GlcUA or only GlcNAc[19]. Interestingly, mixing the two different mutant pmHAS proteins reconstituted the HA synthase activity. We hypothesized that one domain, called A1, is responsible for GlcNAc transfer and the other domain, called A2, is responsible for GlcUA transfer[19]. The chondroitin synthase, pmCS, transfers a different hexosamine, GalNAc, and also appears to contain a similar two-domain structure[14]. The amino acid sequence of the heparosan synthase, pmHS, however, is very different from other *Pasteurella* GAG synthases, pmHAS and pmCS. The pmHAS and pmHS enzymes both perform the task of polymerizing the identical monosaccharides; HA and heparin only differ with respect to their linkages. The creation of different anomeric linkages probably requires very distinct active sites due to the disparity between a retaining (to form α-linkages) and an inverting (to form β-linkages) transfer mechanism. The putative dual-action vertebrate heparin synthases, EXT1 (SEQ ID NO:19) and EXT 2 (SEQ ID NO:20), also appears to have two transferase domains, but the amino acid sequences are not similar to pmHS[20]. Thus, by aligning pgIA, pmHS (B10 and A2 clones), KfiA, or KfiC, deduced amino acid sequence motifs have been identified. Such motifs are listed below and the alignment is shown in FIG. 4 A-G.

Two distinct regions of pmHS (pmHS1 and pmHS2) are similar to the *E. coli* K5 KfiA or KfiC proteins suggesting the limits of the sugar transfer domains (FIG. 1). On the basis of sequence similarity, if the Kfi studies are correct, then GlcUA transfer and GlcNAc transfer occur at the amino and carboxyl portions of pmHS, respectively. The pmHS protein may be the result of the fusion of two ancestral single-action enzymes. The efficiency and convenience of combining the two required enzyme activities into a single polypeptide seems clear, but as a counterexample, the *E. coli* KfiA and KfiC proteins remain separate entities. Interestingly, pgIA, a gene with no reported function from a Type A[17] isolate is (~70%) similar to the pmHS gene of a Type D strain. In parallel expression experiments, PgIA from Type A or D or F strains also appear to be heparosan synthases, as shown hereinabove. It is quite puzzling that the Type A strain would have a heparosan synthase as well as the known HA synthase. The major Type A capsular polymer was shown to be HA, but in retrospect, a small amount of heparosan would be difficult or impossible to detect in these characterization studies[11]. A possible scenario for the presence of a heparosan synthase in the Type A bacteria is that the pgIA gene is repressed or silent and not expressed in this host under laboratory conditions. The pgIA gene could also be a cryptic remnant from an ancestral organism (i.e., before Types A and D and F diverged) that has been maintained and the gene product is still functional. Another interesting possibility is that in Type A organisms either the pmHAS or the pgIA gene is utilized at different times depending on conditions or stage of infection; using different capsular polymers could serve as a phase-shift mechanism.

Comparisons of the two known sets of heparin/heparosan biosynthesis enzymes from the *E. coli* K5 Kfi locus, the PgIA enzyme, and the pmHS from Type D capsular locus, allows for the initial assessment and bioinformatic prediction of new enzymes based on the amino acid sequence data. The closer the match (% identity) in a single polypeptide for the two sequence motifs described hereinafter (corresponding to the critical elements of the GlcUA-transferase and the GlcNAc-transferase), the higher the probability that the query enzyme is a new heparin/heparosan synthase (a single dual-action enzyme). The closer the match (% identity) in two polypeptides (especially if encoded in the same operon or transcriptional unit) for the two sequence motifs, the higher the probability that the query enzymes are a pair of single-action glycosyltransferases. Thus, one of ordinary skill in the art would appreciate that given the following motifs, one would be able to ascertain and ascribe a probable heparin synthase function to a newly discovered enzyme and then test this ascribed function in a manner to confirm the enzymatic activity. Thus, single dual-action enzymes possessing enzymatic activity to produce heparin/heparosan and having at least one of the two disclosed motifs are contemplated as being encompassed by the presently claimed and disclosed invention.

Motif I:

(SEQ ID NO:21)

QTYXN(L/I)E$X_4$DDX(S/T)(S/T)D(K/N)(T/S)$X_6$IAX(S/T)(S/T)(S/T)(K/R)V(K/R)$X_6$NXGXY$X_{16}$FQDXDDX(C/S)H(H/P)ERIXR

Motif II:

(SEQ ID NO:22)

(K/R)DXGKFI$X_{12-17}$DDDI(R/I)YPXDY$X_3$M$X_{40-50}$VNXLGTGTV

Motif I corresponds to the GlcUA transferase portion of the enzyme, while Motif II corresponds to the GlcNAc transferase portion of the enzyme. With respect to the motifs:

X=any residue parentheses enclose a subset of potential residues [separated by a slash]

that may be at a particular position (e.g., —(K/R) indicates that either K or R may be found at the position—i.e., there are semiconserved residues at that position.

The consensus X spacing is shown with the number of residues in subscript (e.g., $X_{12-17}$), but there are weaker constraints on these particular residues, thus spacing may be longer or shorter. Conserved residues may be slightly different in a few places especially if a chemically similar amino acid is substituted (e.g., K for a R, or E for a D). Overall, at the 90% match level, the confidence in this predictive method is very high, but even a 70-50% match level without excessive gap introduction (e.g., altered spacing between conserved residues) or rearrangements (miss-positioning with respect to order of appearance in the amino to carboxyl direction) would also be considered to be within the scope of these motifs. One of ordinary skill in the art, given the present specification, general knowledge of the art, as well as the extensive literature of sequence similarity and sequence statistics (e.g., the BLAST information website at www.ncbi.nlm.mih.gov), would appreciate the ability of a practitioner to identify potential new heparin/heparosan synthases based upon sequence similarity or adherence to the motifs presented herein and thereafter test for functionality by means of heterozologous expression, to name but one example.

Bacteria-derived heparosan may be converted by epimerization and sulfation into a polymer that resembles the mammalian heparin and heparan sulfate because all the modifying enzymes have been identified [3]. In general, sulfation with chemical reagents ($SO_3$, chlorosulfonic acid) or sulfo-transferases (i.e., 2-0-GlcUA-sulfotransferase, etc.) And PAPs precursor is possible. N-sulfation can be done by using either chemical means (hydrazinolysis and subsequent N-sulfation) or enzymatic means with dual function deacetylase/N-sulfotransferase. For creation of iduronic acid, epimerization can be performed enzymatically with heparin epimerase or chemically with super-critical carbon dioxide. The art is replete with articles, methods, and procedures for sulfating and epimerizing heparosan to form heparin. Example, include Leali, et al., Fibroblast Growth Factor-2 Antagonistactivity and Angiostatic Capacity of Sulfated *E. coli* KS Polysaccharide Derivatives, J. Biol. Chem., Vol. 276, No. 41, Oct. 12, 2001, pp. 37900-902; Esko, et al., Molecular Diversity of Heparin Sulfate, J. Clin. Invest. 108: 169-173 (2001); and Crawford, et al., Cloning, Golgi Localization, and Enzyme Activity of the Full-Length Heparin/Heparosan Sulfate—Glucuronic Acid C5-Epimerase, J. Biol. Chem., Vol. 276, No. 24, Jun. 15, 2001, pp. 21530-543, the contents of each being hereby expressly incorporated by reference in their entirety. Thus, given the present specification which discloses and teaches methods for the recombinant production of Heparosan, one of ordinary skill in the art would be capable of producing Heparin therefrom. As such, Heparin obtained through the process of sulfating and epimerizing Heparosan is contemplated as falling within the scope of the presently disclosed and claimed invention.

pmHS or PgIA (or an improved recombinant version) may be a more economical and useful sources of heparosan than *E. coli* K5 for several reasons. pmHS and PgIA have a higher intrinsic biosynthetic capacity for capsule production. The *Pasteurella* capsule radius often exceeds the cell diameter when observed by light microscopy of India Ink-prepared cells. On the other hand, visualization of the meager *E. coli* K5 capsule often requires electron microscopy. From a safety standpoint, *E. coli* K5 is a human pathogen, while Type D *Pasteurella* has only been reported to cause disease in animals. Furthermore, with respect to recombinant gene manipulation to create better production hosts, the benefits of handling only a single gene encoding pmHS or PgIA, dual action synthases, in comparison to utilizing KfiA and C (and probably KfiB) are obvious. The in vitro properties of pmHS and pgIA are also superior; these enzymes can make large chains in vitro either with or without an exogenous acceptor sugar, but KfiA and KfiC do not.

The discovery of pmHS and PgIA expands the known GAG biosynthesis repertoire of *P. multocida*. Depending on the Carter capsular type, this widespread species produces HA, heparosan, or chondroitin.

Thus, it should be apparent that there has been provided in accordance with the present invention purified nucleic acid segments having coding regions encoding enzymatically active heparosan synthase, methods of producing heparosan from the pmHS or pgIA gene, and the use of heparosan produced from a heparosan synthase encoded by the pmHS or pgIA gene, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

REFERENCES

The following references, to the extent that they provide exemplary procedural or other details supplementary to those set forth herein, are specifically incorporated herein by reference.

1. Roden, L. (1980) in The Biochemistry of Glycoproteins and Proteoglycans (Lennarz, W. J., ed) pp. 267-371, Plenum Publishing Corp., New York
2. Lidholt, K. (1997) Biochem. Soc. Trans. 25, 866-870
3. Esko, J. D. and Lindahl U. (2001) J. Clin. Invest., 108:169-173
4. Roberts, I. S. (1996) Annu. Rev. Microbiol. 50, 285-315
5. Vann, W. F., Schmidt, M. A., Jann, B., and Jann, K. (1981) Eur. J. Biochem. 116, 359-364
6. Rodriguez, M. L., Jann, B., and Jann, K. (1988) Eur. J. Biochem. 177, 117-124
7. Griffiths, G., Cook, N. J., Gottfridson, E., Lind, T., Lidholt, K., and Roberts, I. S. (1998) J. Biol. Chem., 273, 11752-11757
8. Hodson, N., Griffiths, G., Cook, N., Pourhossein, M., Gottfridson, E., Lind, T., Lidholt, K. and Roberts, I. S. (2000) J. Biol. Chem., 275:27311-27315.
9. Rimler, R. B. (1994) Vet. Rec. 134, 191-192
10. Rimler, R. B., Register, K. B., Magyar, T., and Ackermann, M. R. (1995) Vet. Microbiol. 47, 287-294
11. Rosner, H., Grimmecke, H. D., Knirel, Y. A., and Shashkov, A. S. (1992) Carb. Res. 223, 329-333
12. DeAngelis, P. L., Jing, W., Drake, R. R. and Achyuthan, A. M. (1998) J. Biol. Chem. 273, 8454-8458
13. Rimler, R. B. and Rhoades, K. R. (1987) J. Clinic. Microbiol. 25, 615-618
14. DeAngelis, P. L. and Padgett-McCue, A. J. (2000) J. Biol. Chem., 275: 24124-24129
15. Townsend, K. M., Boyce, J. D., Chung, J. Y., Frost, A. J., and Adler, B. (2001) J. Clin. Microbiol. 39:924-929
16. DeAngelis, P. L., and Weigel, P. H. (1994) Biochem. 33, 9033-9039
17. May, B. J., Zhang, Q., Li, L. L., Paustian, M. L., Whittam, T. S., and Kapur, V. (2001) Proc. Natl. Acad. Sci. U.S.A. 98:3460-3465
18. DeAngelis, P. L. (1999) J. Biol. Chem. 274, 26557-26562
19. Jing, W. and DeAngelis, P. L. (2000) Glycobiology 10: 883-889
20. Duncan, G., McCormick, C., and Tufaro, F. (2001) J. Clin. Invest. 108: 511-516
21. Corpet, F. (1988) Nucleic Acids Res. 16:10881-10890 18

SEQUENCE LISTING

```
<160> NUMBER OF SEQ ID NOS: 22

<210> SEQ ID NO 1
<211> LENGTH: 1851
<212> TYPE: DNA
<213> ORGANISM: Pasteurella multocida

<400> SEQUENCE: 1
atgagcttat ttaaacgtgc tactgagcta tttaagtcag gaaactataa agatgcacta      60
actctatatg aaaatatagc taaaatttat ggttcagaaa gccttgttaa atataatatt     120
```

```
gatatatgta aaaaaaatat aacacaatca aaaagtaata aaatagaaga agataatatt    180
tctggagaaa acaaattttc agtatcaata aaagatctat ataacgaaat aagcaatagt    240
gaattaggga ttacaaaaga aagactaggr gccccccctc tagtcagtat tataatgact    300
tctcataata cagaaaaatt cattgaagcc tcaattaatt cactattatt gcaaacatac    360
aataacttag aagttatcgt tgtagatgat tatagcacag ataaacatt tcagatcgca    420 tccagaatag caaactctac aagtaaagta aaaacattcc gattaaactc aaatctaggg    480
acatactttg cgaaaaatac aggaatttta aagtctaaag gagatattat tttctttcag    540
gatagcgatg atgtatgtca ccatgaaaga atcgaaagat gtgttaatgc attattatcg    600
aataaagata atatagctgt tagatgtgca tattctagaa taaatctaga aacacaaaat    660
ataataaaag ttaatgataa taaatacaaa ttaggattaa taactttagg cgtttataga    720
aaagtattta atgaaattgg ttttttttaac tgcacaacca aagcatcgga tgatgaattt    780
tatcatagaa taattaaata ctatggtaaa aataggataa ataacttatt tctaccactg    840
tattataaca caatgcgtga agattcatta ttttctgata tggttgagtg ggtagatgaa    900
aataatataa agcaaaaaac ctctgatgct agacaaaatt atctccatga attccaaaaa    960
atacacaatg aaaggaaatt aaatgaatta aaagagattt ttagcttttcc tagaattcat   1020 gacgccttac ctatatcaaa agaaatgagt aagctcagca accctaaaat tcctgtttat   1080
ataaatatat gctcaatacc ttcaagaata aaacaacttc aatacactat tggagtacta   1140
aaaaaccaat gcgatcattt tcatatttat cttgatggat atccagaagt acctgatttt   1200
ataaaaaaac tagggaataa agcgaccgtt attaattgtc aaaacaaaaa tgagtctatt   1260
agagataatg gaaagtttat tctattagaa aaacttataa aggaaaataa agatggatat   1320
tatataactt gtgatgatga tatccggtat cctgctgact acacaaacac tatgataaaa   1380
aaaattaata aatacaatga taaagcagca attggattac atggtgttat attcccaagt   1440
agagtcaaca agtattttc atcagacaga attgtctata attttcaaaa acctttagaa   1500
aatgatactg ctgtaaatat attaggaact ggaactgttg cctttagagt atctattttt   1560 aataaattt ctctatctga ttttgagcat cctggcatgg tagatatcta ttttctata   1620 ctatgtaaga aaaacaatat actccaagtt tgtatatcac gaccatcgaa ttggctaaca   1680
gaagataaca aaaacactga gaccttattt catgaattcc aaaatagaga tgaaatacaa   1740
agtaaactca ttatttcaaa caaccccttgg ggatactcaa gtatatatcc actattaaat   1800
aataatgcta attattctga acttattccg tgtttatctt tttataacga g             1851
```

<210> SEQ ID NO 2
<211> LENGTH: 617
<212> TYPE: PRT
<213> ORGANISM: Pasteurella multocida

<400> SEQUENCE: 2

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60
```

-continued

```
Lys Phe Ser Val Ser Ile Lys Asp Leu Tyr Asn Glu Ile Ser Asn Ser
 65                  70                  75                  80

Glu Leu Gly Ile Thr Lys Glu Arg Leu Gly Ala Pro Pro Leu Val Ser
             85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
            115                 120                 125

Asp Asp Tyr Ser Thr Asp Lys Thr Phe Gln Ile Ala Ser Arg Ile Ala
            130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Thr Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
```

-continued

```
                485                 490                 495

Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
        515                 520                 525

Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
                565                 570                 575

Asp Glu Ile Gln Ser Lys Leu Ile Ile Ser Asn Asn Pro Trp Gly Tyr
            580                 585                 590

Ser Ser Ile Tyr Pro Leu Leu Asn Asn Asn Ala Asn Tyr Ser Glu Leu
        595                 600                 605

Ile Pro Cys Leu Ser Phe Tyr Asn Glu
    610                 615

<210> SEQ ID NO 3
<211> LENGTH: 1854
<212> TYPE: DNA
<213> ORGANISM: Pasteurella multocida

<400> SEQUENCE: 3
atgagcttat ttaaacgtgc tactgagcta tttaagtcag gaaactataa agatgcacta     60
actctatatg aaaatatagc taaaatttat ggttcagaaa gccttgttaa atataatatt    120
gatatatgta aaaaaaatat aacacaatca aaaagtaata aaatagaaga agataatatt    180
tctggagaaa acaaattttc agtatcaata aaagatctat ataacgaaat aagcaatagt    240
gaattaggga ttacaaaaga aagactagga gcccccccctc tagtcagtat tataatgact    300
tctcataata cagaaaaatt cattgaagcc tcaattaatt cactattatt gcaaacatac    360
aataacttag aagttatcgt tgtagatgat tatagcacag ataaaacatt tcagatcgca    420
tccagaatag caaactctac aagtaaagta aaaacattcc gattaaactc aaatctaggg    480
acatactttg cgaaaaatac aggaatttta aagtctaaag gagatattat tttctttcag    540
gatagcgatg atgtatgtca ccatgaaaga atcgaaagat gtgttaatgc attattatcg    600
aataaagata atatagctgt tagatgtgca tattctagaa taaatctaga aacacaaaat    660
ataataaaag ttaatgataa taaatacaaa ttaggattaa taactttagg cgtttataga    720
aaagtattta atgaaattgg tttttttaac tgcacaacca aagcatcgga tgatgaattt    780
tatcatagaa taattaaata ctatggtaaa aataggataa ataacttatt tctaccactg    840
tattataaca caatgcgtga agattcatta ttttctgata tggttgagtg ggtagatgaa    900
aataatataa agcaaaaaac ctctgatgct agacaaaatt atctccatga attccaaaaa    960
atacacaatg aaaggaaatt aaatgaatta aaagagattt ttagctttcc tagaattcat   1020
gacgccttac ctatatcaaa agaaatgagt aagctcagca accctaaaat tcctgtttat   1080
ataaatatat gctcaatacc ttcaagaata aaacaacttc aatacactat tggagtacta   1140
aaaaaccaat gcgatcattt tcatatttat cttgatggat atccagaagt acctgatttt   1200
ataaaaaaac tagggaataa agcgaccgtt attaattgtc aaaacaaaaa tgagtctatt   1260
agagataatg gaaagtttat tctattagaa aaacttataa aggaaaataa agatggatat   1320
tatataactt gtgatgatga tatccggtat cctgctgact acataaacac tatgataaaa   1380
```

-continued

```
aaaattaata aatacaatga taaagcagca attggattac atggtgttat attcccaagt   1440
agagtcaaca agtattttc atcagacaga attgtctata attttcaaaa acctttagaa    1500
aatgatactg ctgtaaatat attaggaact ggaactgttg cctttagagt atctattttt   1560
aataaatttt ctctatctga ttttgagcat cctggcatgg tagatatcta tttttctata   1620
ctatgtaaga aaacaatat actccaagtt tgtatatcac gaccatcgaa ttggctaaca    1680
gaagataaca aaacactga gaccttattt catgaattcc aaaatagaga tgaaatacaa    1740
agtaaactca ttatttcaaa caaccccttgg ggatactcaa gtatatatcc attattaaat  1800
aataatgcta attattctga acttattccg tgtttatctt tttataacga gtaa          1854
```

<210> SEQ ID NO 4
<211> LENGTH: 617
<212> TYPE: PRT
<213> ORGANISM: Pasteurella multocida

<400> SEQUENCE: 4

-continued

```
Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320
Ile His Asn Glu Arg Lys Leu Asn Glu Leu Lys Glu Ile Phe Ser Phe
                325                 330                 335
Pro Arg Ile His Asp Ala Leu Pro Ile Ser Lys Glu Met Ser Lys Leu
            340                 345                 350
Ser Asn Pro Lys Ile Pro Val Tyr Ile Asn Ile Cys Ser Ile Pro Ser
        355                 360                 365
Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400
Ile Lys Lys Leu Gly Asn Lys Ala Thr Val Ile Asn Cys Gln Asn Lys
                405                 410                 415
Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445
Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480
Arg Val Asn Lys Tyr Phe Ser Ser Asp Arg Ile Val Tyr Asn Phe Gln
                485                 490                 495
Lys Pro Leu Glu Asn Asp Thr Ala Val Asn Ile Leu Gly Thr Gly Thr
            500                 505                 510
Val Ala Phe Arg Val Ser Ile Phe Asn Lys Phe Ser Leu Ser Asp Phe
        515                 520                 525
Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560
Glu Asp Asn Lys Asn Thr Glu Thr Leu Phe His Glu Phe Gln Asn Arg
                565                 570                 575
Asp Glu Ile Gln Ser Lys Leu Ile Ile Ser Asn Asn Pro Trp Gly Tyr
            580                 585                 590
Ser Ser Ile Tyr Pro Leu Leu Asn Asn Asn Ala Asn Tyr Ser Glu Leu
        595                 600                 605
Ile Pro Cys Leu Ser Phe Tyr Asn Glu
    610                 615
```

```

<210> SEQ ID NO 5
<211> LENGTH: 1940
<212> TYPE: DNA
<213> ORGANISM: Pasteurella multocida

<400> SEQUENCE: 5
aacaggggat aaggtcagta aatttaggat gatttttgac taatggataa atacttgaat     60
atccccatgg accgttttcc atgatcagct gagtttgttg ctcatcattg tctcgatatt    120
gatgatagag tgtttcgctg tctctattat cttccgttag ccagtttgct ggtcttgaaa    180
tacaaatctg aagaatatta tttttcttac acaagagaga gaaatagata tcagccatgc    240
```

-continued

```
ctgaatgggt aaagtcagaa agagaaaatt gattaaagag actgactcta aagctaacag    300
ttcctgtacc taatacattg accgctttgt ctttttccag aggtttatag aagctatata    360
ccagtctatc cgccgaaaaa tatttggtca ttctacttgg aaagagaatg ccgtgtaaac    420
caataaccgc tttatcatcg tattcattca gcttcttgat catcgtattg atgtaatcgc    480
ttggatagat aatgtcatca tcacaggtta tataatatcc atcttgattt ttttcaatca    540
actcttccag taaaatgaat ttgccattat ctctaatgga gttatcttta tctttgcaat    600
gaacaacggt tgctttatta cctaaatttt ttatgaagtc agggatttct acatagccat    660
caagataaat atgaaaatga tcacattgat tttttagtat gccgataata cgtcgtaatt    720
gcgctattct tgagggaata gaacaaatat tgatataaac aggaatctta ggattggaca    780
acttactcat ttcttgtggt actggtaagg catcgtaaat acgagggaat tgaaaaagat    840
ttttgaaatc atgtgaggca gtttcgttat gcatcgcttg aaacagggtt gcataatgtt    900
gtctggtatc agacattttc tgtattatgt tatgattgtc tatccattca accatatcag    960
taaataaaga gttttctctc attgtgttgt agtataacgg caagagtaaa tttttttattt   1020 tttcttttcc ataatatttc gcaattctat gaaaaaactc atcatctgag cctttagtcg   1080
tacaattgaa gaaaccaatt tcttgaaata cttttctgtg catacccaag gttataaaac   1140
ctaatctata atccatatta ttgactttaa tgatatgttg tgtttctggt gctagtcttg   1200
agtatgcaca acgaacagca atagtttctt tattagctaa taatatattt acacatcttt   1260
ctattctttc atgatgacat acatcatcac tatcttgaaa gaaaataatg tcacctttag   1320 atttaatat gcctgtattt ttcgcaaagt aagttcctag gtttgaattt aatctaaata    1380
ctctgacttt gcttgttgta ttcgctattc tcgaggcaat ttcaaatgta ttatccgagc   1440
tatcatcatc tacaataata atttctatgt ttttatatgt ttgtaacaat aatgaattaa   1500
tagaagcttc gataaattgc gctgtattgt gagatgtcat gataatactg actaatggat   1560
ttacgctgtt ggtttctttg actaacccta aatcactttt agcgacttca ttatataaat   1620
ctgttattga tgttgtttgc ttatcttttt ctagctttgc ttctaatgct tgattatagg   1680
tatatatttt ttcaaattct tgcagaacca attggagttg ttttaataaa agtttatttt   1740
cgttttcaag ggatgcggat agcggatgtt tactgtcctg ttttgccaat aaagtttgtt   1800
gagaaataat gtctttgttt aaagttgttt ttagactatc aattttattt tgaaaggtgt   1860
tgagttcatt ttctttttca tgttgggggg gatttttagt catttgtttt tgagtcatct   1920 cttttttttct cttcatttca                                               1940
```

<210> SEQ ID NO 6
<211> LENGTH: 651
<212> TYPE: PRT
<213> ORGANISM: Pasteurella multocida

<400> SEQUENCE: 6

```
Met Lys Arg Lys Lys Glu Met Thr Gln Lys Gln Met Thr Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
        35                  40                  45

Leu Leu Ala Lys Gln Asp Ser Lys His Pro Leu Ser Ala Ser Leu Glu
    50                  55                  60

Asn Glu Asn Lys Leu Leu Leu Lys Gln Leu Gln Leu Val Leu Gln Glu
```

-continued

```
             65                  70                  75                  80
        Phe Glu Lys Ile Tyr Thr Tyr Asn Gln Ala Leu Glu Ala Lys Leu Glu
                         85                  90                  95

Lys Asp Lys Gln Thr Thr Ser Ile Thr Asp Leu Tyr Asn Glu Val Ala
                        100                 105                 110

Lys Ser Asp Leu Gly Leu Val Lys Glu Thr Asn Ser Val Asn Pro Leu
                        115                 120                 125

Val Ser Ile Ile Met Thr Ser His Asn Thr Ala Gln Phe Ile Glu Ala
                        130                 135                 140

Ser Ile Asn Ser Leu Leu Leu Gln Thr Tyr Lys Asn Ile Glu Ile Ile
        145                 150                 155                 160

Ile Val Asp Asp Asp Ser Ser Asp Asn Thr Phe Glu Ile Ala Ser Arg
                        165                 170                 175

Ile Ala Asn Thr Thr Ser Lys Val Arg Val Phe Arg Leu Asn Ser Asn
                        180                 185                 190

Leu Gly Thr Tyr Phe Ala Lys Asn Thr Gly Ile Leu Lys Ser Lys Gly
                        195                 200                 205

Asp Ile Ile Phe Phe Gln Asp Ser Asp Val Cys His His Glu Arg
                        210                 215                 220

Ile Glu Arg Cys Val Asn Ile Leu Leu Ala Asn Lys Glu Thr Ile Ala
        225                 230                 235                 240

Val Arg Cys Ala Tyr Ser Arg Leu Ala Pro Glu Thr Gln His Ile Ile
                        245                 250                 255

Lys Val Asn Asn Met Asp Tyr Arg Leu Gly Phe Ile Thr Leu Gly Met
                        260                 265                 270

His Arg Lys Val Phe Gln Glu Ile Gly Phe Phe Asn Cys Thr Thr Lys
                        275                 280                 285

Gly Ser Asp Asp Glu Phe Phe His Arg Ile Ala Lys Tyr Tyr Gly Lys
                        290                 295                 300

Glu Lys Ile Lys Asn Leu Leu Leu Pro Leu Tyr Tyr Asn Thr Met Arg
        305                 310                 315                 320

Glu Asn Ser Leu Phe Thr Asp Met Val Glu Trp Ile Asp Asn His Asn
                        325                 330                 335

Ile Ile Gln Lys Met Ser Asp Thr Arg Gln His Tyr Ala Thr Leu Phe
                        340                 345                 350

Gln Ala Met His Asn Glu Thr Ala Ser His Asp Phe Lys Asn Leu Phe
                        355                 360                 365

Gln Phe Pro Arg Ile Tyr Asp Ala Leu Pro Val Pro Gln Glu Met Ser
                        370                 375                 380

Lys Leu Ser Asn Pro Lys Ile Pro Val Tyr Ile Asn Ile Cys Ser Ile
        385                 390                 395                 400

Pro Ser Arg Ile Ala Gln Leu Arg Arg Ile Ile Gly Ile Leu Lys Asn
                        405                 410                 415

Gln Cys Asp His Phe His Ile Tyr Leu Asp Gly Tyr Val Glu Ile Pro
                        420                 425                 430

Asp Phe Ile Lys Asn Leu Gly Asn Lys Ala Thr Val Val His Cys Lys
                        435                 440                 445

Asp Lys Asp Asn Ser Ile Arg Asp Asn Gly Lys Phe Ile Leu Leu Glu
                        450                 455                 460

Glu Leu Ile Glu Lys Asn Gln Asp Gly Tyr Tyr Ile Thr Cys Asp Asp
        465                 470                 475                 480

Asp Ile Ile Tyr Pro Ser Asp Tyr Ile Asn Thr Met Ile Lys Lys Leu
                        485                 490                 495
```

```
Asn Glu Tyr Asp Asp Lys Ala Val Ile Gly Leu His Gly Ile Leu Phe
                500                 505                 510
Pro Ser Arg Met Thr Lys Tyr Phe Ser Ala Asp Arg Leu Val Tyr Ser
            515                 520                 525
Phe Tyr Lys Pro Leu Glu Lys Asp Lys Ala Val Asn Val Leu Gly Thr
        530                 535                 540
Gly Thr Val Ser Phe Arg Val Ser Leu Phe Asn Gln Phe Ser Leu Ser
545                 550                 555                 560
Asp Phe Thr His Ser Gly Met Ala Asp Ile Tyr Phe Ser Leu Leu Cys
                565                 570                 575
Lys Lys Asn Asn Ile Leu Gln Ile Cys Ile Ser Arg Pro Ala Asn Trp
            580                 585                 590
Leu Thr Glu Asp Asn Arg Asp Ser Glu Thr Leu Tyr His Gln Tyr Arg
        595                 600                 605
Asp Asn Asp Glu Gln Gln Thr Gln Leu Ile Met Glu Asn Gly Pro Trp
    610                 615                 620
Gly Tyr Ser Ser Ile Tyr Pro Leu Val Lys Asn His Pro Lys Phe Thr
625                 630                 635                 640
Asp Leu Ile Pro Cys Leu Pro Phe Tyr Phe Leu
                645                 650

<210> SEQ ID NO 7
<211> LENGTH: 238
<212> TYPE: PRT
<213> ORGANISM: Escherichia coli

<400> SEQUENCE: 7

Met Ile Val Ala Asn Met Ser Ser Tyr Pro Pro Arg Lys Lys Glu Leu
1               5                   10                  15
Val His Ser Ile Gln Ser Leu His Ala Gln Val Asp Lys Ile Asn Leu
                20                  25                  30
Cys Leu Asn Glu Phe Glu Glu Ile Pro Glu Glu Leu Asp Gly Phe Ser
            35                  40                  45
Lys Leu Asn Pro Val Ile Pro Asp Lys Asp Tyr Lys Asp Val Gly Lys
        50                  55                  60
Phe Ile Phe Pro Cys Ala Lys Asn Asp Met Ile Val Leu Thr Asp Asp
65                  70                  75                  80
Asp Ile Ile Tyr Pro Pro Asp Tyr Val Glu Lys Met Leu Asn Phe Tyr
                85                  90                  95
Asn Ser Phe Ala Ile Phe Asn Cys Ile Val Gly Ile His Gly Cys Ile
            100                 105                 110
Tyr Ile Asp Ala Phe Asp Gly Asp Gln Ser Lys Arg Lys Val Phe Ser
        115                 120                 125
Phe Thr Gln Gly Leu Leu Arg Pro Arg Val Val Asn Gln Leu Gly Thr
    130                 135                 140
Gly Thr Val Phe Leu Lys Ala Asp Gln Leu Pro Ser Leu Lys Tyr Met
145                 150                 155                 160
Asp Gly Ser Gln Arg Phe Val Asp Val Arg Phe Ser Arg Tyr Met Leu
                165                 170                 175
Glu Asn Glu Ile Gly Met Ile Cys Val Pro Arg Glu Lys Asn Trp Leu
            180                 185                 190
Arg Glu Val Ser Ser Gly Ser Met Glu Gly Leu Trp Asn Thr Phe Thr
        195                 200                 205
Lys Lys Trp Pro Leu Asp Ile Ile Lys Glu Thr Gln Ala Ile Ala Gly
```

```
                210                 215                 220
Tyr Ser Lys Leu Asn Leu Glu Leu Val Tyr Asn Val Glu Gly
225                 230                 235

<210> SEQ ID NO 8
<211> LENGTH: 520
<212> TYPE: PRT
<213> ORGANISM: Escherichia coli

<400> SEQUENCE: 8

Met Asn Ala Glu Tyr Ile Asn Leu Val Glu Arg Lys Lys Leu Gly
1               5                   10                  15

Thr Asn Ile Gly Ala Leu Asp Phe Leu Leu Ser Ile His Lys Glu Lys
                20                  25                  30

Val Asp Leu Gln His Lys Asn Ser Pro Leu Lys Gly Asn Asp Asn Leu
            35                  40                  45

Ile His Lys Arg Ile Asn Glu Tyr Asp Asn Val Leu Glu Leu Ser Lys
        50                  55                  60

Asn Val Ser Ala Gln Asn Ser Gly Asn Glu Phe Ser Tyr Leu Leu Gly
65                  70                  75                  80

Tyr Ala Asp Ser Leu Arg Lys Val Gly Met Leu Asp Thr Tyr Ile Lys
                85                  90                  95

Ile Val Cys Tyr Leu Thr Ile Gln Ser Arg Tyr Phe Lys Asn Gly Glu
            100                 105                 110

Arg Val Lys Leu Phe Glu His Ile Ser Asn Ala Leu Arg Tyr Ser Arg
        115                 120                 125

Ser Asp Phe Leu Ile Asn Leu Ile Phe Glu Arg Tyr Ile Glu Tyr Ile
    130                 135                 140

Asn His Leu Lys Leu Ser Pro Lys Gln Lys Asp Phe Tyr Phe Cys Thr
145                 150                 155                 160

Lys Phe Ser Lys Phe His Asp Tyr Thr Lys Asn Gly Tyr Lys Tyr Leu
                165                 170                 175

Ala Phe Asp Asn Gln Ala Asp Ala Gly Tyr Gly Leu Thr Leu Leu Leu
            180                 185                 190

Asn Ala Asn Asp Asp Met Gln Asp Ser Tyr Asn Leu Leu Pro Glu Gln
        195                 200                 205

Glu Leu Phe Ile Cys Asn Ala Val Ile Asp Asn Met Asn Ile Tyr Arg
    210                 215                 220

Ser Gln Phe Asn Lys Cys Leu Arg Lys Tyr Asp Leu Ser Glu Ile Thr
225                 230                 235                 240

Asp Ile Tyr Pro Asn Lys Ile Ile Leu Gln Gly Ile Lys Phe Asp Lys
                245                 250                 255

Lys Lys Asn Val Tyr Gly Lys Asp Leu Val Ser Ile Ile Met Ser Val
            260                 265                 270

Phe Asn Ser Glu Asp Thr Ile Ala Tyr Ser Leu His Ser Leu Leu Asn
        275                 280                 285

Gln Thr Tyr Glu Asn Ile Glu Ile Leu Val Cys Asp Asp Cys Ser Ser
    290                 295                 300

Asp Lys Ser Leu Glu Ile Ile Lys Ser Ile Ala Tyr Ser Ser Ser Arg
305                 310                 315                 320

Val Lys Val Tyr Ser Ser Arg Lys Asn Gln Gly Pro Tyr Asn Ile Arg
                325                 330                 335

Asn Glu Leu Ile Lys Lys Ala His Gly Asn Phe Ile Thr Phe Gln Asp
            340                 345                 350
```

-continued

```
Ala Asp Asp Leu Ser His Pro Glu Arg Ile Gln Arg Gln Val Glu Val
        355                 360                 365

Leu Arg Asn Asn Lys Ala Val Ile Cys Met Ala Asn Trp Ile Arg Val
    370                 375                 380

Ala Ser Asn Gly Lys Ile Gln Phe Phe Tyr Asp Asp Lys Ala Thr Arg
385                 390                 395                 400

Met Ser Val Val Ser Ser Met Ile Lys Lys Asp Ile Phe Ala Thr Val
                405                 410                 415

Gly Gly Tyr Arg Gln Ser Leu Ile Gly Ala Asp Thr Glu Phe Tyr Glu
            420                 425                 430

Thr Val Ile Met Arg Tyr Gly Arg Glu Ser Ile Val Arg Leu Leu Gln
        435                 440                 445

Pro Leu Ile Leu Gly Leu Trp Gly Asp Ser Gly Leu Thr Arg Asn Lys
    450                 455                 460

Gly Thr Glu Ala Leu Pro Asp Gly Tyr Ile Ser Gln Ser Arg Arg Glu
465                 470                 475                 480

Tyr Ser Asp Ile Ala Ala Arg Gln Arg Val Leu Gly Lys Ser Ile Val
                485                 490                 495

Ser Asp Lys Asp Val Arg Gly Leu Leu Ser Arg Tyr Gly Leu Phe Lys
            500                 505                 510

Asp Val Ser Gly Ile Ile Glu Gln
        515                 520

<210> SEQ ID NO 9
<211> LENGTH: 563
<212> TYPE: PRT
<213> ORGANISM: Escherichia coli

<400> SEQUENCE: 9

Met Met Asn Lys Leu Val Leu Val Gly His Pro Gly Ser Lys Tyr Gln
1               5                   10                  15

Ile Val Glu His Phe Leu Lys Glu Ile Gly Met Asn Ser Pro Asn Tyr
            20                  25                  30

Ser Thr Ser Asn Lys Ile Ser Pro Glu Tyr Ile Thr Ala Ser Leu Cys
        35                  40                  45

Gln Phe Tyr Gln Thr Pro Glu Val Asn Asp Val Val Asp Glu Arg Glu
    50                  55                  60

Phe Ser Ala Val Gln Val Ser Thr Met Trp Asp Ser Met Val Leu Glu
65                  70                  75                  80

Leu Met Met Asn Asn Leu Asn Asn Lys Leu Trp Gly Trp Ala Asp Pro
                85                  90                  95

Ser Ile Ile Phe Phe Leu Asp Trp Lys Asn Ile Asp Lys Ser Ile
            100                 105                 110

Lys Phe Ile Met Ile Tyr Asp His Pro Lys Tyr Asn Leu Met Arg Ser
        115                 120                 125

Val Asn Asn Ala Pro Leu Ser Leu Asn Ile Asn Ser Val Asp Asn
    130                 135                 140

Trp Ile Ala Tyr Asn Lys Arg Leu Leu Asp Phe Phe Leu Glu Asn Lys
145                 150                 155                 160

Glu Arg Cys Val Leu Ile Asn Phe Glu Ala Phe Gln Ser Asn Lys Lys
                165                 170                 175

Asn Ile Ile Lys Pro Leu Ser Asn Ile Ile Lys Ile Asp Asn Leu Met
            180                 185                 190

Ser Ala His Tyr Lys Asn Ser Ile Leu Phe Asp Val Val Glu Asn Asn
        195                 200                 205
```

Asp Tyr Thr Lys Ser Asn Glu Ile Ala Leu Leu Glu Lys Tyr Thr Thr
    210                 215                 220

Leu Phe Ser Leu Ser Ala Asn Glu Thr Glu Ile Thr Phe Asn Asp Thr
225                 230                 235                 240

Lys Val Ser Glu Tyr Leu Val Ser Glu Leu Ile Lys Glu Arg Thr Glu
                245                 250                 255

Val Leu Lys Leu Tyr Asn Glu Leu Gln Ala Tyr Ala Asn Leu Pro Tyr
            260                 265                 270

Ile Glu Thr Ser Lys Asp Asn Val Ser Ala Glu Ala Leu Trp Glu
        275                 280                 285

Val Val Glu Glu Arg Asn Ser Ile Phe Asn Ile Val Ser His Leu Val
    290                 295                 300

Gln Glu Ser Lys Lys Asp Ala Asp Ile Glu Leu Thr Lys Ser Ile
305                 310                 315                 320

Phe Lys Lys Arg Gln Phe Leu Leu Asn Arg Ile Asn Glu Leu Lys
                325                 330                 335

Lys Glu Lys Glu Glu Val Ile Lys Leu Ser Lys Ile Asn His Asn Asp
            340                 345                 350

Val Val Arg Gln Glu Lys Tyr Pro Asp Asp Ile Glu Lys Lys Ile Asn
        355                 360                 365

Asp Ile Gln Lys Tyr Glu Glu Ile Ser Glu Lys Ser Lys Leu
    370                 375                 380

Thr Gln Ala Ile Ser Glu Lys Glu Gln Ile Leu Lys Gln Leu His Lys
385                 390                 395                 400

Tyr Glu Glu Glu Ile Ser Glu Lys Glu Ser Lys Leu Thr Gln Ala Ile
                405                 410                 415

Ser Glu Lys Glu Gln Ile Leu Lys Gln Leu His Ile Val Gln Glu Gln
            420                 425                 430

Leu Glu His Tyr Phe Ile Glu Asn Gln Glu Ile Lys Lys Lys Leu Pro
        435                 440                 445

Pro Val Leu Tyr Gly Ala Ala Glu Gln Ile Lys Gln Glu Leu Gly Tyr
    450                 455                 460

Arg Leu Gly Tyr Ile Ile Val Ser Tyr Ser Lys Ser Leu Lys Gly Ile
465                 470                 475                 480

Ile Thr Met Pro Phe Ala Leu Ile Arg Glu Cys Val Phe Glu Lys Lys
                485                 490                 495

Arg Lys Lys Ser Tyr Gly Val Asp Val Pro Leu Tyr Leu Tyr Ala Asp
            500                 505                 510

Ala Asp Lys Ala Glu Arg Val Lys Lys His Leu Ser Tyr Gln Leu Gly
        515                 520                 525

Gln Ala Ile Ile Ser Ser Ala Asn Ser Ile Phe Gly Phe Ile Thr Leu
    530                 535                 540

Pro Phe Lys Leu Ile Val Val Tyr Lys Tyr Arg Arg Ala Lys Ile
545                 550                 555                 560

Lys Gly Cys

<210> SEQ ID NO 10
<211> LENGTH: 150
<212> TYPE: PRT
<213> ORGANISM: Pasteurella multocida

<400> SEQUENCE: 10

Ala Pro Pro Leu Val Ser Ile Ile Met Thr Ser His Asn Thr Glu Lys
1               5                   10                  15

-continued

```
Phe Ile Glu Ala Ser Ile Asn Ser Leu Leu Leu Gln Thr Tyr Asn Asn
            20                  25                  30

Leu Glu Val Ile Val Val Asp Asp Tyr Ser Thr Asp Lys Thr Phe Gln
        35                  40                  45

Ile Ala Ser Arg Ile Ala Asn Ser Thr Ser Lys Val Lys Thr Phe Arg
    50                  55                  60

Leu Asn Ser Asn Leu Gly Thr Tyr Phe Ala Lys Asn Thr Gly Ile Leu
65                  70                  75                  80

Lys Ser Lys Gly Asp Ile Ile Phe Phe Gln Asp Ser Asp Asp Val Cys
                85                  90                  95

His His Glu Arg Ile Glu Arg Cys Val Asn Ala Leu Leu Ser Asn Lys
            100                 105                 110

Asp Asn Ile Ala Val Arg Cys Ala Tyr Ser Arg Ile Asn Leu Glu Thr
        115                 120                 125

Gln Asn Ile Ile Lys Val Asn Asp Asn Lys Tyr Lys Leu Gly Leu Ile
    130                 135                 140

Thr Leu Gly Val Tyr Arg
145                 150

<210> SEQ ID NO 11
<211> LENGTH: 99
<212> TYPE: PRT
<213> ORGANISM: Pasteurella multocida

<400> SEQUENCE: 11

Tyr Ile Thr Cys Asp Asp Asp Ile Arg Tyr Pro Ala Asp Tyr Ile Asn
1               5                   10                  15

Thr Met Ile Lys Lys Ile Asn Lys Tyr Asn Asp Lys Ala Ala Ile Gly
            20                  25                  30

Leu His Gly Val Ile Phe Pro Ser Arg Val Asn Lys Tyr Phe Ser Ser
        35                  40                  45

Asp Arg Ile Val Tyr Asn Phe Gln Lys Thr Phe Arg Lys Asp Thr Ala
    50                  55                  60

Val Asn Ile Leu Gly Thr Gly Thr Val Ala Phe Arg Val Ser Ile Phe
65                  70                  75                  80

Asn Lys Phe Ser Leu Ser Asp Phe Glu His Pro Gly Met Val Asp Ile
                85                  90                  95

Tyr Phe Ser

<210> SEQ ID NO 12
<211> LENGTH: 33
<212> TYPE: DNA
<213> ORGANISM: artificial sequence
<220> FEATURE:
<223> OTHER INFORMATION: sense primer
<220> FEATURE:
<221> NAME/KEY: misc_feature
<222> LOCATION: (9)..(9)
<223> OTHER INFORMATION: inosine
<220> FEATURE:
<221> NAME/KEY: misc_feature
<222> LOCATION: (12)..(12)
<223> OTHER INFORMATION: inosine
<220> FEATURE:
<221> NAME/KEY: misc_feature
<222> LOCATION: (18)..(18)
<223> OTHER INFORMATION: inosine
<220> FEATURE:
<221> NAME/KEY: misc_feature
<222> LOCATION: (24)..(24)
<223> OTHER INFORMATION: inosine
```

```
<220> FEATURE:
<221> NAME/KEY: misc_feature
<222> LOCATION: (27)..(27)
<223> OTHER INFORMATION: inosine

<400> SEQUENCE: 12
garttybtnm rngarggnaa rgcnytntay gay                                33

<210> SEQ ID NO 13
<211> LENGTH: 39
<212> TYPE: DNA
<213> ORGANISM: artificial sequence
<220> FEATURE:
<223> OTHER INFORMATION: antisense primer
<220> FEATURE:
<221> NAME/KEY: misc_feature
<222> LOCATION: (7)..(7)
<223> OTHER INFORMATION: inosine
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (16)..(16)
<223> OTHER INFORMATION: inosine
<220> FEATURE:
<221> NAME/KEY: misc_feature
<222> LOCATION: (22)..(22)
<223> OTHER INFORMATION: inosine
<220> FEATURE:
<221> NAME/KEY: misc_feature
<222> LOCATION: (25)..(25)
<223> OTHER INFORMATION: A or G or C or T

<400> SEQUENCE: 13
rcartanccn ccrtanccra answnggrtt rttrtartg                          39

<210> SEQ ID NO 14
<211> LENGTH: 28
<212> TYPE: DNA
<213> ORGANISM: artificial sequence
<220> FEATURE:
<223> OTHER INFORMATION: sense primer

<400> SEQUENCE: 14
atgagcttat ttaaacgtgc tactgagc                                      28

<210> SEQ ID NO 15
<211> LENGTH: 34
<212> TYPE: DNA
<213> ORGANISM: artificial sequence
<220> FEATURE:
<223> OTHER INFORMATION: antisense primer

<400> SEQUENCE: 15
tttactcgtt ataaaagat aaacacggaa taag                                34

<210> SEQ ID NO 16
<211> LENGTH: 30
<212> TYPE: DNA
<213> ORGANISM: artificial sequence
<220> FEATURE:
<223> OTHER INFORMATION: antisense primer

<400> SEQUENCE: 16
tatatttaca gcagtatcat tttctaaagg                                    30

<210> SEQ ID NO 17
```

-continued

```
<211> LENGTH: 501
<212> TYPE: PRT
<213> ORGANISM: Pasteurella multocida

<400> SEQUENCE: 17

Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Glu Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Phe Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
```

-continued

```
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Thr Phe Arg Lys
            500

<210> SEQ ID NO 18
<211> LENGTH: 1507
<212> TYPE: DNA
<213> ORGANISM: Pasteurella multocida
<400> SEQUENCE: 18
aatgagctta tttaaacgtg ctactgagct atttaagtca ggaaactata aagatgcact      60
aactctatat gaaaatatag ctaaaattta tggttcagaa agccttgtta aatataatat     120
tgatatatgt aaaaaaaata taacacaatc aaaaagtaat aaaatagaag aagataatat     180
ttctggagaa aacgaatttt cagtatcaat aaaagatcta tataacgaaa taagcaatag     240
tgaattaggg attacaaaag aaagactagg agcccccccct ctagtcagta ttataatgac    300
ttctcataat acagaaaaat tcattgaagc ctcaattaat tcactattat tgcaaacata     360
caataactta gaagttatcg ttgtagatga ttatagcaca gataaaacat ttcagatcgc     420
atccagaata gcaaactcta caagtaaagt aaaaacattc cgattaaact caaatctagg     480
gacatacttt gcgaaaaata caggaatttt aaagtctaaa ggagatatta ttttctttca     540
ggatagcgat gatgtatgtc accatgaaag aatcgaaaga tgtgttaatg cattattatc     600
gaataaagat aatatagctg ttagatgtgc atattctaga ataaatctag aaacacaaaa     660
tataataaaa gttaatgata ataaatacaa attaggatta ataactttag gcgtttatag     720
aaaagtattt aatgaaattg gtttttttaa ctgcacaacc aaagcatcgg atgatgaatt     780
ttatcataga ataattaaat actatggtaa aaataggata aataacttat ttctaccact     840
gtattataac acaatgcgtg aagattcatt attttctgat atggttgagt gggtagatga     900
aaataatata aagcaaaaaa cctctgatgc tagacaaaat tatctccatg aattccaaaa     960
aatacacaat gaaaggaaat ttaatgaatt aaaagagatt tttagctttc ctagaattca    1020
tgacgcctta cctatatcaa aagaaatgag taagctcagc aaccctaaaa ttcctgttta    1080
tataaatata tgctcaatac cttcaagaat aaaacaactt caatacacta ttggagtact    1140
aaaaaaccaa tgcgatcatt ttcatattta tcttgatgga tatccagaag tacctgattt    1200
tataaaaaaa ctagggaata aagcgaccgt tattaattgt caaaacaaaa atgagtctat    1260
tagagataat ggaaagttta ttctattaga aaaacttata aaggaaaata aagatggata    1320
ttatataact tgtgatgatg atatccggta tcctgctgac tacataaaca ctatgataaa    1380
aaaaattaat aaatacaatg ataaagcagc aattggatta catggtgtta tattcccaag    1440
```

```
tagagtcaac aagtatttt catcagacag aattgtctat aatttcaaa aaaccttag    1500 aaaatga                                                           1507
```

<210> SEQ ID NO 19
<211> LENGTH: 746
<212> TYPE: PRT
<213> ORGANISM: Homo sapiens

<400> SEQUENCE: 19

```
Met Gln Ala Lys Lys Arg Tyr Phe Ile Leu Leu Ser Ala Gly Ser Cys
1               5                   10                  15

Leu Ala Leu Leu Phe Tyr Phe Gly Gly Val Gln Phe Arg Ala Ser Arg
            20                  25                  30

Ser His Ser Arg Arg Glu Glu His Ser Gly Arg Asn Gly Leu His Gln
        35                  40                  45

Pro Ser Pro Asp His Phe Trp Pro Arg Phe Pro Asp Ala Leu Arg Pro
    50                  55                  60

Phe Phe Pro Trp Asp Gln Leu Glu Asn Glu Asp Ser Ser Val His Ile
65                  70                  75                  80

Ser Pro Arg Gln Lys Arg Asp Ala Asn Ser Ser Ile Tyr Lys Gly Lys
                85                  90                  95

Lys Cys Arg Met Glu Ser Cys Phe Asp Phe Thr Leu Cys Lys Lys Asn
            100                 105                 110

Gly Phe Lys Val Tyr Val Tyr Pro Gln Gln Lys Gly Glu Lys Ile Ala
        115                 120                 125

Glu Ser Tyr Gln Asn Ile Leu Ala Ala Ile Glu Gly Ser Arg Phe Tyr
    130                 135                 140

Thr Ser Asp Pro Ser Gln Ala Cys Leu Phe Val Leu Ser Leu Asp Thr
145                 150                 155                 160

Leu Asp Arg Asp Gln Leu Ser Pro Gln Tyr Val His Asn Leu Arg Ser
                165                 170                 175

Lys Val Gln Ser Leu His Leu Trp Asn Asn Gly Arg Asn His Leu Ile
            180                 185                 190

Phe Asn Leu Tyr Ser Gly Thr Trp Pro Asp Tyr Thr Glu Asp Val Gly
        195                 200                 205

Phe Asp Ile Gly Gln Ala Met Leu Ala Lys Ala Ser Ile Ser Thr Glu
    210                 215                 220

Asn Phe Arg Pro Asn Phe Asp Val Ser Ile Pro Leu Phe Ser Lys Asp
225                 230                 235                 240

His Pro Arg Thr Gly Gly Glu Arg Gly Phe Leu Lys Phe Asn Thr Ile
                245                 250                 255

Pro Pro Leu Arg Lys Tyr Met Leu Val Phe Lys Gly Lys Arg Tyr Leu
            260                 265                 270

Thr Gly Ile Gly Ser Asp Thr Arg Asn Ala Leu Tyr His Val His Asn
        275                 280                 285

Gly Glu Asp Val Leu Leu Leu Thr Thr Cys Lys His Gly Lys Asp Trp
    290                 295                 300

Gln Lys His Lys Asp Ser Arg Cys Asp Arg Asp Asn Thr Glu Tyr Glu
305                 310                 315                 320

Lys Tyr Asp Tyr Arg Glu Met Leu His Asn Ala Thr Phe Cys Leu Val
                325                 330                 335

Pro Arg Gly Arg Arg Leu Gly Ser Phe Arg Phe Leu Glu Ala Leu Gln
            340                 345                 350

Ala Ala Cys Val Pro Val Met Leu Ser Asn Gly Trp Glu Leu Pro Phe
```

-continued

```
                355                 360                 365
Ser Glu Val Ile Asn Trp Asn Gln Ala Ala Val Ile Gly Asp Glu Arg
    370                 375                 380

Leu Leu Leu Gln Ile Pro Ser Thr Ile Arg Ser Ile His Gln Asp Lys
385                 390                 395                 400

Ile Leu Ala Leu Arg Gln Gln Thr Gln Phe Leu Trp Glu Ala Tyr Phe
                405                 410                 415

Ser Ser Val Glu Lys Ile Val Leu Thr Thr Leu Glu Ile Ile Gln Asp
                420                 425                 430

Arg Ile Phe Lys His Ile Ser Arg Asn Ser Leu Ile Trp Asn Lys His
            435                 440                 445

Pro Gly Gly Leu Phe Val Leu Pro Gln Tyr Ser Ser Tyr Leu Gly Asp
        450                 455                 460

Phe Pro Tyr Tyr Tyr Ala Asn Leu Gly Leu Lys Pro Ser Lys Phe
465                 470                 475                 480

Thr Ala Val Ile His Ala Val Thr Pro Leu Val Ser Gln Ser Gln Pro
                485                 490                 495

Val Leu Lys Leu Leu Val Ala Ala Lys Ser Gln Tyr Cys Ala Gln
            500                 505                 510

Ile Ile Val Leu Trp Asn Cys Asp Lys Pro Leu Pro Ala Lys His Arg
        515                 520                 525

Trp Pro Ala Thr Ala Val Pro Val Ile Val Ile Glu Gly Glu Ser Lys
    530                 535                 540

Val Met Ser Ser Arg Phe Leu Pro Tyr Asp Asn Ile Ile Thr Asp Ala
545                 550                 555                 560

Val Leu Ser Leu Asp Glu Asp Thr Val Leu Ser Thr Thr Glu Val Asp
                565                 570                 575

Phe Ala Phe Thr Val Trp Gln Ser Phe Pro Glu Arg Ile Val Gly Tyr
                580                 585                 590

Pro Ala Arg Ser His Phe Trp Asp Asn Ser Lys Glu Arg Trp Gly Tyr
            595                 600                 605

Thr Ser Lys Trp Thr Asn Asp Tyr Ser Met Val Leu Thr Gly Ala Ala
        610                 615                 620

Ile Tyr His Lys Tyr Tyr His Tyr Leu Tyr Ser His Tyr Leu Pro Ala
625                 630                 635                 640

Ser Leu Lys Asn Met Val Asp Gln Leu Ala Asn Cys Glu Asp Ile Leu
                645                 650                 655

Met Asn Phe Leu Val Ser Ala Val Thr Lys Leu Pro Pro Ile Lys Val
                660                 665                 670

Thr Gln Lys Lys Gln Tyr Lys Glu Thr Met Met Gly Gln Thr Ser Arg
            675                 680                 685

Ala Ser Arg Trp Ala Asp Pro Asp His Phe Ala Gln Arg Gln Ser Cys
        690                 695                 700

Met Asn Thr Phe Ala Ser Trp Phe Gly Tyr Met Pro Leu Ile His Ser
705                 710                 715                 720

Gln Met Arg Leu Asp Pro Val Leu Phe Lys Asp Gln Val Ser Ile Leu
                725                 730                 735

Arg Lys Lys Tyr Arg Asp Ile Glu Arg Leu
            740                 745
```

<210> SEQ ID NO 20
<211> LENGTH: 718
<212> TYPE: PRT
<213> ORGANISM: Homo sapiens

<400> SEQUENCE: 20

Met Cys Ala Ser Val Lys Ser Asn Ile Arg Gly Pro Ala Leu Ile Pro
1               5                   10                  15

Arg Met Lys Thr Lys His Arg Ile Tyr Tyr Val Thr Leu Phe Ser Ile
            20                  25                  30

Val Leu Leu Gly Leu Ile Ala Thr Gly Met Phe Gln Phe Trp Pro His
        35                  40                  45

Ser Ile Glu Ser Ser Ser Asp Gly Gly Val Glu Lys Arg Ser Ile Arg
    50                  55                  60

Glu Val Pro Val Val Arg Leu Pro Thr Asp Ser Pro Ile Pro Glu Arg
65                  70                  75                  80

Gly Asp Leu Ser Cys Arg Met His Thr Cys Phe Asp Val Tyr Arg Cys
                85                  90                  95

Gly Phe Asn Pro Lys Asn Lys Ile Lys Val Tyr Ile Tyr Pro Leu Lys
            100                 105                 110

Lys Tyr Val Asp Asp Ala Gly Val Pro Val Ser Ser Ala Ile Ser Arg
        115                 120                 125

Glu Tyr Asn Glu Leu Leu Thr Ala Ile Ser Asp Ser Asp Tyr Tyr Thr
    130                 135                 140

Asp Asp Ile Asn Arg Ala Cys Leu Phe Val Pro Ser Ile Asp Val Leu
145                 150                 155                 160

Asn Gln Asn Pro Leu Arg Ile Lys Glu Thr Ala Gln Ala Leu Ala Gln
                165                 170                 175

Leu Ser Arg Trp Asp Arg Gly Thr Asn His Leu Leu Phe Asn Met Leu
            180                 185                 190

Pro Gly Ala Pro Pro Asp Tyr Asn Thr Ala Leu Asp Val Pro Arg Asp
        195                 200                 205

Arg Ala Leu Leu Ala Gly Gly Phe Ser Thr Trp Thr Tyr Arg Gln
    210                 215                 220

Gly Tyr Asp Val Ser Ile Pro Val Phe Ser Pro Leu Ser Ala Glu Met
225                 230                 235                 240

Ala Leu Pro Glu Lys Ala Pro Gly Pro Arg Arg Tyr Phe Leu Leu Ser
                245                 250                 255

Ser Gln Met Ala Ile His Pro Glu Tyr Arg Glu Glu Leu Glu Ala Leu
            260                 265                 270

Gln Ala Lys His Gln Glu Ser Val Leu Val Leu Asp Lys Cys Thr Asn
        275                 280                 285

Leu Ser Glu Gly Val Leu Ser Val Arg Lys Arg Cys His Gln His Gln
    290                 295                 300

Val Phe Asp Tyr Pro Gln Val Leu Gln Glu Ala Thr Phe Cys Thr Val
305                 310                 315                 320

Leu Arg Arg Ala Arg Leu Gly Gln Ala Val Leu Ser Asp Val Leu Gln
                325                 330                 335

Ala Gly Cys Val Pro Val Val Ile Ala Asp Ser Tyr Ile Leu Pro Phe
            340                 345                 350

Ser Glu Val Leu Asp Trp Lys Lys Ala Ser Val Val Val Pro Glu Glu
        355                 360                 365

Lys Met Ser Asp Val Tyr Ser Ile Leu Gln Asn Ile Pro Gln Arg Gln
    370                 375                 380

Ile Glu Glu Met Gln Arg Gln Ala Arg Trp Phe Trp Glu Ala Tyr Phe
385                 390                 395                 400

Gln Ser Ile Lys Ala Ile Ala Leu Ala Thr Leu Gln Ile Ile Asn Asp

```
                        405                 410                 415
Arg Ile Tyr Pro Tyr Ala Ala Ile Ser Tyr Glu Glu Trp Asn Asp Pro
                420                 425                 430

Pro Ala Val Lys Trp Ala Ser Val Ser Asn Pro Leu Phe Leu Pro Leu
            435                 440                 445

Ile Pro Pro Gln Ser Gln Gly Phe Thr Ala Ile Val Leu Thr Tyr Asp
        450                 455                 460

Arg Val Glu Ser Leu Phe Arg Val Ile Thr Glu Val Ser Lys Val Pro
465                 470                 475                 480

Ser Leu Ser Lys Leu Leu Val Val Trp Asn Asn Gln Asn Lys Asn Pro
                485                 490                 495

Pro Glu Glu Ser Leu Trp Pro Lys Ile Arg Val Pro Leu Lys Val Val
            500                 505                 510

Arg Thr Ala Glu Asn Lys Leu Ser Asn Arg Phe Phe Pro Tyr Asp Glu
        515                 520                 525

Ile Glu Thr Glu Ala Val Leu Ala Ile Asp Asp Ile Ile Met Leu
    530                 535                 540

Thr Ser Asp Glu Leu Gln Phe Gly Tyr Glu Val Trp Arg Glu Phe Pro
545                 550                 555                 560

Asp Arg Leu Val Gly Tyr Pro Gly Arg Leu His Leu Trp Asp His Glu
                565                 570                 575

Met Asn Lys Trp Lys Tyr Glu Ser Glu Trp Thr Asn Glu Val Ser Met
            580                 585                 590

Val Leu Thr Gly Ala Ala Phe Tyr His Lys Tyr Phe Asn Tyr Leu Tyr
        595                 600                 605

Thr Tyr Lys Met Pro Gly Asp Ile Lys Asn Trp Val Asp Ala His Met
    610                 615                 620

Asn Cys Glu Asp Ile Ala Met Asn Phe Leu Val Ala Asn Val Thr Gly
625                 630                 635                 640

Lys Ala Val Ile Lys Val Thr Pro Arg Lys Phe Lys Cys Pro Glu
                645                 650                 655

Cys Thr Ala Ile Asp Gly Leu Ser Leu Asp Gln Thr His Met Val Glu
            660                 665                 670

Arg Ser Glu Cys Ile Asn Lys Phe Ala Ser Val Phe Gly Thr Met Pro
        675                 680                 685

Leu Lys Val Val Glu His Arg Ala Asp Pro Val Leu Tyr Lys Asp Asp
    690                 695                 700

Phe Pro Glu Lys Leu Lys Ser Phe Pro Asn Ile Gly Ser Leu
705                 710                 715

<210> SEQ ID NO 21
<211> LENGTH: 78
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (6)..(6)
<223> OTHER INFORMATION: L or I
<220> FEATURE:
<221> NAME/KEY: MISC_FEATURE
<222> LOCATION: (8)..(11)
<223> OTHER INFORMATION: any amino acid
<220> FEATURE:
```

```
<221> NAME/KEY: MISC_FEATURE
<222> LOCATION: (14)..(14)
<223> OTHER INFORMATION: any amino acid
<220> FEATURE:
<221> NAME/KEY: MISC_FEATURE
<222> LOCATION: (15)..(16)
<223> OTHER INFORMATION: S or T
<220> FEATURE:
<221> NAME/KEY: MISC_FEATURE
<222> LOCATION: (18)..(18)
<223> OTHER INFORMATION: K or N
<220> FEATURE:
<221> NAME/KEY: MISC_FEATURE
<222> LOCATION: (19)..(19)
<223> OTHER INFORMATION: T or S
<220> FEATURE:
<221> NAME/KEY: MISC_FEATURE
<222> LOCATION: (20)..(26)
<223> OTHER INFORMATION: any amino acid
<220> FEATURE:
<221> NAME/KEY: MISC_FEATURE
<222> LOCATION: (29)..(29)
<223> OTHER INFORMATION: any amino acid
<220> FEATURE:
<221> NAME/KEY: MISC_FEATURE
<222> LOCATION: (30)..(33)
<223> OTHER INFORMATION: S or T
<220> FEATURE:
<221> NAME/KEY: MISC_FEATURE
<222> LOCATION: (34)..(34)
<223> OTHER INFORMATION: K or R
<220> FEATURE:
<221> NAME/KEY: MISC_FEATURE
<222> LOCATION: (36)..(36)
<223> OTHER INFORMATION: K or R
<220> FEATURE:
<221> NAME/KEY: MISC_FEATURE
<222> LOCATION: (37)..(42)
<223> OTHER INFORMATION: any amino acid
<220> FEATURE:
<221> NAME/KEY: MISC_FEATURE
<222> LOCATION: (44)..(44)
<223> OTHER INFORMATION: any amino acid
<220> FEATURE:
<221> NAME/KEY: MISC_FEATURE
<222> LOCATION: (46)..(46)
<223> OTHER INFORMATION: any amino acid
<220> FEATURE:
<221> NAME/KEY: MISC_FEATURE
<222> LOCATION: (48)..(63)
<223> OTHER INFORMATION: any amino acid
<220> FEATURE:
<221> NAME/KEY: MISC_FEATURE
<222> LOCATION: (67)..(67)
<223> OTHER INFORMATION: any amino acid
<220> FEATURE:
<221> NAME/KEY: MISC_FEATURE
<222> LOCATION: (70)..(70)
<223> OTHER INFORMATION: any amino acid
<220> FEATURE:
<221> NAME/KEY: MISC_FEATURE
<222> LOCATION: (71)..(71)
<223> OTHER INFORMATION: C or S
<220> FEATURE:
<221> NAME/KEY: MISC_FEATURE
<222> LOCATION: (73)..(73)
<223> OTHER INFORMATION: H or P
<220> FEATURE:
<221> NAME/KEY: MISC_FEATURE
<222> LOCATION: (77)..(77)
<223> OTHER INFORMATION: any amino acid

<400> SEQUENCE: 21

Gln Thr Tyr Xaa Asn Xaa Glu Xaa Xaa Xaa Asp Asp Xaa Xaa Xaa
1               5                   10                  15

Asp Xaa Xaa Xaa Xaa Xaa Xaa Xaa Xaa Xaa Ile Ala Xaa Xaa Xaa Xaa
            20                  25                  30
```

Xaa Xaa Val Xaa Xaa Xaa Xaa Xaa Xaa Asn Xaa Gly Xaa Tyr Xaa
         35                  40                  45

Xaa Xaa Xaa Xaa Xaa Xaa Xaa Xaa Xaa Xaa Xaa Xaa Xaa Xaa Phe
     50                  55                  60

Gln Asp Xaa Asp Asp Xaa Xaa His Xaa Glu Arg Ile Xaa Arg
 65              70                  75

<210> SEQ ID NO 22
<211> LENGTH: 82
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: K or R
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (8)..(18)
<223> OTHER INFORMATION: any amino acid
<220> FEATURE:
<221> NAME/KEY: MISC_FEATURE
<222> LOCATION: (19)..(19)
<223> OTHER INFORMATION: one two five amino acids
<220> FEATURE:
<221> NAME/KEY: MISC_FEATURE
<222> LOCATION: (24)..(24)
<223> OTHER INFORMATION: R or I
<220> FEATURE:
<221> NAME/KEY: MISC_FEATURE
<222> LOCATION: (27)..(27)
<223> OTHER INFORMATION: any amino acid
<220> FEATURE:
<221> NAME/KEY: MISC_FEATURE
<222> LOCATION: (30)..(32)
<223> OTHER INFORMATION: any amino acid
<220> FEATURE:
<221> NAME/KEY: MISC_FEATURE
<222> LOCATION: (34)..(72)
<223> OTHER INFORMATION: any amino acid
<220> FEATURE:
<221> NAME/KEY: MISC_FEATURE
<222> LOCATION: (73)..(73)
<223> OTHER INFORMATION: one to ten amino acids
<220> FEATURE:
<221> NAME/KEY: MISC_FEATURE
<222> LOCATION: (76)..(76)
<223> OTHER INFORMATION: any amino acid

<400> SEQUENCE: 22

Xaa Asp Xaa Gly Lys Phe Ile Xaa Xaa Xaa Xaa Xaa Xaa Xaa Xaa
 1               5                  10                  15

Xaa Xaa Xaa Asp Asp Asp Ile Xaa Tyr Pro Xaa Asp Tyr Xaa Xaa Xaa
         20                  25                  30

Met Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Val Asn Xaa Leu Gly Thr Gly
 65              70                  75                  80

Thr Val

What is claimed is:

1. A purified nucleic acid segment comprising a coding region encoding enzymatically active heparin synthase, wherein the heparin synthase is a single protein that is a dual-action catalyst that utilizes UDP-GlcUA and UDP-GlcNAc to synthesize heparin, and wherein the purified nucleic acid segment is at least one of:

(a) a purified nucleic acid segment encoding the *Pasteurella multocida* heparin synthase of SEQ ID NO:6;

(b) the purified nucleic acid segment of SEQ ID NO:5;

(c) a purified nucleic acid segment that is at least 90% identical to SEQ ID NO:5; and (d) a purified nucleic acid segment that hybridizes to a sequence, which is fully complementary to SEQ ID NO:6 under hybridization conditions of 5× Standard Saline Citrate (SSC) at 50° C. overnight, followed by washing in 0.1×SSC at room temperature for 10-60 minutes.

2. A recombinant vector selected from the group consisting of a plasmid, cosmid, phage, integrated cassette and virus vector, wherein the recombinant vector comprises:

a purified nucleic acid segment having a coding region encoding enzymatically active heparin synthase, wherein the heparin synthase is a single protein that is a dual-action catalyst that utilizes UDP-GlcUA and UDP-GlcNAc to synthesize heparin, and wherein the purified nucleic acid segment is at least one of:

(a) a purified nucleic acid segment encoding the *Pasteurella multocida* heparin synthase of SEQ ID NO:6;

(b) the purified nucleic acid segment of SEQ ID NO:5;

(c) a purified nucleic acid segment that is at least 90% identical to SEQ ID NO:5; and (d) a purified nucleic acid segment that hybridizes to a sequence, which is fully complementary to SEQ ID NO:6 under hybridization conditions of 5×SSC at 50° C. overnight, followed by washing in 0.1×SSC at room temperature for 10-60 minutes.

3. The recombinant vector of claim 2, wherein the plasmid further comprises an expression vector.

4. The recombinant vector of claim 3, wherein the expression vector comprises a promoter operatively linked to the enzymatically active heparin synthase coding region.

5. A recombinant host cell, wherein the recombinant host cell is electroporated, transformed, transfected, or transduced to introduce a recombinant vector into the host cell, wherein the recombinant vector comprises:

a purified nucleic acid segment having a coding region encoding enzymatically active heparin synthase, wherein the heparin synthase is a single protein that is a dual-action catalyst that utilizes UDP-GlcUA and UDP-GlcNAc to synthesize heparin, and wherein the purified nucleic acid segment is at least one of:

(a) a purified nucleic acid segment encoding the *Pasteurella multocida* heparin synthase of SEQ ID NO:6;

(b) the purified nucleic acid segment of SEQ ID NO:5;

(c) a purified nucleic acid segment that is at least 90% identical to SEQ ID NO:5; and (d) a purified nucleic acid segment that hybridizes to a sequence, which is fully complementary to SEQ ID NO:6 under hybridization conditions of 5×SSC at 50° C. overnight, followed by washing in 0.1×SSC at room temperature for 10-60 minutes.

6. The recombinant host cell of claim 5, wherein the host cell produces heparin.

7. The recombinant host cell of claim 6, wherein the heparin is unsulfated.

8. The recombinant host cell of claim 6, wherein the heparin is sulfated.

9. The recombinant host cell of claim 6, wherein the heparin is epimerized.

10. The recombinant host cell of claim 6, wherein the heparin is sulfated and epimerized.

11. The recombinant host cell of claim 5, wherein the recombinant host cell is a prokaryotic cell.

12. The recombinant host cell of claim 5, wherein the recombinant host cell is a eukaryotic cell.

* * * * *

UNITED STATES PATENT AND TRADEMARK OFFICE
CERTIFICATE OF CORRECTION

| | | |
|---|---|---|
| PATENT NO. | : 7,771,981 B2 | Page 1 of 42 |
| APPLICATION NO. | : 11/975811 | |
| DATED | : August 10, 2010 | |
| INVENTOR(S) | : Paul L. DeAngelis | |

It is certified that error appears in the above-identified patent and that said Letters Patent is hereby corrected as shown below:

Column 3, line 10: Delete "PgIA")" and replace with -- Pgla") --
Column 4, line 22: Delete "PgIA," and replace with -- PglA, --
Column 4, line 24: Delete "PgIA" and replace with -- PglA --
Column 4, line 26: Delete "PgIA" and replace with -- PglA --
Column 6, line 8: Delete "PgIA" and replace with -- PglA --
Column 6, line 17: Delete "PgIA," and replace with -- PglA, --
Column 6, line 57: Delete "PgIA." and replace with -- PglA. --
Column 6, line 61: Delete "PgIA," and replace with -- PglA, --
Column 7, line 2: Delete "PgIA." and replace with -- PglA. --
Column 7, line 14: Delete "PgIA" and replace with --PglA --
Column 7, line 32: Delete "PgIA" and replace with -- PglA --
Column 7, line 33: Delete "PgIA" and replace with -- PglA --
Column 8, line 43: Delete "PgIA—" and replace with -- PglA— --
Column 13, line 46: Delete "pgIA" and replace with -- pglA --
Column 13, line 62: Delete "xIHAS1" and replace with -- xlHAS1 --
Column 13, line 66: Delete "pgIA" and replace with -- pglA --
Column 14, line 47: Delete "PgIA." and replace with -- PglA. --
Column 15, line 14: Delete "PgIA," and replace with -- PglA, --
Column 15, line 18: Delete "PgIA" and replace with -- PglA --
Column 15, line 30: Delete "pgIA," and replace with -- pglA, --
Column 16, line 39: Delete "PgIA," and replace with -- PglA, --
Column 20, line 63: Delete "PgIA" and replace with -- PglA --
Column 20, line 66: Delete "PgIA" and replace with -- PglA --
Column 20, line 67: Delete "PgIA." and replace with -- PglA. --
Column 21, line 1: Delete "PgIA" and replace with -- PglA --
Column 21, line 4: Delete "PgIA" and replace with -- PglA --
Column 21, line 11: Delete "pgIA," and replace with -- pglA, --
Column 21, line 13: Delete "pgIA" and replace with -- pglA --
Column 21, line 15: Delete "pgIA" and replace with -- pglA --

Signed and Sealed this
Fifteenth Day of March, 2011

David J. Kappos
*Director of the United States Patent and Trademark Office*

Column 21, line 19: Delete "pgIA" and replace with -- pglA --
Column 21, line 24: Delete "pgIA." and replace with -- pglA. --
Column 21, line 25: Delete "pgIA" and replace with -- pglA --
Column 21, line 66: Delete "PgIA" and replace with -- PglA --
Column 22, line 4: Delete "PgIA" and replace with -- PglA --
Column 22, Table VI, line 10: After "recombinant" delete "pgIA" and replace with -- pglA --
Column 22, Table VI, under the heading of "CLONE" delete all four entries "PgIA-A2" "PgIA-A4" "PgIA-D4" and "PgIa-D7" and replace with -- PglA-A2 -- , -- PglA-A4 -- , -- PglA-D4 -- , and --PglA-D7 --
Column 22, line 20: Delete "PgIA," and replace with -- PglA, --
Column 22, line 23: Delete "PgIA" and replace with -- PglA --
Column 22, line 30: Delete "PgIA" and replace with -- PglA --
Column 22, Table VII, line 41: After "Panel I, Type A" delete "PgIA-A2" and replace with -- PglA-A2 --
Column 22, Table VII, line 54: After "Panel II, Type D" delete "PgIA-D7" and replace with -- PglA-D7 --
Column 23, line 1: Delete "PgIA" and replace with -- PglA --
Column 23, line 7: Delete "pgIA" and replace with -- pglA --
Column 23, line 19: Delete "pgIA" and replace with -- pglA --
Column 23, line 21: Delete "PgIA" and replace with -- PglA --
Column 23, Table IX, line 25: After "Activity of" delete "pgIA" and replace with -- pglA --
Column 23, Table IX, under the heading of "Membranes" delete the following six entries, "PgIA F 3", "PgIA F 4", "PgIA F 4", "PgIA F 18", "PgIA F 18", and "PgIA D 7" and replace with -- PglA F3 -- , -- PglA F4 -- , -- PglA F4 -- , -- PglA F18 -- , -- PglA F18 -- , and -- PglA D 7 --
Column 23, line 36: Delete "pgIA" and replace with -- pglA --
Column 23, line 44: Delete "pgIA" and replace with -- pglA --
Column 25, line 22: Delete "pgIA," and replace with -- pglA, --
Column 25, line 36: Delete "pgIA," and replace with -- pglA, --
Column 25, line 39: Delete "PgIA" and replace with -- PglA --
Column 25, line 47: Delete "pgIA" and replace with -- pglA --
Column 25, line 49: Delete "pgIA" and replace with -- pglA --
Column 25, line 53: Delete "pgIA" and replace with -- pglA --
Column 25, line 58: Delete "PgIA" and replace with -- PglA --
Column 27, line 18: Delete "PgIA" and replace with -- PglA --
Column 27, line 20: Delete "PgIA" and replace with -- PglA --
Column 27, line 30: Delete "PgIA," and replace with -- PglA, --
Column 27, line 33: Delete "PgIA" and replace with -- PglA --
Column 27, line 36: Delete "PgIA" and replace with -- PglA --
Column 27, line 44: Delete "pgIA" and replace with -- pglA --
Column 27, line 46: Delete "pgIA" and replace with -- pglA --

CERTIFICATE OF CORRECTION (continued)

U.S. Pat. No. 7,771,981 B2

In The Sequence Listing

Column 27-28, On the first line under

```
Thr Leu Gly Val Tyr Arg
145                 150

<210>  24
<211>  149
<212>  PRT
<213>  Escherichia coli

<400>  24

Gly Lys Asp Leu Val Ser Ile Ile Met Ser Val Phe Asn Ser Glu Asp
1               5                   10                  15

Thr Ile Ala Tyr Ser Leu His Ser Leu Leu Asn Gln Thr Tyr Glu Asn
            20                  25                  30

Ile Glu Ile Leu Val Cys Asp Asp Cys Ser Ser Asp Lys Ser Leu Glu
        35                  40                  45

Ile Ile Lys Ser Ile Ala Tyr Ser Ser Ser Arg Val Lys Val Tyr Ser
    50                  55                  60

Ser Arg Lys Asn Gln Gly Pro Tyr Asn Ile Arg Asn Glu Leu Ile Lys
65                  70                  75                  80

Lys Ala His Gly Asn Phe Ile Thr Phe Gln Asp Ala Asp Asp Leu Ser
                85                  90                  95

His Pro Glu Arg Ile Gln Arg Gln Val Glu Val Leu Arg Asn Asn Lys
            100                 105                 110

Ala Val Ile Cys Met Ala Asn Trp Ile Arg Val Ala Ser Asn Gly Lys
        115                 120                 125

Ile Gln Phe Phe Tyr Asp Asp Lys Ala Thr Arg Met Ser Val Val Ser
    130                 135                 140

Ser Met Ile Lys Lys
145

<210>  25
<211>  150
<212>  PRT
<213>  Artificial sequence

<220>
<223>  Consensus sequence from alignment in FIG. 1 of PmHS1 and KfiC

<220>
<221>  MISC_FEATURE
<222>  (1)..(3)
<223>  any amino acid

<220>
<221>  MISC_FEATURE
<222>  (10)..(10)
<223>  S or T

<220>
<221>  MISC_FEATURE
<222>  (11)..(12)
<223>  any amino acid

<220>
<221>  MISC_FEATURE
<222>  (14)..(14)
<223>  S or T

<220>
<221>  MISC_FEATURE
<222>  (16)..(17)
<223>  any amino acid

<220>
<221>  MISC_FEATURE
<222>  (19)..(20)
<223>  any amino acid
```

```
<220>
<221> MISC_FEATURE
<222> (22)..(23)
<223> any amino acid

<220>
<221> MISC_FEATURE
<222> (27)..(27)
<223> any amino acid

<220>
<221> MISC_FEATURE
<222> (31)..(31)
<223> any one of E, D, Q or N

<220>
<221> MISC_FEATURE
<222> (33)..(33)
<223> any amino acid

<220>
<221> MISC_FEATURE
<222> (35)..(35)
<223> I or V

<220>
<221> MISC_FEATURE
<222> (36)..(36)
<223> any amino acid

<220>
<221> MISC_FEATURE
<222> (38)..(38)
<223> any amino acid

<220>
<221> MISC_FEATURE
<222> (41)..(41)
<223> any amino acid

<220>
<221> MISC_FEATURE
<222> (43)..(43)
<223> S or T
```

```
<220>
<221> MISC_FEATURE
<222> (46)..(46)
<223> S or T

<220>
<221> MISC_FEATURE
<222> (47)..(47)
<223> any amino acid

<220>
<221> MISC_FEATURE
<222> (48)..(48)
<223> any one of E, D, Q or N

<220>
<221> MISC_FEATURE
<222> (50)..(52)
<223> any amino acid

<220>
<221> MISC_FEATURE
<222> (55)..(55)
<223> any amino acid

<220>
<221> MISC_FEATURE
<222> (57)..(57)
<223> S or T

<220>
<221> MISC_FEATURE
<222> (59)..(59)
<223> K or R

<220>
<221> MISC_FEATURE
<222> (62)..(62)
<223> any amino acid

<220>
<221> MISC_FEATURE
<222> (63)..(63)
<223> any one of F, Y or W

<220>
<221> MISC_FEATURE
<222> (64)..(67)
<223> any amino acid

<220>
<221> MISC_FEATURE
<222> (69)..(69)
<223> any amino acid

<220>
<221> MISC_FEATURE
<222> (71)..(71)
<223> any amino acid

<220>
<221> MISC_FEATURE
<222> (73)..(75)
<223> any amino acid

<220>
<221> MISC_FEATURE
<222> (77)..(78)
<223> any amino acid

<220>
<221> MISC_FEATURE
<222> (80)..(80)
<223> any amino acid

<220>
<221> MISC_FEATURE
<222> (82)..(83)
<223> any amino acid

<220>
<221> MISC_FEATURE
<222> (85)..(85)
<223> any one of E, D, Q or N

<220>
<221> MISC_FEATURE
<222> (86)..(86)
<223> any amino acid
```

```
<220>
<221> MISC_FEATURE
<222> (88)..(88)
<223> any amino acid

<220>
<221> MISC_FEATURE
<222> (92)..(92)
<223> any amino acid

<220>
<221> MISC_FEATURE
<222> (95)..(96)
<223> any amino acid

<220>
<221> MISC_FEATURE
<222> (98)..(98)
<223> any amino acid

<220>
<221> MISC_FEATURE
<222> (102)..(102)
<223> any one of E, D, Q, or N

<220>
<221> MISC_FEATURE
<222> (104)..(104)
<223> any amino acid

<220>
<221> MISC_FEATURE
<222> (106)..(106)
<223> any one of E, D, Q, or N

<220>
<221> MISC_FEATURE
<222> (107)..(107)
<223> any amino acid

<220>
<221> MISC_FEATURE
<222> (109)..(110)
<223> any amino acid

<220>
<221> MISC_FEATURE
<222> (113)..(114)
<223> any amino acid

<220>
<221> MISC_FEATURE
<222> (116)..(122)
<223> any amino acid

<220>
<221> MISC_FEATURE
<222> (124)..(124)
<223> I or V

<220>
<221> MISC_FEATURE
<222> (125)..(126)
<223> any amino acid

<220>
<221> MISC_FEATURE
<222> (127)..(127)
<223> any one of E, D, Q, or N

<220>
<221> MISC_FEATURE
<222> (128)..(134)
<223> any amino acid

<220>
<221> MISC_FEATURE
<222> (135)..(135)
<223> any one of E, D, Q or N

<220>
<221> MISC_FEATURE
<222> (137)..(139)
<223> any amino acid

<220>
<221> MISC_FEATURE
<222> (140)..(140)
<223> K or R
```

```
<220>
<221> MISC_FEATURE
<222> (141)..(141)
<223> L or M

<220>
<221> MISC_FEATURE
<222> (142)..(143)
<223> any amino acid

<220>
<221> MISC_FEATURE
<222> (144)..(144)
<223> I or V

<220>
<221> MISC_FEATURE
<222> (145)..(145)
<223> S or T

<220>
<221> MISC_FEATURE
<222> (146)..(147)
<223> any amino acid

<220>
<221> MISC_FEATURE
<222> (148)..(148)
<223> I or V

<220>
<221> MISC_FEATURE
<222> (149)..(149)
<223> any amino acid

<220>
<221> MISC_FEATURE
<222> (150)..(150)
<223> K or R

<400> 25
```

Xaa Xaa Xaa Leu Val Ser Ile Ile Met Xaa Xaa Xaa Asn Xaa Glu Xaa
1               5                   10                  15

Xaa Ile Xaa Xaa Ser Xaa Xaa Ser Leu Leu Xaa Gln Thr Tyr Xaa Asn
        20              25                  30

Xaa Glu Xaa Xaa Val Xaa Asp Asp Xaa Ser Xaa Asp Lys Xaa Xaa Xaa
        35              40              45

Ile Xaa Xaa Xaa Ile Ala Xaa Ser Xaa Ser Xaa Val Lys Xaa Xaa Xaa
    50              55              60

Xaa Xaa Xaa Asn Xaa Gly Xaa Tyr Xaa Xaa Asn Xaa Xaa Ile Xaa
65              70              75              80

Lys Xaa Xaa Gly Xaa Xaa Ile Xaa Phe Gln Asp Xaa Asp Xaa Xaa
            85              90              95

His Xaa Glu Arg Ile Xaa Arg Xaa Val Xaa Xaa Leu Xaa Xaa Asn Lys
        100             105                 110

Xaa Xaa Ile Xaa Xaa Xaa Xaa Xaa Xaa Arg Xaa Xaa Xaa Xaa Xaa
        115             120                 125

Xaa Xaa Xaa Xaa Xaa Xaa Xaa Asp Xaa Xaa Xaa Xaa Xaa Xaa Xaa
    130             135             140

Xaa Xaa Xaa Xaa Xaa Xaa
145             150

<210> 26
<211> 99
<212> PRT
<213> Pasteurella multocida

<400> 26

Tyr Ile Thr Cys Asp Asp Asp Ile Arg Tyr Pro Ala Asp Tyr Ile Asn
1               5                   10                  15

Thr Met Ile Lys Lys Ile Asn Lys Tyr Asn Asp Lys Ala Ala Ile Gly
            20                  25                  30

Leu His Gly Val Ile Phe Pro Ser Arg Val Asn Lys Tyr Phe Ser Ser
        35                  40                  45

Asp Arg Ile Val Tyr Asn Phe Gln Lys Thr Phe Arg Lys Asp Thr Ala
    50                  55                  60

Val Asn Ile Leu Gly Thr Gly Thr Val Ala Phe Arg Val Ser Ile Phe
65                  70                  75                  80

Asn Lys Phe Ser Leu Ser Asp Phe Glu His Pro Gly Met Val Asp Ile
                85                  90                  95

Tyr Phe Ser

<210> 27
<211> 98
<212> PRT
<213> Escherichia coli

<400> 27

Ile Val Leu Thr Asp Asp Asp Ile Ile Tyr Pro Pro Asp Tyr Val Glu
1               5                   10                  15

Lys Met Leu Asn Phe Tyr Asn Ser Phe Ala Ile Phe Asn Cys Ile Val
            20                  25                  30

Gly Ile His Gly Cys Ile Tyr Ile Asp Ala Phe Asp Gly Asp Gln Ser
        35                  40                  45

Lys Arg Lys Val Phe Ser Phe Thr Gln Gly Leu Leu Arg Pro Arg Val
    50                  55                  60

Val Asn Gln Leu Gly Thr Gly Thr Val Phe Leu Lys Ala Asp Gln Leu
65                  70                  75                  80

Pro Ser Leu Lys Tyr Met Asp Gly Ser Gln Arg Phe Val Asp Val Arg
                85                  90                  95

Phe Ser

<210> 28
<211> 100
<212> PRT
<213> Artificial Sequence

<220>
<223> Consensus sequence from alignment of HS2 and KfiA of FIG. 1

<220>
<221> MISC_FEATURE
<222> (1)..(1)
<223> any amino acid

```
<220>
<221> MISC_FEATURE
<222> (2)..(2)
<223> I or V

<220>
<221> MISC_FEATURE
<222> (3)..(4)
<223> any amino acid

<220>
<221> MISC_FEATURE
<222> (9)..(9)
<223> any amino acid

<220>
<221> MISC_FEATURE
<222> (12)..(12)
<223> any amino acid

<220>
<221> MISC_FEATURE
<222> (15)..(15)
<223> I or V

<220>
<221> MISC_FEATURE
<222> (16)..(16)
<223> any one of E, D, Q or N

<220>
<221> MISC_FEATURE
<222> (17)..(17)
<223> any amino acid

<220>
<221> MISC_FEATURE
<222> (19)..(22)
<223> any amino acid

<220>
<221> MISC_FEATURE
<222> (24)..(24)
<223> any amino acid

<220>
<221> MISC_FEATURE
<222> (25)..(25)
<223> any one of F, Y or W

<220>
<221> MISC_FEATURE
<222> (26)..(31)
<223> any amino acid

<220>
<221> MISC_FEATURE
<222> (32)..(32)
<223> I or V

<220>
<221> MISC_FEATURE
<222> (34)..(34)
<223> any amino acid

<220>
<221> MISC_FEATURE
<222> (37)..(37)
<223> any amino acid

<220>
<221> MISC_FEATURE
<222> (39)..(39)
<223> any one of F, Y or W

<220>
<221> MISC_FEATURE
<222> (40)..(43)
<223> any amino acid

<220>
<221> MISC_FEATURE
<222> (44)..(44)
<223> any one of E, D, Q or N
```

```
<220>
<221> MISC_FEATURE
<222> (45)..(48)
<223> any amino acid

<220>
<221> MISC_FEATURE
<222> (50)..(50)
<223> any amino acid

<220>
<221> MISC_FEATURE
<222> (52)..(52)
<223> any amino acid

<220>
<221> MISC_FEATURE
<222> (54)..(54)
<223> any one of F, Y or W

<220>
<221> MISC_FEATURE
<222> (55)..(55)
<223> any amino acid

<220>
<221> MISC_FEATURE
<222> (57)..(61)
<223> any amino acid

<220>
<221> MISC_FEATURE
<222> (62)..(62)
<223> K or R

<220>
<221> MISC_FEATURE
<222> (63)..(65)
<223> any amino acid

<220>
<221> MISC_FEATURE
<222> (68)..(68)
<223> any amino acid

<220>
<221> MISC_FEATURE
<222> (75)..(76)
<223> any amino acid

<220>
<221> MISC_FEATURE
<222> (77)..(77)
<223> K or R

<220>
<221> MISC_FEATURE
<222> (78)..(87)
<223> any amino acid

<220>
<221> MISC_FEATURE
<222> (89)..(94)
<223> any amino acid

<220>
<221> MISC_FEATURE
<222> (97)..(97)
<223> I or V

<220>
<221> MISC_FEATURE
<222> (98)..(98)
<223> any amino acid

<400> 28

Xaa Xaa Xaa Xaa Asp Asp Asp Ile Xaa Tyr Pro Xaa Asp Tyr Xaa Xaa
 1               5                  10                  15

Xaa Met Xaa Xaa Xaa Xaa Asn Xaa Xaa Xaa Xaa Xaa Xaa Xaa Xaa Xaa
            20                  25                  30

Gly Xaa His Gly Xaa Ile Xaa Xaa Xaa Xaa Xaa Xaa Xaa Xaa Xaa
            35                  40                  45
```

```
Ser Xaa Arg Xaa Val Xaa Xaa Phe Xaa Xaa Xaa Xaa Xaa Xaa Xaa
    50          55                  60

Xaa Val Asn Xaa Leu Gly Thr Gly Thr Val Xaa Xaa Xaa Xaa Xaa
65              70                  75                  80

Xaa Xaa Xaa Xaa Xaa Xaa Xaa Asp Xaa Xaa Xaa Xaa Xaa Val Asp
            85              90              95

Xaa Xaa Phe Ser
            100

<210>  29
<211>  259
<212>  PRT
<213>  Escherichia coli

<400>  29

Gly Lys Asp Leu Val Ser Ile Ile Met Ser Val Phe Asn Ser Glu Asp
1               5                   10                  15

Thr Ile Ala Tyr Ser Leu His Ser Leu Leu Asn Gln Thr Tyr Glu Asn
            20              25                  30

Ile Glu Ile Leu Val Cys Asp Asp Cys Ser Ser Asp Lys Ser Leu Glu
        35              40              45

Ile Ile Lys Ser Ile Ala Tyr Ser Ser Ser Arg Val Lys Val Tyr Ser
    50              55              60

Ser Arg Lys Asn Gln Gly Pro Tyr Asn Ile Arg Asn Glu Leu Ile Lys
65              70              75              80

Lys Ala His Gly Asn Phe Ile Thr Phe Gln Asp Ala Asp Asp Leu Ser
            85              90              95

His Pro Glu Arg Ile Gln Arg Gln Val Glu Val Leu Arg Asn Asn Lys
            100             105             110

Ala Val Ile Cys Met Ala Asn Trp Ile Arg Val Ala Ser Asn Gly Lys
            115             120             125

Ile Gln Phe Phe Tyr Asp Asp Lys Ala Thr Arg Met Ser Val Val Ser
    130             135             140

Ser Met Ile Lys Lys Asp Ile Phe Ala Thr Val Gly Gly Tyr Arg Gln
145             150             155             160

Ser Leu Ile Gly Ala Asp Thr Glu Phe Tyr Glu Thr Val Ile Met Arg
            165             170             175

Tyr Gly Arg Glu Ser Ile Val Arg Leu Leu Gln Pro Leu Ile Leu Gly
            180             185             190

Leu Trp Gly Asp Ser Gly Leu Thr Arg Asn Lys Gly Thr Glu Ala Leu
    195             200             205

Pro Asp Gly Tyr Ile Ser Gln Ser Arg Arg Glu Tyr Ser Asp Ile Ala
    210             215             220

Ala Arg Gln Arg Val Leu Gly Lys Ser Ile Ser Asp Lys Asp Val
225             230             235             240

Arg Gly Leu Leu Ser Arg Tyr Gly Leu Phe Lys Asp Val Ser Gly Ile
            245             250             255

Ile Glu Gln
```

<210> 30
<211> 261
<212> PRT
<213> Pasteurella multocida

<400> 30

Ala Pro Pro Leu Val Ser Ile Ile Met Thr Ser His Asn Thr Glu Lys
1               5                   10                  15

Phe Ile Glu Ala Ser Ile Asn Ser Leu Leu Gln Thr Tyr Asn Asn
            20              25              30

Leu Glu Val Ile Val Val Asp Asp Tyr Ser Thr Asp Lys Thr Phe Gln
            35              40              45

Ile Ala Ser Arg Ile Ala Asn Ser Thr Ser Lys Val Lys Thr Phe Arg
    50              55                  60

Leu Asn Ser Asn Leu Gly Thr Tyr Phe Ala Lys Asn Thr Gly Ile Leu
65              70              75                  80

Lys Ser Lys Gly Asp Ile Ile Phe Phe Gln Asp Ser Asp Asp Val Cys
                85                  90              95

His His Glu Arg Ile Glu Arg Cys Val Asn Ala Leu Leu Ser Asn Lys
                100             105             110

Asp Asn Ile Ala Val Arg Cys Ala Tyr Ser Arg Ile Asn Leu Glu Thr
            115             120             125

Gln Asn Ile Ile Lys Val Asn Asp Asn Lys Tyr Lys Leu Gly Leu Ile
    130             135             140

Thr Leu Gly Val Tyr Arg Lys Val Phe Asn Glu Ile Gly Phe Phe Asn
145             150             155             160

Cys Thr Thr Lys Ala Ser Asp Asp Glu Phe Tyr His Arg Ile Ile Lys
                165             170             175

Tyr Tyr Gly Lys Asn Arg Ile Asn Asn Leu Phe Leu Pro Leu Tyr Tyr
            180             185             190

Asn Thr Met Arg Glu Asp Ser Leu Phe Ser Asp Met Val Glu Trp Val
        195             200             205

Asp Glu Asn Asn Ile Lys Gln Lys Thr Ser Asp Ala Arg Gln Asn Tyr
    210             215             220

Leu His Glu Phe Gln Lys Ile His Asn Glu Arg Lys Leu Asn Glu Leu
225             230             235             240

Lys Glu Ile Phe Ser Phe Pro Arg Ile His Asp Ala Leu Pro Ile Ser
                245             250             255

Lys Glu Met Ser Lys
            260

<210> 31
<211> 255
<212> PRT
<213> Pasteurella multocida

<400> 31

Ile Pro Val Tyr Ile Asn Ile Cys Ser Ile Pro Ser Arg Ile Lys Gln
1               5                   10              15

Leu Gln Tyr Thr Ile Gly Val Leu Lys Asn Gln Cys Asp His Phe His

```
                        20                   25                   30
Ile Tyr Leu Asp Gly Tyr Pro Glu Val Pro Asp Phe Ile Lys Lys Leu
        35                   40                   45

Gly Asn Lys Ala Thr Val Ile Asn Cys Gln Asn Lys Asn Glu Ser Ile
    50                  55                  60

Arg Asp Asn Gly Lys Phe Ile Leu Leu Glu Lys Leu Ile Lys Glu Asn
65                  70                  75                  80

Lys Asp Gly Tyr Tyr Ile Thr Cys Asp Asp Ile Arg Tyr Pro Ala
                85                  90                  95

Asp Tyr Ile Asn Thr Met Ile Lys Lys Ile Asn Lys Tyr Asn Asp Lys
            100                 105                 110

Ala Ala Ile Gly Leu His Gly Val Ile Phe Pro Ser Arg Val Asn Lys
        115                 120                 125

Tyr Phe Ser Ser Asp Arg Ile Val Tyr Asn Phe Gln Lys Pro Leu Glu
    130                 135                 140

Asn Asp Thr Ala Val Asn Ile Leu Gly Thr Gly Thr Val Ala Phe Arg
145                 150                 155                 160

Val Ser Ile Phe Asn Lys Phe Ser Leu Ser Asp Phe Glu His Pro Gly
                165                 170                 175

Met Val Asp Ile Tyr Phe Ser Ile Leu Cys Lys Lys Asn Asn Ile Leu
            180                 185                 190

Gln Val Cys Ile Ser Arg Pro Ser Asn Trp Leu Thr Glu Asp Asn Lys
        195                 200                 205

Asn Thr Glu Thr Leu Phe His Glu Phe Gln Asn Arg Asp Glu Ile Gln
    210                 215                 220

Ser Lys Leu Ile Ile Ser Asn Asn Pro Trp Gly Tyr Ser Ser Ile Tyr
225                 230                 235                 240

Pro Leu Leu Asn Asn Asn Ala Asn Tyr Ser Glu Leu Ile Pro Cys
                245                 250                 255
```

<210> 32
<211> 264
<212> PRT
<213> Artificial Sequence

<220>
<223> consensus sequence from alignment of KfiC, HSA1, KfiA, HSA2 of FIG. 4A <220>
<221> MISC_FEATURE
<222> (1)..(2)
<223> any amino acid <220>
<221> MISC_FEATURE
<222> (4)..(4)
<223> any amino acid <220>
<221> MISC_FEATURE
<222> (6)..(6)
<223> any amino acid

```
<220>
<221>  MISC_FEATURE
<222>  (9)..(9)
<223>  any amino acid

<220>
<221>  MISC_FEATURE
<222>  (11)..(11)
<223>  any amino acid

<220>
<221>  MISC_FEATURE
<222>  (13)..(13)
<223>  any amino acid

<220>
<221>  MISC_FEATURE
<222>  (15)..(15)
<223>  any amino acid

<220>
<221>  MISC_FEATURE
<222>  (17)..(17)
<223>  any amino acid

<220>
<221>  MISC_FEATURE
<222>  (19)..(19)
<223>  any amino acid

<220>
<221>  MISC_FEATURE
<222>  (23)..(23)
<223>  any amino acid

<220>
<221>  MISC_FEATURE
<222>  (26)..(26)
<223>  any amino acid

<220>
<221>  MISC_FEATURE
<222>  (29)..(30)
<223>  any amino acid

<220>
<221>  MISC_FEATURE
<222>  (31)..(31)
<223>  E, N or D

<220>
<221>  MISC_FEATURE
<222>  (32)..(32)
<223>  any amino acid

<220>
<221>  MISC_FEATURE
<222>  (34)..(34)
<223>  any amino acid

<220>
<221>  MISC_FEATURE
<222>  (36)..(36)
<223>  any amino acid

<220>
<221>  MISC_FEATURE
<222>  (38)..(41)
<223>  any amino acid

<220>
<221>  MISC_FEATURE
<222>  (43)..(43)
<223>  any amino acid

<220>
<221>  MISC_FEATURE
<222>  (45)..(46)
<223>  any amino acid

<220>
<221>  MISC_FEATURE
<222>  (48)..(50)
<223>  any amino acid

<220>
<221>  MISC_FEATURE
<222>  (52)..(53)
<223>  any amino acid
```

```
<220>
<221>  MISC_FEATURE
<222>  (55)..(55)
<223>  any amino acid

<220>
<221>  MISC_FEATURE
<222>  (58)..(64)
<223>  any amino acid

<220>
<221>  MISC_FEATURE
<222>  (66)..(66)
<223>  any amino acid

<220>
<221>  MISC_FEATURE
<222>  (68)..(68)
<223>  N or D

<220>
<221>  MISC_FEATURE
<222>  (69)..(69)
<223>  any amino acid

<220>
<221>  misc_feature
<222>  (70)..(70)
<223>  Xaa can be any naturally occurring amino acid <220>
<221>  MISC_FEATURE
<222>  (72)..(72)
<223>  Y or F <220>
<221>  misc_feature
<222>  (73)..(73)
<223>  Xaa can be any naturally occurring amino acid <220>
<221>  MISC_FEATURE
<222>  (74)..(77)
<223>  any amino acid <220>
<221>  misc_feature
<222>  (78)..(78)
<223>  Xaa can be any naturally occurring amino acid <220>
<221>  MISC_FEATURE
<222>  (81)..(81)
<223>  any amino acid <220>
<221>  misc_feature
<222>  (82)..(82)
<223>  Xaa can be any naturally occurring amino acid <220>
<221>  MISC_FEATURE
<222>  (84)..(84)
<223>  any amino acid <220>
<221>  misc_feature
<222>  (85)..(85)
<223>  Xaa can be any naturally occurring amino acid <220>
<221>  MISC_FEATURE
<222>  (86)..(86)
<223>  any amino acid <220>
<221>  misc_feature
<222>  (87)..(87)
<223>  Xaa can be any naturally occurring amino acid <220>
<221>  MISC_FEATURE
<222>  (88)..(90)
<223>  any amino acid <220>
<221>  misc_feature
<222>  (91)..(91)
<223>  Xaa can be any naturally occurring amino acid
```

```
<220>
<221>  MISC_FEATURE
<222>  (95)..(95)
<223>  any amino acid

<220>
<221>  misc_feature
<222>  (96)..(96)
<223>  Xaa can be any naturally occurring amino acid <220>
<221>  MISC_FEATURE
<222>  (99)..(99)
<223>  E or D <220>
<221>  misc_feature
<222>  (100)..(100)
<223>  Xaa can be any naturally occurring amino acid <220>
<221>  MISC_FEATURE
<222>  (101)..(101)
<223>  I or V <220>
<221>  MISC_FEATURE
<222>  (102)..(102)
<223>  Q, E or N <220>
<221>  MISC_FEATURE
<222>  (103)..(103)
<223>  any amino acid <220>
<221>  misc_feature
<222>  (104)..(104)
<223>  Xaa can be any naturally occurring amino acid <220>
<221>  MISC_FEATURE
<222>  (105)..(105)
<223>  any amino acid
```

```
<220>
<221> misc_feature
<222> (106)..(106)
<223> Xaa can be any naturally occurring amino acid <220>
<221> MISC_FEATURE
<222> (107)..(108)
<223> any amino acid <220>
<221> misc_feature
<222> (109)..(109)
<223> Xaa can be any naturally occurring amino acid <220>
<221> MISC_FEATURE
<222> (111)..(112)
<223> any amino acid <220>
<221> misc_feature
<222> (113)..(113)
<223> Xaa can be any naturally occurring amino acid <220>
<221> MISC_FEATURE
<222> (114)..(115)
<223> any amino acid <220>
<221> misc_feature
<222> (116)..(116)
<223> Xaa can be any naturally occurring amino acid <220>
<221> MISC_FEATURE
<222> (117)..(118)
<223> any amino acid <220>
<221> misc_feature
<222> (119)..(119)
<223> Xaa can be any naturally occurring amino acid
```

```
<220>
<221>  MISC_FEATURE
<222>  (120)..(120)
<223>  any amino acid

<220>
<221>  misc_feature
<222>  (121)..(121)
<223>  Xaa can be any naturally occurring amino acid <220>
<221>  MISC_FEATURE
<222>  (123)..(123)
<223>  any amino acid <220>
<221>  MISC_FEATURE
<222>  (124)..(124)
<223>  V or I <220>
<221>  MISC_FEATURE
<222>  (125)..(129)
<223>  any amino acid <220>
<221>  misc_feature
<222>  (130)..(130)
<223>  xaa can be any naturally occurring amino acid <220>
<221>  MISC_FEATURE
<222>  (131)..(132)
<223>  any amino acid <220>
<221>  misc_feature
<222>  (133)..(133)
<223>  Xaa can be any naturally occurring amino acid <220>
<221>  MISC_FEATURE
<222>  (134)..(134)
<223>  any amino acid
```

```
<220>
<221> misc_feature
<222> (135)..(135)
<223> Xaa can be any naturally occurring amino acid <220>
<221> MISC_FEATURE
<222> (140)..(141)
<223> any amino acid <220>
<221> misc_feature
<222> (142)..(142)
<223> Xaa can be any naturally occurring amino acid <220>
<221> MISC_FEATURE
<222> (144)..(148)
<223> any amino acid <220>
<221> misc_feature
<222> (149)..(149)
<223> Xaa can be any naturally occurring amino acid <220>
<221> MISC_FEATURE
<222> (150)..(151)
<223> any amino acid <220>
<221> misc_feature
<222> (152)..(152)
<223> Xaa can be any naturally occurring amino acid <220>
<221> MISC_FEATURE
<222> (155)..(155)
<223> any amino acid <220>
<221> misc_feature
<222> (156)..(156)
<223> Xaa can be any naturally occurring amino acid
```

```
<220>
<221> MISC_FEATURE
<222> (158)..(159)
<223> any amino acid

<220>
<221> misc_feature
<222> (160)..(160)
<223> Xaa can be any naturally occurring amino acid <220>
<221> MISC_FEATURE
<222> (164)..(167)
<223> any amino acid <220>
<221> misc_feature
<222> (168)..(168)
<223> Xaa can be any naturally occurring amino acid <220>
<221> MISC_FEATURE
<222> (169)..(169)
<223> any amino acid <220>
<221> misc_feature
<222> (170)..(170)
<223> Xaa can be any naturally occurring amino acid <220>
<221> MISC_FEATURE
<222> (171)..(175)
<223> any amino acid <220>
<221> misc_feature
<222> (176)..(176)
<223> Xaa can be any naturally occurring amino acid <220>
<221> MISC_FEATURE
<222> (178)..(183)
<223> any amino acid
```

```
<220>
<221> misc_feature
<222> (184)..(184)
<223> Xaa can be any naturally occurring amino acid <220>
<221> MISC_FEATURE
<222> (186)..(187)
<223> any amino acid <220>
<221> misc_feature
<222> (188)..(188)
<223> Xaa can be any naturally occurring amino acid <220>
<221> MISC_FEATURE
<222> (190)..(190)
<223> any amino acid <220>
<221> misc_feature
<222> (191)..(191)
<223> Xaa can be any naturally occurring amino acid <220>
<221> MISC_FEATURE
<222> (192)..(194)
<223> any amino acid <220>
<221> misc_feature
<222> (195)..(195)
<223> Xaa can be any naturally occurring amino acid <220>
<221> MISC_FEATURE
<222> (196)..(196)
<223> any amino acid <220>
<221> misc_feature
<222> (197)..(197)
<223> Xaa can be any naturally occurring amino acid
```

CERTIFICATE OF CORRECTION (continued)
U.S. Pat. No. 7,771,981 B2

```
<220>
<221> MISC_FEATURE
<222> (198)..(200)
<223> any amino acid

<220>
<221> misc_feature
<222> (201)..(201)
<223> Xaa can be any naturally occurring amino acid <220>
<221> MISC_FEATURE
<222> (202)..(203)
<223> any amino acid <220>
<221> misc_feature
<222> (204)..(204)
<223> Xaa can be any naturally occurring amino acid <220>
<221> MISC_FEATURE
<222> (205)..(206)
<223> any amino acid <220>
<221> MISC_FEATURE
<222> (207)..(207)
<223> E or N <220>
<221> misc_feature
<222> (208)..(208)
<223> Xaa can be any naturally occurring amino acid <220>
<221> MISC_FEATURE
<222> (210)..(210)
<223> any amino acid <220>
<221> MISC_FEATURE
<222> (211)..(211)
<223> D or E
```

```
<220>
<221> MISC_FEATURE
<222> (212)..(212)
<223> any amino acid

<220>
<221> misc_feature
<222> (213)..(213)
<223> Xaa can be any naturally occurring amino acid <220>
<221> MISC_FEATURE
<222> (214)..(214)
<223> any amino acid <220>
<221> misc_feature
<222> (215)..(215)
<223> Xaa can be any naturally occurring amino acid <220>
<221> MISC_FEATURE
<222> (216)..(216)
<223> any amino acid <220>
<221> misc_feature
<222> (217)..(217)
<223> Xaa can be any naturally occurring amino acid <220>
<221> MISC_FEATURE
<222> (218)..(218)
<223> any amino acid <220>
<221> misc_feature
<222> (219)..(219)
<223> Xaa can be any naturally occurring amino acid <220>
<221> MISC_FEATURE
<222> (220)..(220)
<223> any amino acid
```

```
<220>
<221> misc_feature
<222> (221)..(221)
<223> Xaa can be any naturally occurring amino acid <220>
<221> MISC_FEATURE
<222> (222)..(224)
<223> any amino acid <220>
<221> misc_feature
<222> (225)..(225)
<223> Xaa can be any naturally occurring amino acid <220>
<221> MISC_FEATURE
<222> (226)..(230)
<223> any amino acid <220>
<221> misc_feature
<222> (231)..(231)
<223> Xaa can be any naturally occurring amino acid <220>
<221> MISC_FEATURE
<222> (232)..(234)
<223> any amino acid <220>
<221> misc_feature
<222> (235)..(235)
<223> Xaa can be any naturally occurring amino acid <220>
<221> MISC_FEATURE
<222> (236)..(238)
<223> any amino acid <220>
<221> misc_feature
<222> (239)..(239)
<223> Xaa can be any naturally occurring amino acid <220>
<221> MISC_FEATURE
<222> (240)..(242)
<223> any amino acid <220>
<221> misc_feature
<222> (243)..(243)
<223> Xaa can be any naturally occurring amino acid <220>
<221> MISC_FEATURE
<222> (247)..(247)
<223> any amino acid <220>
<221> misc_feature
<222> (248)..(248)
<223> Xaa can be any naturally occurring amino acid <220>
<221> MISC_FEATURE
<222> (252)..(253)
<223> any amino acid <220>
<221> misc_feature
<222> (254)..(254)
<223> Xaa can be any naturally occurring amino acid <220>
<221> MISC_FEATURE
<222> (255)..(257)
<223> any amino acid <220>
<221> misc_feature
<222> (258)..(258)
<223> Xaa can be any naturally occurring amino acid <220>
<221> MISC_FEATURE
<222> (260)..(263)
<223> any amino acid
```

<220>
<221> misc_feature
<222> (264)..(264)
<223> Xaa can be any naturally occurring amino acid

<400> 32

Xaa Xaa Pro Xaa Val Xaa Asn Ile Xaa Ser Xaa Pro Xaa Arg Xaa Lys
1               5                   10                  15

Xaa Leu Xaa Tyr Ser Ile Xaa Ser Leu Xaa Asn Gln Xaa Xaa Xaa Xaa
            20                  25                  30

Ile Xaa Ile Xaa Leu Xaa Xaa Xaa Xaa Glu Xaa Pro Xaa Xaa Leu Xaa
        35                  40                  45

Xaa Xaa Ser Xaa Xaa Ala Xaa Val Ile Xaa Xaa Xaa Xaa Xaa Xaa
    50                  55                  60

Ser Xaa Lys Xaa Xaa Xaa Gly Lys Xaa Ile Xaa Xaa Xaa Xaa Leu Ile
65              70                  75                      80

Lys Xaa Ala Lys Xaa Asp Xaa Ile Xaa Xaa Xaa Asp Asp Asp Ile Xaa
                85              90                  95

Tyr Pro Pro Xaa Tyr Xaa Xaa Xaa Met Xaa Asn Xaa Xaa Asn Ser Xaa
            100                 105                 110

Xaa Asp Xaa Xaa Ala Xaa Xaa Gly Xaa His Gly Xaa Xaa Xaa Xaa Xaa
        115                 120                 125

Xaa Xaa Asn Xaa Xaa Phe Xaa Ser Asp Arg Lys Val Xaa Xaa Ser Phe
130                 135                 140

Xaa Xaa Xaa Xaa Xaa Lys Xaa Xaa Val Val Asn Xaa Leu Gly Xaa Xaa
145                 150                 155                 160

Thr Gly Thr Val Xaa Xaa Xaa Asp Xaa Phe Xaa Xaa Xaa Xaa Xaa
                165                 170                 175

Met Asp Xaa Xaa Xaa Xaa Xaa Val Asp Xaa Xaa Phe Ser Xaa Tyr
        180                 185                 190

Xaa Xaa Xaa Asn Xaa Ile Xaa Xaa Xaa Cys Xaa Xaa Arg Xaa Xaa Xaa
        195                 200                 205

Trp Leu Xaa Xaa Xaa Asn Xaa Lys Xaa Ser Xaa Glu Xaa Leu Xaa Xaa
210                 215                 220

Xaa Phe Xaa Xaa Xaa Xaa Xaa Leu Xaa Xaa Ile Xaa Xaa Xaa Asn
225                 230                 235                 240

Xaa Xaa Xaa Gly Tyr Ser Ser Xaa Tyr Pro Leu Leu Xaa Xaa Asn Xaa
            245                 250                 255

Xaa Xaa Ser Glu Xaa Xaa Xaa Xaa
            260

<210> 33
<211> 626
<212> PRT
<213> Artificial Sequence

<220>
<223> consensus sequence of alignment of pmHS, pglA and DcbF of FIG. 48

<220>
<221> misc_feature

```
<222>  (1)..(1)
<223>  Xaa can be any naturally occurring amino acid

<220>
<221>  misc_feature
<222>  (9)..(9)
<223>  Xaa can be any naturally occurring amino acid <220>
<221>  misc_feature
<222>  (32)..(35)
<223>  Xaa can be any naturally occurring amino acid <220>
<221>  misc_feature
<222>  (50)..(51)
<223>  Xaa can be any naturally occurring amino acid <220>
<221>  misc_feature
<222>  (58)..(58)
<223>  Xaa can be any naturally occurring amino acid <220>
<221>  misc_feature
<222>  (72)..(76)
<223>  Xaa can be any naturally occurring amino acid <220>
<221>  misc_feature
<222>  (87)..(87)
<223>  Xaa can be any naturally occurring amino acid <220>
<221>  misc_feature
<222>  (91)..(91)
<223>  Xaa can be any naturally occurring amino acid <220>
<221>  misc_feature
<222>  (135)..(135)
<223>  Xaa can be any naturally occurring amino acid <220>
<221>  misc_feature
<222>  (137)..(137)
<223>  Xaa can be any naturally occurring amino acid <220>
<221>  misc_feature
<222>  (148)..(148)
<223>  Xaa can be any naturally occurring amino acid <220>
<221>  misc_feature
<222>  (213)..(213)
<223>  Xaa can be any naturally occurring amino acid <220>
<221>  misc_feature
<222>  (235)..(235)
<223>  Xaa can be any naturally occurring amino acid <220>
<221>  misc_feature
<222>  (253)..(253)
<223>  Xaa can be any naturally occurring amino acid <220>
<221>  misc_feature
<222>  (270)..(270)
<223>  Xaa can be any naturally occurring amino acid <220>
<221>  misc_feature
<222>  (280)..(280)
<223>  Xaa can be any naturally occurring amino acid <220>
<221>  misc_feature
<222>  (297)..(297)
<223>  Xaa can be any naturally occurring amino acid
```

```
<220>
<221>  misc_feature
<222>  (307)..(307)
<223>  Xaa can be any naturally occurring amino acid <220>
<221>  misc_feature
<222>  (309)..(309)
<223>  Xaa can be any naturally occurring amino acid <220>
<221>  misc_feature
<222>  (336)..(336)
<223>  Xaa can be any naturally occurring amino acid <220>
<221>  misc_feature
<222>  (338)..(338)
<223>  Xaa can be any naturally occurring amino acid <220>
<221>  misc_feature
<222>  (341)..(341)
<223>  Xaa can be any naturally occurring amino acid <220>
<221>  misc_feature
<222>  (354)..(354)
<223>  Xaa can be any naturally occurring amino acid <220>
<221>  misc_feature
<222>  (388)..(388)
<223>  Xaa can be any naturally occurring amino acid <220>
<221>  misc_feature
<222>  (406)..(406)
<223>  Xaa can be any naturally occurring amino acid <220>
<221>  misc_feature
<222>  (420)..(420)
<223>  Xaa can be any naturally occurring amino acid <220>
<221>  misc_feature
<222>  (424)..(424)
<223>  Xaa can be any naturally occurring amino acid <220>
<221>  misc_feature
<222>  (426)..(427)
<223>  Xaa can be any naturally occurring amino acid <220>
<221>  misc_feature
<222>  (475)..(475)
<223>  Xaa can be any naturally occurring amino acid <220>
<221>  misc_feature
<222>  (485)..(485)
<223>  Xaa can be any naturally occurring amino acid <220>
<221>  misc_feature
<222>  (512)..(512)
<223>  Xaa can be any naturally occurring amino acid <220>
<221>  misc_feature
<222>  (516)..(516)
<223>  Xaa can be any naturally occurring amino acid <220>
<221>  misc_feature
<222>  (523)..(523)
<223>  Xaa can be any naturally occurring amino acid <220>
<221>  misc_feature
<222>  (528)..(528)
<223>  Xaa can be any naturally occurring amino acid <220>
<221>  misc_feature
<222>  (531)..(531)
<223>  Xaa can be any naturally occurring amino acid
```

```
<220>
<221>  misc_feature
<222>  (538)..(538)
<223>  Xaa can be any naturally occurring amino acid <220>
<221>  misc_feature
<222>  (540)..(540)
<223>  Xaa can be any naturally occurring amino acid <220>
<221>  misc_feature
<222>  (543)..(543)
<223>  Xaa can be any naturally occurring amino acid <220>
<221>  misc_feature
<222>  (549)..(549)
<223>  Xaa can be any naturally occurring amino acid <220>
<221>  misc_feature
<222>  (559)..(559)
<223>  Xaa can be any naturally occurring amino acid <220>
<221>  misc_feature
<222>  (565)..(565)
<223>  Xaa can be any naturally occurring amino acid <220>
<221>  misc_feature
<222>  (573)..(575)
<223>  Xaa can be any naturally occurring amino acid <220>
<221>  misc_feature
<222>  (579)..(579)
<223>  Xaa can be any naturally occurring amino acid <220>
<221>  misc_feature
<222>  (581)..(585)
<223>  Xaa can be any naturally occurring amino acid <220>
<221>  misc_feature
<222>  (588)..(588)
<223>  Xaa can be any naturally occurring amino acid <220>
<221>  misc_feature
<222>  (590)..(591)
<223>  Xaa can be any naturally occurring amino acid <220>
<221>  misc_feature
<222>  (594)..(595)
<223>  Xaa can be any naturally occurring amino acid <220>
<221>  misc_feature
<222>  (597)..(597)
<223>  Xaa can be any naturally occurring amino acid <220>
<221>  misc_feature
<222>  (608)..(609)
<223>  Xaa can be any naturally occurring amino acid <220>
<221>  misc_feature
<222>  (611)..(616)
<223>  Xaa can be any naturally occurring amino acid <220>
<221>  misc_feature
<222>  (622)..(622)
<223>  Xaa can be any naturally occurring amino acid <220>
<221>  misc_feature
<222>  (625)..(626)
<223>  Xaa can be any naturally occurring amino acid
```

<400> 33

Xaa Ser Leu Phe Lys Arg Ala Thr Xaa Leu Phe Lys Ser Gly Asn Tyr
1               5                   10                  15

Lys Asp Ala Leu Thr Leu Tyr Glu Asn Ile Ala Lys Ile Tyr Gly Xaa
                20                  25                  30

Xaa Xaa Xaa Ser Glu Ser Leu Val Lys Tyr Asn Ile Asp Ile Cys Lys
            35                  40                  45

Lys Xaa Xaa Ile Thr Gln Ser Lys Ser Xaa Lys Ile Glu Glu Asp Asn
        50                  55                  60

Ile Ser Gly Glu Asn Lys Phe Xaa Xaa Xaa Xaa Ser Val Ser Ile
65                  70                  75                  80

Lys Asp Leu Tyr Asn Glu Xaa Ser Asn Ser Xaa Leu Gly Ile Thr Lys
                85                  90                  95

Glu Arg Leu Gly Ala Pro Pro Leu Val Ser Ile Ile Met Thr Ser His
            100                 105                 110

Asn Thr Glu Lys Phe Ile Glu Ala Ser Ile Asn Ser Leu Leu Leu Gln
        115                 120                 125

Thr Tyr Asn Asn Leu Glu Xaa Ile Xaa Val Asp Asp Tyr Ser Thr Asp
    130                 135                 140

Lys Thr Phe Xaa Ile Ala Ser Arg Ile Ala Asn Ser Thr Ser Lys Val
145                 150                 155                 160

Lys Thr Phe Arg Leu Asn Ser Asn Leu Gly Thr Tyr Phe Ala Lys Asn
                165                 170                 175

Thr Gly Ile Leu Lys Ser Lys Gly Asp Ile Ile Phe Phe Gln Asp Ser
            180                 185                 190

Asp Asp Val Cys His His Glu Arg Ile Glu Arg Cys Val Asn Ala Leu
        195                 200                 205

Leu Ser Asn Lys Xaa Asn Ile Ala Val Arg Cys Ala Tyr Ser Ile Asn
210                 215                 220

Leu Glu Thr Gln Asn Ile Ile Lys Val Asn Xaa Asn Lys Tyr Lys Leu
225                 230                 235                 240

Gly Leu Ile Thr Leu Gly Val Tyr Arg Lys Val Phe Xaa Glu Ile Gly
            245                 250                 255

Phe Phe Asn Cys Thr Thr Lys Ala Ser Asp Asp Glu Phe Xaa His Arg
        260                 265                 270

Ile Ile Lys Tyr Tyr Gly Lys Xaa Arg Ile Asn Asn Leu Phe Leu Pro
    275                 280                 285

Leu Tyr Tyr Asn Thr Met Arg Glu Xaa Ser Leu Phe Ser Asp Met Val
290                 295                 300

Glu Trp Xaa Asp Xaa Asn Asn Ile Lys Gln Lys Thr Ser Asp Ala Arg
305                 310                 315                 320

Gln Asn Tyr Leu His Glu Phe Gln Lys Ile His Asn Glu Arg Lys Xaa
            325                 330                 335

Asn Xaa Leu Lys Xaa Ile Phe Ser Phe Pro Arg Ile His Asp Ala Leu
        340                 345                 350

Pro Xaa Ser Lys Glu Met Ser Lys Leu Ser Asn Pro Lys Ile Pro Val
      355             360             365

Tyr Ile Asn Ile Cys Ser Ile Pro Ser Arg Ile Lys Gln Leu Gln Tyr
    370             375             380

Thr Ile Gly Xaa Leu Lys Asn Gln Cys Asp His Phe His Ile Tyr Leu
385             390             395                         400

Asp Gly Tyr Pro Glu Xaa Pro Asp Phe Ile Lys Lys Leu Gly Asn Lys
                405             410                 415

Ala Thr Val Xaa Asn Cys Gln Xaa Lys Xaa Xaa Ser Ile Arg Asp Asn
            420             425                 430

Gly Lys Phe Ile Leu Leu Glu Lys Leu Ile Lys Glu Asn Lys Asp Gly
        435             440             445

Tyr Tyr Ile Thr Cys Asp Asp Asp Ile Arg Tyr Pro Ala Asp Tyr Ile
    450             455             460

Asn Thr Met Ile Lys Lys Ile Asn Lys Tyr Xaa Asp Lys Ala Ala Ile
465             470             475                         480

Gly Leu His Gly Xaa Ile Phe Pro Ser Arg Val Asn Lys Tyr Phe Ser
            485             490             495

Ser Asp Arg Ile Val Tyr Asn Phe Gln Lys Pro Leu Glu Lys Asp Xaa
            500             505             510

Ala Val Asn Xaa Leu Gly Thr Gly Thr Val Xaa Phe Arg Val Ser Xaa
            515             520             525

Phe Asn Xaa Phe Ser Leu Ser Asp Phe Xaa His Xaa Gly Met Xaa Asp
530             535             540

Ile Tyr Phe Ser Xaa Leu Cys Lys Lys Asn Asn Ile Leu Gln Xaa Cys
545             550             555                         560

Ile Ser Arg Pro Xaa Asn Trp Leu Thr Glu Asp Asn Xaa Xaa Xaa Glu
            565             570             575

Thr Leu Xaa His Xaa Xaa Xaa Xaa Xaa Asp Glu Xaa Gln Xaa Xaa Leu
            580             585             590

Ile Xaa Xaa Asn Xaa Pro Trp Gly Tyr Ser Ser Ile Tyr Pro Leu Xaa
        595             600             605

Xaa Asn Xaa Xaa Xaa Xaa Xaa Xaa Leu Ile Pro Cys Leu Xaa Phe Tyr
    610             615             620

Xaa Xaa
625

<210> 34
<211> 625
<212> PRT
<213> Artificial Sequence

<220>
<223> Consensus sequence of alignment of PmHS clones A2 and B10, PglA and DcbF of FIG. 4C <220>
<221> MISC_FEATURE
<222> (1)..(1)
<223> M or L

```
<220>
<221> MISC_FEATURE
<222> (9)..(9)
<223> any one of N, D, Q, E, B or Z

<220>
<221> MISC_FEATURE
<222> (32)..(35)
<223> any amino acid

<220>
<221> MISC_FEATURE
<222> (50)..(50)
<223> any amino acid

<220>
<221> MISC_FEATURE
<222> (51)..(51)
<223> any one of N, D, Q, E, B or Z

<220>
<221> MISC_FEATURE
<222> (58)..(58)
<223> any one of N, D, Q, E, B or Z

<220>
<221> MISC_FEATURE
<222> (72)..(76)
<223> any amino acid

<220>
<221> MISC_FEATURE
<222> (87)..(87)
<223> I or V

<220>
<221> MISC_FEATURE
<222> (91)..(91)
<223> any one of N, D, Q, E, B or Z

<220>
<221> MISC_FEATURE
<222> (135)..(135)
<223> I ro V

<220>
<221> MISC_FEATURE
<222> (137)..(137)
<223> I ro V

<220>
<221> MISC_FEATURE
<222> (148)..(148)
<223> any one of N, D, Q, E, B or Z

<220>
<221> MISC_FEATURE
<222> (213)..(213)
<223> any one of N, D, Q, E, B or Z

<220>
<221> MISC_FEATURE
<222> (236)..(236)
<223> any one of N, D, Q, E, B or Z

<220>
<221> MISC_FEATURE
<222> (254)..(254)
<223> any one of N, D, Q, E, B or Z

<220>
<221> MISC_FEATURE
<222> (271)..(271)
<223> Y or F

<220>
<221> MISC_FEATURE
<222> (281)..(281)
<223> any one of N, D, Q, E, B or Z

<220>
<221> MISC_FEATURE
<222> (298)..(298)
<223> any one of N, D, Q, E, B or Z

<220>
<221> MISC_FEATURE
<222> (308)..(308)
<223> I or V
```

CERTIFICATE OF CORRECTION (continued)

U.S. Pat. No. 7,771,981 B2

```
<220>
<221> MISC_FEATURE
<222> (310)..(310)
<223> any one of N, D, Q, E, B or Z <220>
<221> MISC_FEATURE
<222> (337)..(337)
<223> any amino acid <220>
<221> MISC_FEATURE
<222> (339)..(339)
<223> any one of N, D, Q, E, B or Z <220>
<221> MISC_FEATURE
<222> (342)..(342)
<223> any one of N, D, Q, E, B or Z <220>
<221> MISC_FEATURE
<222> (355)..(355)
<223> I or V <220>
<221> MISC_FEATURE
<222> (389)..(389)
<223> I or V <220>
<221> MISC_FEATURE
<222> (407)..(407)
<223> I or V <220>
<221> MISC_FEATURE
<222> (421)..(421)
<223> I or V <220>
<221> MISC_FEATURE
<222> (425)..(425)
<223> any one of N, D, Q, E, B or Z <220>
<221> MISC_FEATURE
<222> (427)..(428)
<223> any one of N, D, Q, E, B or Z <220>
<221> MISC_FEATURE
<222> (476)..(476)
<223> any one of N, D, Q, E, B or Z <220>
<221> MISC_FEATURE
<222> (486)..(486)
<223> I or V <220>
<221> MISC_FEATURE
<222> (513)..(513)
<223> any amino acid <220>
<221> MISC_FEATURE
<222> (517)..(517)
<223> any amino acid <220>
<221> MISC_FEATURE
<222> (524)..(524)
<223> any amino acid <220>
<221> MISC_FEATURE
<222> (529)..(529)
<223> any amino acid <220>
<221> MISC_FEATURE
<222> (532)..(532)
<223> any amino acid <220>
<221> MISC_FEATURE
<222> (539)..(539)
<223> any amino acid
```

```
<220>
<221> MISC_FEATURE
<222> (541)..(541)
<223> any amino acid

<220>
<221> MISC_FEATURE
<222> (544)..(544)
<223> any amino acid

<220>
<221> MISC_FEATURE
<222> (550)..(550)
<223> any amino acid

<220>
<221> MISC_FEATURE
<222> (560)..(560)
<223> any amino acid

<220>
<221> MISC_FEATURE
<222> (566)..(566)
<223> any amino acid

<220>
<221> MISC_FEATURE
<222> (574)..(576)
<223> any amino acid

<220>
<221> MISC_FEATURE
<222> (580)..(580)
<223> any amino acid

<220>
<221> MISC_FEATURE
<222> (582)..(586)
<223> any amino acid

<220>
<221> MISC_FEATURE
<222> (589)..(589)
<223> any amino acid

<220>
<221> MISC_FEATURE
<222> (591)..(592)
<223> any amino acid

<220>
<221> MISC_FEATURE
<222> (595)..(596)
<223> any amino acid

<220>
<221> MISC_FEATURE
<222> (598)..(598)
<223> any amino acid

<220>
<221> MISC_FEATURE
<222> (609)..(610)
<223> any amino acid

<220>
<221> MISC_FEATURE
<222> (612)..(617)
<223> any amino acid

<220>
<221> MISC_FEATURE
<222> (623)..(623)
<223> any amino acid

<400> 34
```

Xaa Ser Leu Phe Lys Arg Ala Thr Xaa Leu Phe Lys Ser Gly Asn Tyr
1               5                   10                  15

Lys Asp Ala Leu Thr Leu Tyr Glu Asn Ile Ala Lys Ile Tyr Gly Xaa
            20                  25                  30

Xaa Xaa Xaa Ser Glu Ser Leu Val Lys Tyr Asn Ile Asp Ile Cys Lys
        35                  40                  45

Lys Xaa Xaa Ile Thr Gln Ser Lys Ser Xaa Lys Ile Glu Glu Asp Asn
50                  55                  60

Ile Ser Gly Glu Asn Lys Phe Xaa Xaa Xaa Xaa Ser Val Ser Ile
65              70              75                  80

Lys Asp Leu Tyr Asn Glu Xaa Ser Asn Ser Xaa Leu Gly Ile Thr Lys
                85              90                  95

Glu Arg Leu Gly Ala Pro Pro Leu Val Ser Ile Ile Met Thr Ser His
            100             105                 110

Asn Thr Glu Lys Phe Ile Glu Ala Ser Ile Asn Ser Leu Leu Leu Gln
            115             120             125

Thr Tyr Asn Asn Leu Glu Xaa Ile Xaa Val Asp Asp Tyr Ser Thr Asp
        130             135             140

Lys Thr Phe Xaa Ile Ala Ser Arg Ile Ala Asn Ser Thr Ser Lys Val
145             150             155             160

Lys Thr Phe Arg Leu Asn Ser Asn Leu Gly Thr Tyr Phe Ala Lys Asn
                165             170             175

Thr Gly Ile Leu Lys Ser Lys Gly Asp Ile Ile Phe Phe Gln Asp Ser
            180             185             190

Asp Asp Val Cys His His Glu Arg Ile Glu Arg Cys Val Asn Ala Leu
        195             200             205

Leu Ser Asn Lys Xaa Asn Ile Ala Val Arg Cys Ala Tyr Ser Arg Ile
        210             215             220

Asn Leu Glu Thr Gln Asn Ile Ile Lys Val Asn Xaa Asn Lys Tyr Lys
225             230             235             240

Leu Gly Leu Ile Thr Leu Gly Val Tyr Arg Lys Val Phe Xaa Glu Ile
            245             250             255

Gly Phe Phe Asn Cys Thr Thr Lys Ala Ser Asp Asp Glu Phe Xaa His
            260             265             270

Arg Ile Ile Lys Tyr Tyr Gly Lys Xaa Arg Ile Asn Asn Leu Phe Leu
        275             280             285

Pro Leu Tyr Tyr Asn Thr Met Arg Glu Xaa Ser Leu Phe Ser Asp Met
    290             295             300

Val Glu Trp Xaa Asp Xaa Asn Asn Ile Lys Gln Lys Thr Ser Asp Ala
305             310             315             320

Arg Gln Asn Tyr Leu His Glu Phe Gln Lys Ile His Asn Glu Arg Lys
            325             330             335

Xaa Asn Xaa Leu Lys Xaa Ile Phe Ser Phe Pro Arg Ile His Asp Ala
        340             345             350

Leu Pro Xaa Ser Lys Glu Met Ser Lys Leu Ser Asn Pro Lys Ile Pro
        355             360             365

Val Tyr Ile Asn Ile Cys Ser Ile Pro Ser Arg Ile Lys Gln Leu Gln
    370             375             380

Tyr Thr Ile Gly Xaa Leu Lys Asn Gln Cys Asp His Phe His Ile Tyr
385             390             395             400

```
Leu Asp Gly Tyr Pro Glu Xaa Pro Asp Phe Ile Lys Lys Leu Gly Asn
                405             410                 415

Lys Ala Thr Val Xaa Asn Cys Gln Xaa Lys Xaa Xaa Ser Ile Arg Asp
            420             425             430

Asn Gly Lys Phe Ile Leu Leu Glu Lys Leu Ile Lys Glu Asn Lys Asp
        435             440                 445

Gly Tyr Tyr Ile Thr Cys Asp Asp Ile Arg Tyr Pro Ala Asp Tyr
    450             455             460

Ile Asn Thr Met Ile Lys Lys Ile Asn Lys Tyr Xaa Asp Lys Ala Ala
465             470             475                         480

Ile Gly Leu His Gly Xaa Ile Phe Pro Ser Arg Val Asn Lys Tyr Phe
                485             490                 495

Ser Ser Asp Arg Ile Val Tyr Asn Phe Gln Lys Pro Leu Glu Lys Asp
            500             505             510

Xaa Ala Val Asn Xaa Leu Gly Thr Gly Thr Val Xaa Phe Arg Val Ser
        515             520             525

Xaa Phe Asn Xaa Phe Ser Leu Ser Asp Phe Xaa His Xaa Gly Met Xaa
    530             535             540

Asp Ile Tyr Phe Ser Xaa Leu Cys Lys Lys Asn Asn Ile Leu Gln Xaa
545             550             555                         560

Cys Ile Ser Arg Pro Xaa Asn Trp Leu Thr Glu Asp Asn Xaa Xaa Xaa
                565             570                 575

Glu Thr Leu Xaa His Xaa Xaa Xaa Xaa Asp Glu Xaa Gln Xaa Xaa
            580             585             590

Leu Ile Xaa Xaa Asn Xaa Pro Trp Gly Tyr Ser Ile Tyr Pro Leu
        595             600             605

Xaa Xaa Asn Xaa Xaa Xaa Xaa Xaa Leu Ile Pro Cys Leu Xaa Phe
    610             615             620

Tyr
625

<210>  35
<211>  625
<212>  PRT
<213>  Artificial Sequence

<220>
<223>  consensus sequence of alignment of pmHS, pglA and DcbF of FIG. 4D

<220>
<221>  MISC_FEATURE
<222>  (1)..(1)
<223>  M or L

<220>
<221>  MISC_FEATURE
<222>  (9)..(9)
<223>  any one of N, D, Q, E, B or Z

<220>
<221>  MISC_FEATURE
<222>  (32)..(35)
<223>  any amino acid

<220>
<221>  MISC_FEATURE
<222>  (50)..(50)
<223>  any amino acid
```

```
<220>
<221>  MISC_FEATURE
<222>  (51)..(51)
<223>  any one of N, D, Q, E, B or Z <220>
<221>  MISC_FEATURE
<222>  (58)..(58)
<223>  any one of N, D, Q, E, B or Z <220>
<221>  MISC_FEATURE
<222>  (72)..(76)
<223>  any amino acid <220>
<221>  MISC_FEATURE
<222>  (87)..(87)
<223>  I or V <220>
<221>  MISC_FEATURE
<222>  (91)..(91)
<223>  any one of N, D, Q, E, B or Z <220>
<221>  MISC_FEATURE
<222>  (135)..(135)
<223>  I or V <220>
<221>  MISC_FEATURE
<222>  (137)..(137)
<223>  I or V <220>
<221>  MISC_FEATURE
<222>  (148)..(148)
<223>  any one of N, D, Q, E, B or Z <220>
<221>  MISC_FEATURE
<222>  (213)..(213)
<223>  any one of N, D, Q, E, B or Z <220>
<221>  MISC_FEATURE
<222>  (236)..(236)
<223>  any one of N, D, Q, E, B or Z <220>
<221>  MISC_FEATURE
<222>  (254)..(254)
<223>  any one of N, D, Q, E, B or Z <220>
<221>  MISC_FEATURE
<222>  (271)..(271)
<223>  F or Y <220>
<221>  MISC_FEATURE
<222>  (281)..(281)
<223>  any one of N, D, Q, E, B, or Z <220>
<221>  MISC_FEATURE
<222>  (298)..(298)
<223>  any one of N, D, Q, E, B, or Z <220>
<221>  MISC_FEATURE
<222>  (308)..(308)
<223>  I or V <220>
<221>  MISC_FEATURE
<222>  (310)..(310)
<223>  any one of N, D, Q, E, B or Z <220>
<221>  MISC_FEATURE
<222>  (337)..(337)
<223>  any amino acid <220>
<221>  MISC_FEATURE
<222>  (339)..(339)
<223>  any one of N, D, Q, E, B or Z
```

```
<220>
<221> MISC_FEATURE
<222> (342)..(342)
<223> any one of N, D, Q, E, B or Z <220>
<221> MISC_FEATURE
<222> (355)..(355)
<223> I or V <220>
<221> MISC_FEATURE
<222> (389)..(389)
<223> I or V <220>
<221> MISC_FEATURE
<222> (407)..(407)
<223> I or V <220>
<221> MISC_FEATURE
<222> (421)..(421)
<223> I or V <220>
<221> MISC_FEATURE
<222> (425)..(425)
<223> any one of N, D, Q, E, B or Z <220>
<221> MISC_FEATURE
<222> (427)..(428)
<223> any one of N, D, Q, E, B or Z <220>
<221> MISC_FEATURE
<222> (476)..(476)
<223> any one of N, D, Q, E, B or Z <220>
<221> MISC_FEATURE
<222> (486)..(486)
<223> I or V
```

```
<220>
<221> MISC_FEATURE
<222> (513)..(513)
<223> any amino acid

<220>
<221> MISC_FEATURE
<222> (517)..(517)
<223> any amino acid

<220>
<221> MISC_FEATURE
<222> (524)..(524)
<223> any amino acid

<220>
<221> MISC_FEATURE
<222> (529)..(529)
<223> any amino acid

<220>
<221> MISC_FEATURE
<222> (532)..(532)
<223> any amino acid

<220>
<221> MISC_FEATURE
<222> (539)..(539)
<223> any amino acid

<220>
<221> MISC_FEATURE
<222> (541)..(541)
<223> any amino acid

<220>
<221> MISC_FEATURE
<222> (544)..(544)
<223> any amino acid

<220>
<221> MISC_FEATURE
<222> (550)..(550)
<223> any amino acid
```

```
<220>
<221> MISC_FEATURE
<222> (560)..(560)
<223> any amino acid

<220>
<221> MISC_FEATURE
<222> (566)..(566)
<223> any amino acid

<220>
<221> MISC_FEATURE
<222> (574)..(576)
<223> any amino acid

<220>
<221> MISC_FEATURE
<222> (580)..(580)
<223> any amino acid

<220>
<221> MISC_FEATURE
<222> (582)..(586)
<223> any amino acid

<220>
<221> MISC_FEATURE
<222> (589)..(589)
<223> any amino acid

<220>
<221> MISC_FEATURE
<222> (591)..(592)
<223> any amino acid

<220>
<221> MISC_FEATURE
<222> (595)..(596)
<223> any amino acid

<220>
<221> MISC_FEATURE
<222> (598)..(598)
<223> any amino acid

<220>
<221> MISC_FEATURE
<222> (609)..(610)
<223> any amino acid

<220>
<221> MISC_FEATURE
<222> (612)..(617)
<223> any amino acid

<220>
<221> MISC_FEATURE
<222> (623)..(623)
<223> any amino acid

<400> 35
```

Xaa Ser Leu Phe Lys Arg Ala Thr Xaa Leu Phe Lys Ser Gly Asn Tyr
1               5                   10                  15

Lys Asp Ala Leu Thr Leu Tyr Glu Asn Ile Ala Lys Ile Tyr Gly Xaa
                20                  25                  30

Xaa Xaa Xaa Ser Glu Ser Leu Val Lys Tyr Asn Ile Asp Ile Cys Lys
            35                  40                  45

Lys Xaa Xaa Ile Thr Gln Ser Lys Ser Xaa Lys Ile Glu Glu Asp Asn
        50                  55                  60

Ile Ser Gly Glu Asn Lys Phe Xaa Xaa Xaa Xaa Ser Val Ser Ile
65                  70                  75                  80

Lys Asp Leu Tyr Asn Glu Xaa Ser Asn Ser Xaa Leu Gly Ile Thr Lys
                85                  90                  95

Glu Arg Leu Gly Ala Pro Pro Leu Val Ser Ile Ile Met Thr Ser His
                100                 105                 110

CERTIFICATE OF CORRECTION (continued)
U.S. Pat. No. 7,771,981 B2

```
Asn Thr Glu Lys Phe Ile Glu Ala Ser Ile Asn Ser Leu Leu Leu Gln
        115                 120                 125

Thr Tyr Asn Asn Leu Glu Xaa Ile Xaa Val Asp Asp Tyr Ser Thr Asp
    130                 135                 140

Lys Thr Phe Xaa Ile Ala Ser Arg Ile Ala Asn Ser Thr Ser Lys Val
145                 150                 155                 160

Lys Thr Phe Arg Leu Asn Ser Asn Leu Gly Thr Tyr Phe Ala Lys Asn
                165                 170                 175

Thr Gly Ile Leu Lys Ser Lys Gly Asp Ile Ile Phe Phe Gln Asp Ser
            180                 185                 190

Asp Asp Val Cys His His Glu Arg Ile Glu Arg Cys Val Asn Ala Leu
        195                 200                 205

Leu Ser Asn Lys Xaa Asn Ile Ala Val Arg Cys Ala Tyr Ser Arg Ile
    210                 215                 220

Asn Leu Glu Thr Gln Asn Ile Ile Lys Val Asn Xaa Asn Lys Tyr Lys
225                 230                 235                 240

Leu Gly Leu Ile Thr Leu Gly Val Tyr Arg Lys Val Phe Xaa Glu Ile
                245                 250                 255

Gly Phe Phe Asn Cys Thr Thr Lys Ala Ser Asp Asp Glu Phe Xaa His
            260                 265                 270

Arg Ile Ile Lys Tyr Tyr Gly Lys Xaa Arg Ile Asn Asn Leu Phe Leu
        275                 280                 285

Pro Leu Tyr Tyr Asn Thr Met Arg Glu Xaa Ser Leu Phe Ser Asp Met
    290                 295                 300

Val Glu Trp Xaa Asp Xaa Asn Asn Ile Lys Gln Lys Thr Ser Asp Ala
305                 310                 315                 320

Arg Gln Asn Tyr Leu His Glu Phe Gln Lys Ile His Asn Glu Arg Lys
                325                 330                 335

Xaa Asn Xaa Leu Lys Xaa Ile Phe Ser Phe Pro Arg Ile His Asp Ala
            340                 345                 350

Leu Pro Xaa Ser Lys Glu Met Ser Lys Leu Ser Asn Pro Lys Ile Pro
        355                 360                 365

Val Tyr Ile Asn Ile Cys Ser Ile Pro Ser Arg Ile Lys Gln Leu Gln
370                 375                 380

Tyr Thr Ile Gly Xaa Leu Lys Asn Gln Cys Asp His Phe His Ile Tyr
385                 390                 395                 400

Leu Asp Gly Tyr Pro Glu Xaa Pro Asp Phe Ile Lys Lys Leu Gly Asn
                405                 410                 415

Lys Ala Thr Val Xaa Asn Cys Gln Xaa Lys Xaa Xaa Ser Ile Arg Asp
            420                 425                 430

Asn Gly Lys Phe Ile Leu Leu Glu Lys Leu Ile Lys Glu Asn Lys Asp
        435                 440                 445

Gly Tyr Tyr Ile Thr Cys Asp Asp Ile Arg Tyr Pro Ala Asp Tyr
    450                 455                 460
```

Ile Asn Thr Met Ile Lys Lys Ile Asn Lys Tyr Xaa Asp Lys Ala Ala
465                 470                 475                 480

Ile Gly Leu His Gly Xaa Ile Phe Pro Ser Arg Val Asn Lys Tyr Phe
                485                 490                 495

Ser Ser Asp Arg Ile Val Tyr Asn Phe Gln Lys Pro Leu Glu Lys Asp
            500                 505                 510

Xaa Ala Val Asn Xaa Leu Gly Thr Gly Thr Val Xaa Phe Arg Val Ser
        515                 520                 525

Xaa Phe Asn Xaa Phe Ser Leu Ser Asp Phe Xaa His Xaa Gly Met Xaa
    530                 535                 540

Asp Ile Tyr Phe Ser Xaa Leu Cys Lys Lys Asn Asn Ile Leu Gln Xaa
545                 550                 555                 560

Cys Ile Ser Arg Pro Xaa Asn Trp Leu Thr Glu Asp Asn Xaa Xaa Xaa
                565                 570                 575

Glu Thr Leu Xaa His Xaa Xaa Xaa Xaa Asp Glu Xaa Gln Xaa Xaa
            580                 585                 590

Leu Ile Xaa Xaa Asn Xaa Pro Trp Gly Tyr Ser Ser Ile Tyr Pro Leu
        595                 600                 605

Xaa Xaa Asn Xaa Xaa Xaa Xaa Xaa Leu Ile Pro Cys Leu Xaa Phe
610                 615                 620

Tyr
625